(12) United States Patent
Bangera et al.

(10) Patent No.: US 8,073,633 B2
(45) Date of Patent: Dec. 6, 2011

(54) COMPUTATIONAL METHODS AND SYSTEMS FOR SUGGESTING MODULATORS OF CYP450 AS TREATMENT OPTIONS

(75) Inventors: Mahalaxmi Gita Bangera, Renton, WA (US); Roderick A. Hyde, Redmond, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 536 days.

(21) Appl. No.: 12/319,154

(22) Filed: Dec. 30, 2008

(65) Prior Publication Data

US 2010/0169023 A1 Jul. 1, 2010

Related U.S. Application Data

(63) Continuation-in-part of application No. 12/319,153, filed on Dec. 30, 2008.

(51) Int. Cl.
*G06F 19/00* (2011.01)

(52) U.S. Cl. ........................... 702/19; 435/288.4

(58) Field of Classification Search .................. 702/19, 702/182–185; 435/288.4
See application file for complete search history.

(56) References Cited

U.S. PATENT DOCUMENTS

| | | |
|---|---|---|
| 5,658,881 A | 8/1997 | Gelland et al. |
| 5,731,319 A | 3/1998 | Aberg et al. |
| 6,037,157 A | 3/2000 | Norbeck et al. |
| 6,610,489 B2 | 8/2003 | Wolffe et al. |
| 6,625,547 B1 | 9/2003 | Korzekwa et al. |
| 6,673,778 B1 | 1/2004 | Iversen |
| 6,686,338 B1 | 2/2004 | Iversen |
| 6,790,632 B2 | 9/2004 | Zweig |
| 6,911,438 B2 | 6/2005 | Wright |
| 7,179,597 B2 | 2/2007 | Woosley |
| 7,208,600 B2 | 4/2007 | Cottrell et al. |
| 7,378,422 B2 | 5/2008 | Perni et al. |
| 2002/0142950 A1 | 10/2002 | Hayward et al. |
| 2003/0023387 A1 | 1/2003 | Gill-Garrison et al. |
| 2003/0167135 A1 | 9/2003 | Ewing |
| 2003/0212497 A1 | 11/2003 | Korzekwa et al. |
| 2004/0052865 A1 | 3/2004 | Gower et al. |
| 2004/0180392 A1 | 9/2004 | Prueksaritanont |
| 2004/0229829 A1 | 11/2004 | Iversen |
| 2004/0241714 A1 | 12/2004 | Branch et al. |
| 2005/0049294 A1 | 3/2005 | Palladino et al. |
| 2005/0222071 A1 | 10/2005 | Duranton et al. |
| 2006/0178837 A1 | 8/2006 | Gill-Garrison et al. |
| 2006/0188562 A1 | 8/2006 | Gower et al. |
| 2006/0253263 A1 | 11/2006 | Meshkin |

(Continued)

OTHER PUBLICATIONS

Akutsu, Tomoko; Kobayashi, Kaoru; Sakurada, Koichi; Ikegaya, Hiroshi; Furihata, Tomomi; and Chiba, Kan; "Identification of Human Cytochrome P450 Isozymes Involved in Diphenhydramine N-Demethylation"; Drug Metabolism and Disposition; bearing a date of 2007; pp. 72-78; vol. 35, No. 1; The American Society for Pharmacology and Experimental Therapeutics; U.S.A.

(Continued)

*Primary Examiner* — Edward Raymond

(57) ABSTRACT

Computational methods and systems are described which accept input, identify one or more CYP450-family enzymes, identify one or more modulators of the CYP450-family enzymes, and communicate treatments to at least one system user, wherein the treatments include one or more of the identified at least one modulator.

42 Claims, 55 Drawing Sheets

U.S. PATENT DOCUMENTS

| | | | |
|---|---|---|---|
| 2006/0289019 | A1 | 12/2006 | Marchand et al. |
| 2007/0003931 | A1 | 1/2007 | Mrazek et al. |
| 2007/0026480 | A1 | 2/2007 | Modak et al. |
| 2007/0166816 | A1* | 7/2007 | Campbell et al. .......... 435/288.4 |
| 2008/0085240 | A1 | 4/2008 | Flockhart et al. |

OTHER PUBLICATIONS

Al Omari, Amal; and Murry, Daryl J.; "Pharmacogenetics of the Cytochrome P450 Enzyme System: Review of Current Knowledge and Clinical Significance"; Journal of Pharmacy Practice; bearing a date of 2007; pp. 206-218; vol. 20.3; SAGE Publications.

"AmpliChip CYP450 Test for In Vitro Diagnostic Use"; Roche Diagnostics; bearing a date of Oct. 2007; pp. 1-36; Roche Molecular Systems, Inc.

Bailey, David G.; Malcolm, J.; Arnold, O.; and Spence, J. David; "Grapefruit juice-drug interactions"; British Journal of Clinical Pharmacology; bearing a date of 1998; pp. 101-110; vol. 46; Blackwell Publishing Ltd.

Beaird, Sandra L.; "HMG-CoA Reductase Inhibitors: Assessing Differences in Drug Interactions and Safety Profiles"; Journal of the American Pharmaceutical Association; bearing a date of 2000; pp. 637-644; vol. 40(5); American Pharmaceutical Association; found at http://www.medscape.com/viewarticle/406700.

Benet, Leslie Z.; and Cummins, Carolyn L.; "The drug efflux-metabolism alliance: biochemical aspects"; Advanced Drug Delivery Reviews; bearing a date of 2001; pp. S3-S11; vol. 50; Elsevier Science B.V.

Carruthers, S. George; Shoeman, Don W.; Hignite, Charles E.; and Azarnoff, Daniel L.; "Correlation between plasma diphenhydramine level and sedative and antihistamine effects"; Clinical Pharmacology & Therapeutics; bearing a date of Apr. 1978; vol. 23, No. 4: pp. 375-382.

Cederbaum, Arthur I.; "CYP2E1—Biochemical and Toxicological Aspects and Role in Alcohol-Induced Liver Injury"; The Mount Sinai Journal of Medicine; bearing a date of Jul. 2006; vol. 73, No. 4; pp. 657-672.

Chen, Jie; Yang, Xiao-Xia; Min, Huang; Hu, Ze-Ping; He, Ming; Duan, Wei; Chan, Eli; Sheu, Fwu-Shan; Chen, Xiao; and Zhou Shu-Feng; "Small Interfering RNA-Mediated Silencing of Cytochrome P450 3A4 Gene"; DMD Fast Forward; bearing a date of Jun. 7, 2006; as doi:10.1124/dmd.106.009837; pp. 1-48; American Society for Pharmacology and Experimental Therapeutics.

Coumoul, Xavier; Diry, Monique; Robillot, Cedric; and Barouki, Robert; "Differential Regulation of Cytochrome P450 1A1 and 1B1 by a Combination of Dioxin and Pesticides in the Breast Tumor Cell Line MCF-7"; Cancer Research; bearing a date of May 15, 2001; vol. 61; pp. 3942-3948.

"CYP3A4"; Wikipedia; pp. 1-6; found at http://en.wikipedia.org/wiki/CYP3A4; printed Nov. 7, 2008.

"Cytochrome P450"; Wikipedia; pp. 1-9; found at http://en.wikipedia.org/wiki/Cytochrome_P450; printed Nov. 7, 2008.

Dai, Yan; and Cederbaum, Arthur I.; "Inactivation and Degradation of Human Cytochrome P4502E1 by $CCl_4$ in a Transfected Hep62 Cell Line"; The Journal of Pharmacology and Experimental Therapeutics; bearing a date of 1995; pp. 1614-1622; vol. 275, No. 3; found at jpet.aspetjournals.org.

Do Rego, Amalia Cinthia Meneses; Filho, Irami Araujo; Damasceno, Bolivar P G L; Egito, Eryvaldo Socrates Tabosa; Da Silveira, Ivanaldo Amancio; Brandao-Neto, Jose; and Medeiros, Aldo Cunha; "Simvastatin improves the healing of infected skin wounds of rats"; Acta Cirurgica Brasileira; bearing a date of 2007; pp. 57-63; vol. 22, Supplement 1.

Girre, Catherine; Lucas, Daniele; Hispard, Eric; Menez, Catherine; Dally, Sylvain; and Menez, Jean-Francois; "Assessment of Cytochrome P4502E1 Induction in Alcoholic Patients by Chlorzoxazone Pharmacokinetics"; bearing a date of 1994; Biochemical Pharmacology; pp. 1503-1508; vol. 47, No. 9; Elsevier Science Ltd.

Guengerich, F. Peter; "Cytochrome P450 and Chemical Toxicology"; Chemical Research in Toxicology; bearing a date of 2008; pp. 70-83; vol. 21, No. 1; American Chemical Society.

Gupta, Rajesh; Plantinga, Laura C.; Fink, Nancy E.; Melamed, Michal L.; Coresh, Josef; Fox, Caroline S.; Levin, Nathan W.; and Powe, Neil R.; "Statin Use and Hospitalization for Sepsis in Patients With Chronic Kidney Disease"; Journal of the American Medical Association; bearing a date of Apr. 4, 2007; pp. 1455-1464; vol. 297, No. 13; American Medical Association; located at http://jama.ama-assn.org/cgi/content/full/297/13/1455.

Gupta, Rajesh; Plantinga, Laura C.; and Powe, Neil R.; "Correction: Inaccurate Classification and Information Reported in a Study of Statin Use and Sepsis in Patients With Chronic Kidney Disease"; Journal of the American Medical Association; bearing a date of Feb. 20, 2008; pp. 765-766; vol. 299, No. 7; American Medical Association.

Hanna, Imad H.; Dawling, Sheila; Roodi, Nady; Guengerich, F. Peter; and Parl, Fritz F.; "Cytochrome P450 1B1 (CYP1B1) Pharmacogenetics: Association of Polymorphismms with Functional Differences in Estrogen Hydroxylation Activity"; Cancer Research; bearing a date of Jul. 1, 2000; pp. 3440-3444; vol. 60.

Hanukoglu, Israel; "Steroidogenic enzymes: structure, function, and role in regulation of steroid hormone biosynthesis"; Laboratory of Steroid Molecular Biology; bearing a date of 1992; pp. 1-38.

Hedl, Matija; and Rodwell, Victor W.; "Inhibition of the Class II HMG-CoA reductase of Pseudomonas mevalonii"; Protein Science; bearing a date of 2004; pp. 1693-1697; vol. 13; Cold Spring Harbor Laboratory Press.

Hunter, Janice; and Hirst, Barry H.; "Intestinal secretion of drugs. The role of P-glycoprotein and related drug efflux systems in limiting oral drug absorption"; Advanced Drug Delivery Reviews; bearing a date of 1997; pp. 129-157; vol. 25; Elsevier Science B.V.

Jaeschke, Hartmut; Gores, Gregory J.; Cederbaum, Arthur I.; Hinson, Jack A.; Pessayre, Dominique; and Lemasters, John J.; "FORUM Mechanisms of Hepatotoxicity"; Toxicological Sciences; bearing a date of 2001; pp. 166-176; vol. 65; The Society of Toxicology.

Jenwitheesuk, Ekachai; Horst, Jeremy A.; Rivas, Kasey L.; Van Voorhis, Wesley C.; and Samudrala, Ram; "Novel paradigms for drug discovery: computational multitarget screening"; Trends in Pharmacological Sciences; bearing a date of Jan. 10, 2008; pp. 62-71; vol. 29, No. 2; Elsevier Ltd.

Kalra, Bhupinder Singh; "Cytochrome P450 Enzyme Isoforms and Their Therapeutic Implications: An Update"; Indian Journal of Medical Sciences; bearing a date of Feb. 2007; pp. 102-116; vol. 61, No. 1.

Kivisto, Kari T.; Kroemer, Heyo K.; and Eichelbaum, Michel; "The role of human cytochrome P450 enzymes in the metabolism of anticancer agents: implications for drug interactions"; British Journal of Clinical Pharmacology; bearing a date of 1995; pp. 523-530; vol. 40; Blackwell Science Ltd.

Liappis, A. P.; Kan, V. L.; Rochester, C. G.; and Simon, G. L.; "The Effect of Statins on Mortality in Patients with Bacteremia"; Clinical Infectious Diseases; bearing a date of Oct. 15, 2001; pp. 1352-1357; vol. 33; Infectious Diseases Society of America.

Madan, Ajay; Graham, Richard A.; Carroll, Kathleen M.; Mudra, Daniel R.; Burton, L. Alayne; Krueger, Linda A.; Downey, April D.; Czerwinski, Maciej; Forster, Jameson; Ribadeneira, Maria D.; Gan, Liang-Shang; Lecluyse, Edward L.; Zech, Karl; Robertson, Philmore Jr.; Koch, Patrick; Antonian, Lida; Wagner, Greg; Yu, Li; and Parkinson, Andrew; "Effects of Prototypical Microsomal Enzyme Inducers on Cytochrome P450 Expression in Cultured Human Hepatocytes"; Drug Metabolism and Disposition; bearing a date of 2003; pp. 421-431; vol. 31, No. 4; The American Society for Pharmacology and Experimental Therapeutics.

McFadyen, Mce; Melvin, WT; and Murray, GI; "Cytochrome P450 CYP1B1 activity in renal cell carcinoma"; British Journal of Cancer; bearing a date of 2004; pp. 966-971; vol. 91(5); Cancer Research UK.

Neuvonen, Pertti J.; Kantola, Teemu; and Kivisto, Kari T.; "Simvastatin but not pravastatin is very susceptible to interaction with the CYP3A4 inhibitor itraconazole"; Clinical Pharmacology & Therapeutics; bearing a date of Mar. 1998; pp. 332-341; vol. 63, No. 3; Mosby, Inc.

Oscarson, Mikael; "Pharmacogenetics of Drug Metabolising Enzymes: Importance for Personalised Medicine"; Clinical Chemistry and Laboratory Medicine; bearing a date of 2003; pp. 573-580; vol. 41, No. 4; Walter de Gruyter • Berlin • New York.

"Personalized Medicine Europe: Health, Genes & Society"; Abstracts presented The Yoran Institute for Human Genome Research, Tel-Aviv University/European Science Foundation Workshop; bearing a date of Jun. 19-21, 2005; Personalized Medicine; pp. 143-185; vol. 2, No. 2; Future Medicine Ltd.

"Pierce® BCA Protein Assay Kit Instructions"; Thermo Scientific; bearing a date of 2008; pp. 1-7; Thermo Fisher Scientific Inc.; U.S.A.; found at www.thermo.com/pierce.

Robertson, Philmore; Decory, Heleen H.; Madan, Ajay; and Parkinson, Andrew; "In Vitro Inhibition and Induction of Human Hepatic Cytochrome P450 Enzymes by Modafinil"; Drug Metabolism and Disposition; bearing a date of 2000; pp. 664-671; vol. 28, No. 6; The American Society for Pharmacology and Experimental Therapeutics; U.S.A.

Rodriguez-Antona, C; and Ingelman-Sundberg, M; "Cytochrome P450 pharmacogenetics and cancer"; Oncogene; bearing a date of 2006; pp. 1679-1691; vol. 25; Nature Publishing Group.

Roy, Partha; Yu, Li J.; Crespi, Charles L.; and Waxman, David J.; "Development of a Substrate-Activity Based Approach to Identify the Major Human Liver P-450 Catalysts of Cyclophosphamide and Ifosfamide Activation Based on cDNA-Expressed Activities and Liver Microsomal P-450 Profiles"; Drug Metabolism and Disposition; bearing a date of 1999; pp. 655-666; vol. 27, No. 6; The American Society for Pharmacology and Experimental Therapeutics; U.S.A.

Tabernero, Lydia; Rodwell, Victor W.; and Stauffacher, Cynthia V.; "Crystal Structure of a Statin Bound to a Class II Hydroxymethylglutaryl-CoA Reductase"; The Journal of Biological Chemistry; bearing a date of May 30, 2003; pp. 19933-19938; vol. 278, No. 22; JBC Papers in Press.

Takada, Kazuki; Arefayene, Million; Desta, Zeruesenay; Yarboro, Cheryl H.; Boumpas, Dimitrios T.; Balow, James E.; Flockhart, David A.; and Illei, Gabor G.; "Cytochrome P450 Pharmacogenetics as a Predictor of Toxicity and Clinical Response to Pulse Cyclophosphamide in Lupus Nephritis"; Arthritis & Rheumatism; bearing a date of Jul. 2004; pp. 2202-2210; Vol. 50, No. 7; American College of Rheumatology.

Takahashi, S; Takahashi, T; Mizobuchi, S; Matsumi, M; Morita, K; Miyazaki, M; Namba, M; Akagi, R; and Hirakawa, M; "Increased Cytotoxicity of Carbon Tetrachloride in a Human Hepatoma Cell Line Overexpressing Cytochrome P450 2E1"; The Journal of International Medical Research; bearing a date of 2002; pp. 400-405; vol. 30; Cambridge Medical Publications.

Wilding, E. Imogen; Brown, James R.; Bryant, Alexander P.; Chalker, Alison F.; Holmes, David J.; Ingraham, Karen A.; Iordanescu, Serban; So, Chi Y.; Rosenberg, Martin; and Gwynn, Michael N.; "Identification, Evolution, and Essentiality of the Mevalonate Pathway for Isopentenyl Diphosphate Biosynthesis in Gram-Positive Cocci"; Journal of Bacteriology; bearing a date of Aug. 2000; pp. 4319-4327; vol. 182, No. 15; American Society for Microbiology.

Zanger, Ulrich M.; Raimundo, Sebastian; and Eichelbaum, Michel; "Cytochrome P450 2D6: overview and update on pharmacology, genetics, biochemistry"; Naunyn-Schmiedeberg's Archives of Pharmacology; bearing a date of 2004; pp. 23-37; vol. 369; Springer-Verlag.

* cited by examiner

FIG. 2

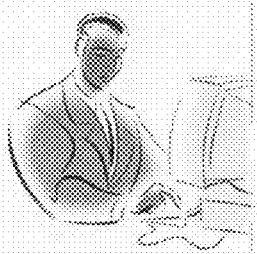

10 System User

100
A system

110
Circuitry for accepting input that specifies an individual

200
Wherein the individual is a representative individual

120
Circuitry for accepting input that identifies a drug therapy associated with the individual

210
Wherein the drug therapy includes a statin therapy

220
Wherein the drug therapy includes a acetominophen therapy

230
Wherein the drug therapy includes a cancer chemotherapy

130
Circuitry for identifying at least one first CYP450-family enzyme that influences metabolism of the drug therapy associated with the individual

140
Circuitry for identifying at least one second CYP450-family enzyme that influences metabolism of the drug therapy associated with the individual

150
Circuitry for identifying at least one modulator of one or more of the at least one first CYP450-family enzyme

160
Circuitry for identifying at least one modulator of one or more of the at least one second CYP450-family enzyme

170
Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme

180
Database

FIG. 3

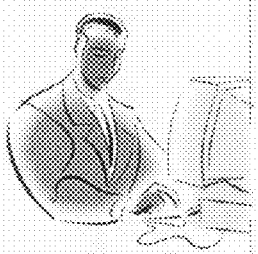

10 System User

180 Database

100 A system

110 Circuitry for accepting input that specifies an individual

120 Circuitry for accepting input that identifies a drug therapy associated with the individual 300 Wherein the drug therapy includes a hormone-related therapy 130 Circuitry for identifying at least one first CYP450-family enzyme that influences metabolism of the drug therapy associated with the individual 310 Wherein the at least one first CYP450-family enzyme that influences metabolism of the drug therapy influences metabolism directly 140 Circuitry for identifying at least one second CYP450-family enzyme that influences metabolism of the drug therapy associated with the individual 320 Wherein the at least one second CYP450-family enzyme that influences metabolism of the drug therapy influences metabolism directly 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme

FIG. 4

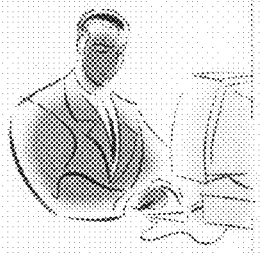

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 400 Wherein the at least one modulator of one or more of the at least one first CYP450-family enzyme is an endogenous modulator 410 Wherein the at least one modulator of one or more of the at least one first CYP450-family enzyme is an exogenous modulator 160 Circuitry for identifying at least one modulator of one or more of the at least one second CYP450-family enzyme 420 Wherein the at least one modulator of one or more of the at least one second CYP450-family enzyme is an endogenous modulator 430 Wherein the at least one modulator of one or more of the at least one second CYP450-family enzyme is an exogenous modulator 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme

FIG. 5

100 A system

110 Circuitry for accepting input that specifies an individual

120 Circuitry for accepting input that identifies a drug therapy associated with the individual

130 Circuitry for identifying at least one first CYP450-family enzyme that influences metabolism of the drug therapy associated with the individual

140 Circuitry for identifying at least one second CYP450-family enzyme that influences metabolism of the drug therapy associated with the individual

150 Circuitry for identifying at least one modulator of one or more of the at least one first CYP450-family enzyme

500 Wherein the at least one modulator of one or more of the at least one first CYP450-family enzyme is a synthetic modulator

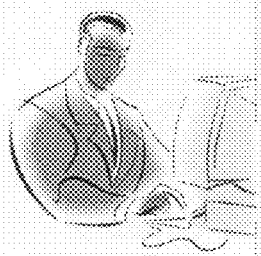
10 System User

180 Database

160 Circuitry for identifying at least one modulator of one or more of the at least one second CYP450-family enzyme

510 Wherein the at least one modulator of one or more of the at least one second CYP450-family enzyme is a synthetic modulator

170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme

FIG. 6

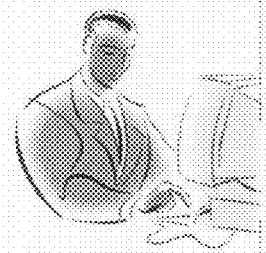

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme 600
Circuitry for suggesting one or more dosages of the one or more treatment to a system user;
Circuitry for identifying at least one environmental factor associated with an alteration in activity of at least one of the one or more treatment; and
Circuitry for communicating one or more alternate dosages of the one or more treatment to a system user, wherein the one or more alternate dosages are calculated to compensate for the alteration in activity of at least one of the one or more treatment

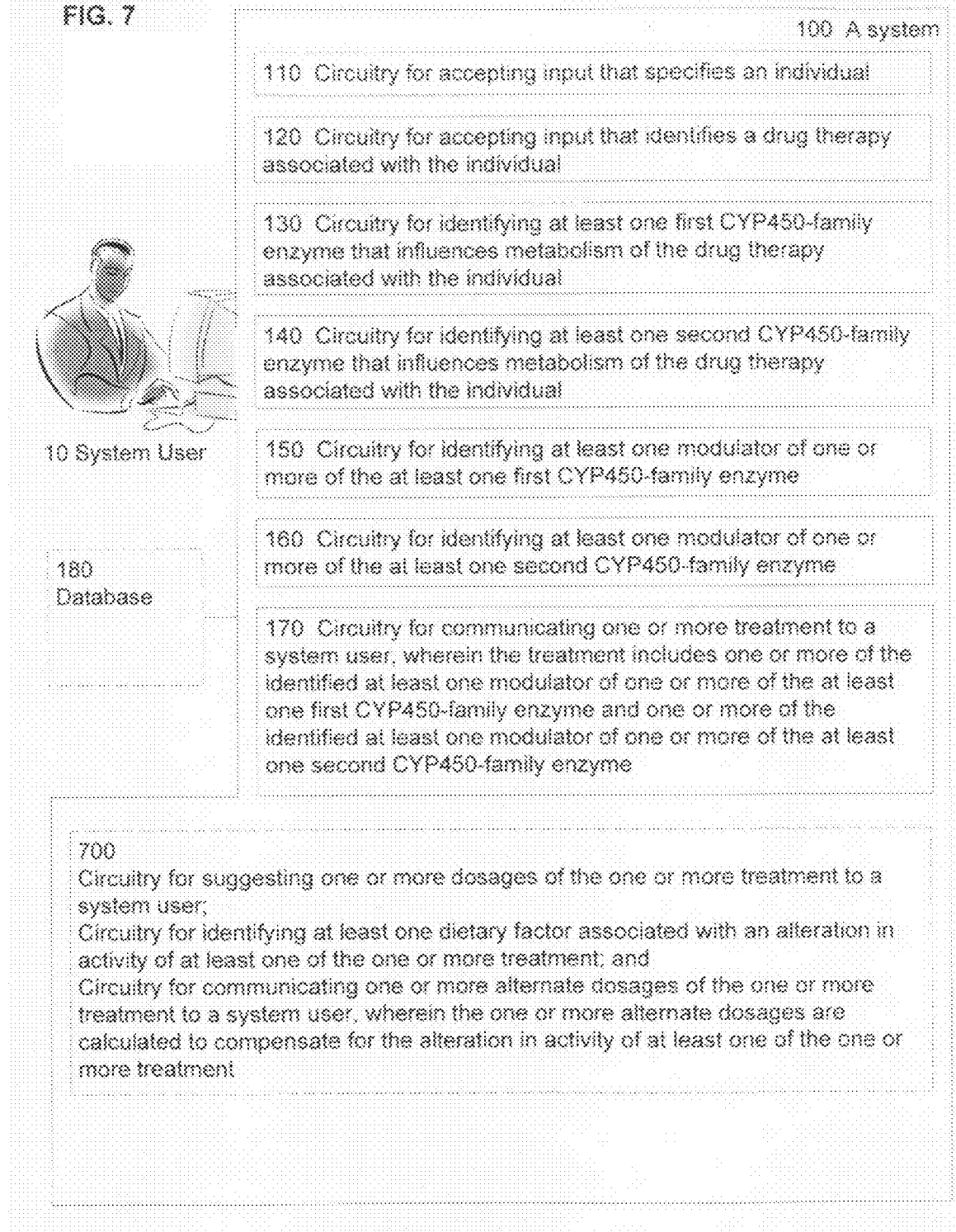

FIG. 8

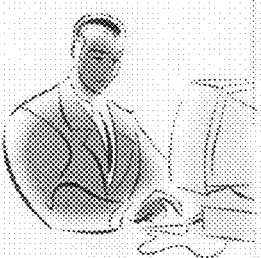

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme 800
Circuitry for suggesting one or more dosage schedules of the one or more treatment to a system user;
Circuitry for identifying at least one environmental factor associated with an alteration in activity of at least one of the one or more treatment; and
Circuitry for communicating one or more alternate dosage schedules of the one or more treatment to a system user, wherein the one or more alternate dosage schedules are calculated to compensate for the alteration in activity of at least one of the one or more treatment

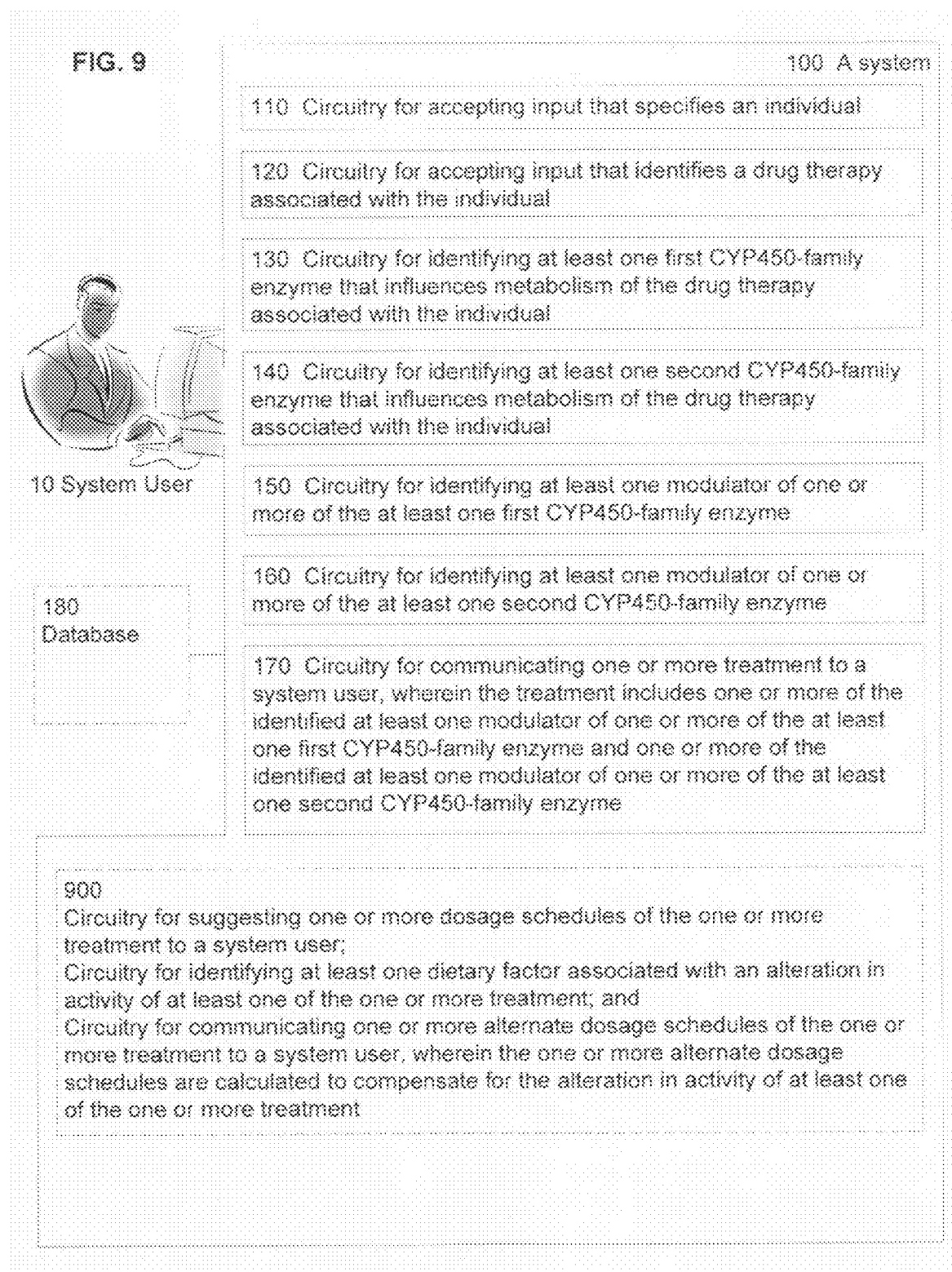

FIG. 10

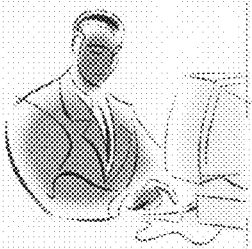

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme 1000
Circuitry for accepting input specifying one or more variant of at least one CYP450-family enzyme that influences metabolism of the drug therapy associated with the individual;
Circuitry for identifying at least one modulator of at least one of the one or more variant; and
Circuitry for communicating one or more treatment to a system user, wherein the treatment includes the identified at least one modulator of at least one of the one or more variant 1010
Wherein the one or more variant of at least one CYP450-family enzyme is directly associated with the individual

FIG. 11

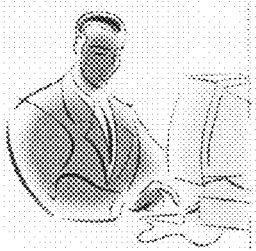

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme 1100
Circuitry for accepting input specifying one or more variant of at least one CYP450-family gene that influences metabolism of the drug therapy associated with the individual;
Circuitry for identifying at least one modulator of at least one of the one or more variant of at least one CYP450-family gene; and
Circuitry for communicating one or more treatment to a system user, wherein the treatment includes the identified at least one modulator of at least one of the one or more variant of at least one CYP450-family gene 1110
Wherein the one or more variant of at least one CYP450-family gene is directly associated with the individual

FIG. 12

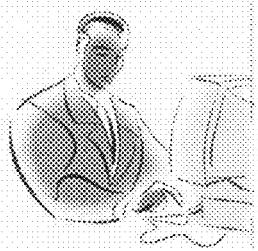

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme 1200
Circuitry for accepting input specifying one or more variant of the at least one first CYP450-family enzyme that influences metabolism of the drug therapy associated with the individual;
Circuitry for accepting input specifying one or more variant of the at least one second CYP450-family enzyme that influences metabolism of the drug therapy associated with the individual;
Circuitry for identifying at least one modulator of the one or more variant of the at least one first CYP450-family enzyme;
Circuitry for identifying at least one modulator of the one or more variant of the at least one second CYP450-family enzyme; and
Circuitry for communicating one or more treatment to a system user, wherein the treatment includes the identified at least one modulator of the one or more variant of the at least one first CYP450-family enzyme and the identified at least one modulator of the one or more variant of the at least one second CYP450-family enzyme

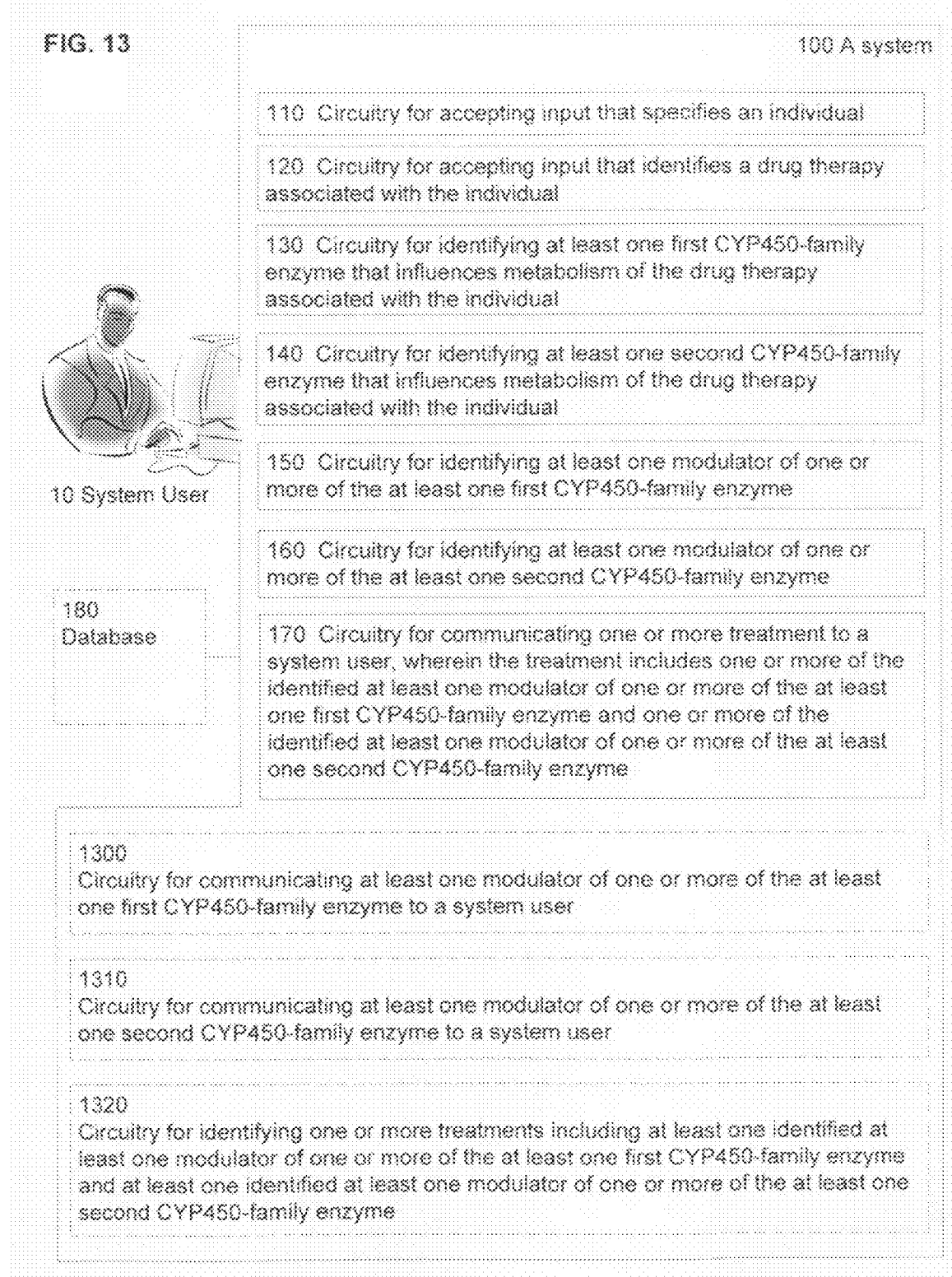

FIG. 14

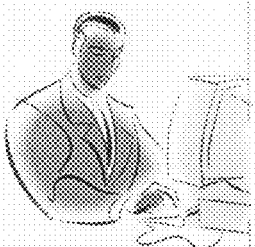

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme 1400
Circuitry for identifying at least one environmental factor associated with activity of at least one CYP450-family enzyme that influences metabolism of the drug therapy associated with the individual; and
Circuitry for communicating at least one environmental mitigation strategy to a system user 1410
Wherein the at least one environmental factor is associated with the individual

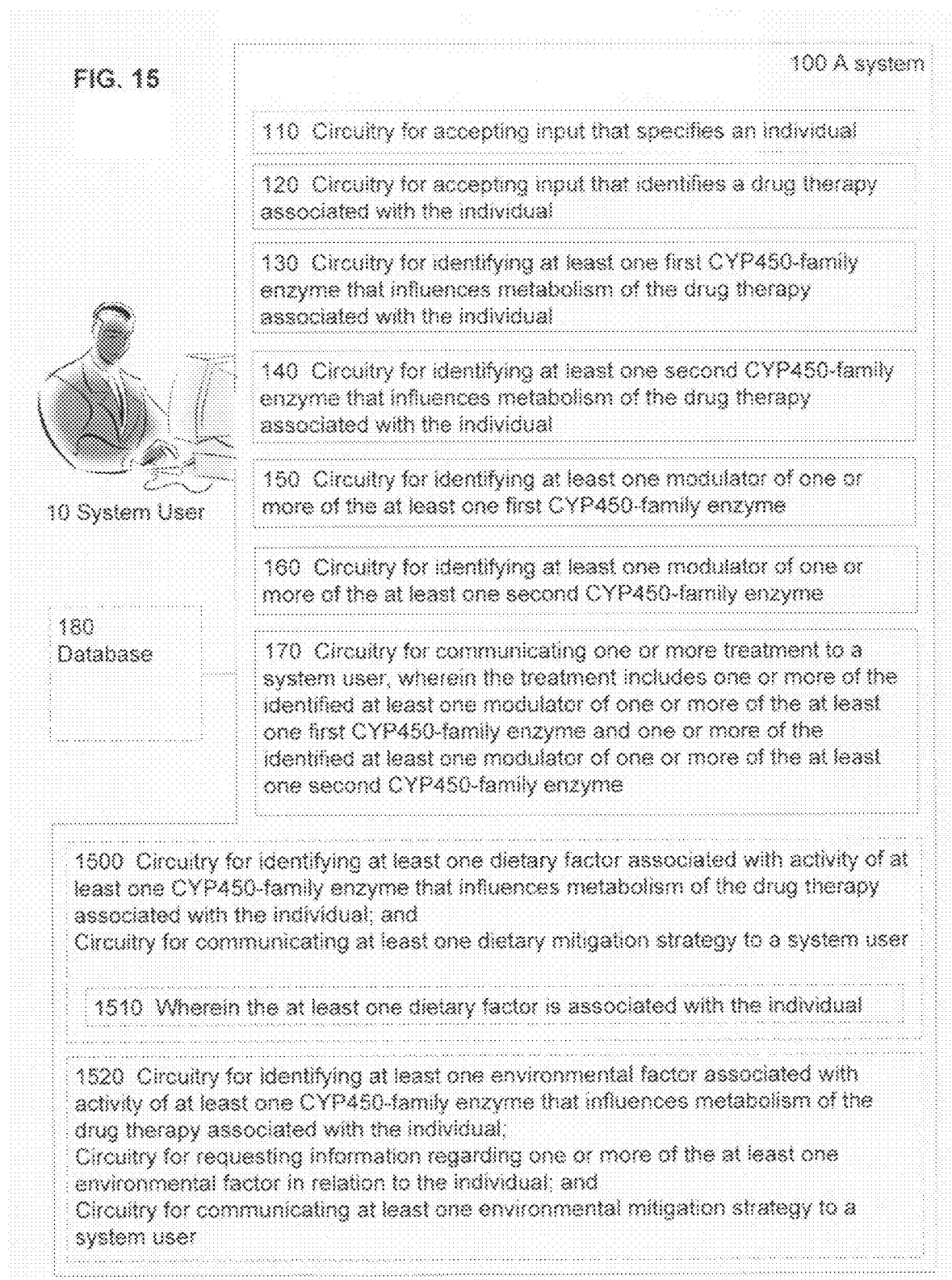

FIG. 16

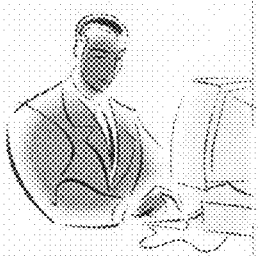

10 System User

180 Database

100 A system

110 Circuitry for accepting input that specifies an individual

120 Circuitry for accepting input that identifies a drug therapy associated with the individual 130 Circuitry for identifying at least one first CYP450-family enzyme that influences metabolism of the drug therapy associated with the individual 140 Circuitry for identifying at least one second CYP450-family enzyme that influences metabolism of the drug therapy associated with the individual 150 Circuitry for identifying at least one modulator of one or more of the at least one first CYP450-family enzyme 160 Circuitry for identifying at least one modulator of one or more of the at least one second CYP450-family enzyme 170 Circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme 1600 Circuitry for associating at least one anatomic location with predicted activity of the at least one first CYP450-family enzyme;
Circuitry for associating the at least one anatomic location with one or more of the at least one modulator of the at least one first CYP450-family enzyme; and
Circuitry for communicating one or more treatment to a system user, wherein the treatment includes the at least one modulator of the at least one first CYP450-family enzyme associated with the at least one anatomic location 1610 Circuitry for associating at least one anatomic location with predicted activity of the at least one second CYP450-family enzyme;
Circuitry for associating the at least one anatomic location with one or more of the at least one modulator of the at least one second CYP450-family enzyme; and
Circuitry for communicating one or more treatment to a system user, wherein the treatment includes the at least one modulator of the at least one second CYP450-family enzyme associated with the at least one anatomic location

FIG. 17

10 System User

1795
Database

1700
A system

1710
Circuitry for accepting input that specifies an individual

1780
Wherein the individual is a representative individual

1720
Circuitry for accepting input that identifies a first drug therapy associated with the individual 1785
Wherein the input that identifies a first drug therapy associated with the individual identifies a statin therapy 1730
Circuitry for accepting input that identifies a second drug therapy associated with the individual 1790
Wherein the input that identifies a second drug therapy associated with the individual identifies a statin therapy 1740
Circuitry for identifying at least one CYP450-family enzyme that influences metabolism of both the first drug therapy and the second drug therapy 1750
Circuitry for identifying at least one modulator of one or more of the at least one CYP450-family enzyme 1770
Circuitry for communicating one or more treatment to a system user, wherein the treatment includes one or more of the at least one modulator

FIG. 18

10 System User

1795
Database

1700
A system

1710
Circuitry for accepting input that specifies an individual

1720
Circuitry for accepting input that identifies a first drug therapy associated with the individual 1800
Wherein the input that identifies a first drug therapy associated with the individual identifies a cancer chemotherapy 1810
Wherein the input that identifies a first drug therapy associated with the individual identifies a hormone-related therapy 1730
Circuitry for accepting input that identifies a second drug therapy associated with the individual 1820
Wherein the input that identifies a second drug therapy associated with the individual identifies a cancer chemotherapy 1830
Wherein the input that identifies a second drug therapy associated with the individual identifies a hormone-related therapy 1740
Circuitry for identifying at least one CYP450-family enzyme that influences metabolism of both the first drug therapy and the second drug therapy 1750
Circuitry for identifying at least one modulator of one or more of the at least one CYP450-family enzyme 1770
Circuitry for communicating one or more treatment to a system user, wherein the treatment includes one or more of the at least one modulator

FIG. 19

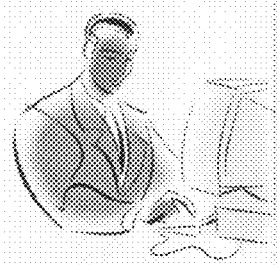
10 System User

1795 Database

1700 A system

1710 Circuitry for accepting input that specifies an individual

1720 Circuitry for accepting input that identifies a first drug therapy associated with the individual
  1900 Wherein the input that identifies a first drug therapy associated with the individual identifies an acetominophen therapy
    1910 Wherein the identifying at least one CYP450-family enzyme that influences metabolism of both the first drug therapy and the second drug therapy includes identifying a CYP2E enzyme 1730 Circuitry for accepting input that identifies a second drug therapy associated with the individual
  1920 Wherein the input that identifies a second drug therapy associated with the individual identifies an acetominophen therapy
    1930 Wherein the identifying at least one CYP450-family enzyme that influences metabolism of both the first drug therapy and the second drug therapy includes identifying a CYP2E enzyme 1740 Circuitry for identifying at least one CYP450-family enzyme that influences metabolism of both the first drug therapy and the second drug therapy 1750 Circuitry for identifying at least one modulator of one or more of the at least one CYP450-family enzyme 1770 Circuitry for communicating one or more treatment to a system user, wherein the treatment includes one or more of the at least one modulator

FIG. 20

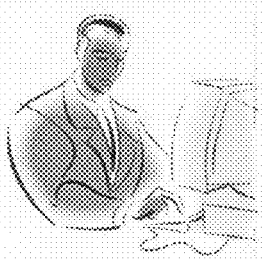

10 System User

1795 Database

1700 A system

1710 Circuitry for accepting input that specifies an individual

1720 Circuitry for accepting input that identifies a first drug therapy associated with the individual 1730 Circuitry for accepting input that identifies a second drug therapy associated with the individual 1740 Circuitry for identifying at least one CYP450-family enzyme that influences metabolism of both the first drug therapy and the second drug therapy 2000 Wherein the at least one CYP450-family enzyme that influences metabolism of both the first drug therapy and the second drug therapy directly influences metabolism 1750 Circuitry for identifying at least one modulator of one or more of the at least one CYP450-family enzyme 2010 Wherein the at least one modulator of one or more of the at least one CYP450-family enzyme is an endogenous modulator 2020 Wherein the at least one modulator of one or more of the at least one CYP450-family enzyme is an exogenous modulator 2030 Wherein the at least one modulator of one or more of the at least one CYP450-family enzyme is a synthetic modulator 1770 Circuitry for communicating one or more treatment to a system user, wherein the treatment includes one or more of the at least one modulator

FIG. 21

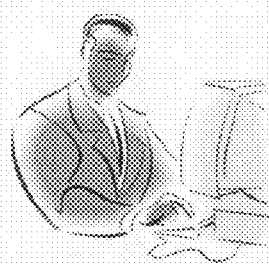

10 System User

1795 Database

1700
A system

1710
Circuitry for accepting input that specifies an individual

1720
Circuitry for accepting input that identifies a first drug therapy associated with the individual 1730
Circuitry for accepting input that identifies a second drug therapy associated with the individual 1740
Circuitry for identifying at least one CYP450-family enzyme that influences metabolism of both the first drug therapy and the second drug therapy 1750
Circuitry for identifying at least one modulator of one or more of the at least one CYP450-family enzyme 1770
Circuitry for communicating one or more treatment to a system user, wherein the treatment includes one or more of the at least one modulator 2100
Circuitry for accepting input specifying one or more variant of at least one CYP450-family enzyme associated with the individual;
Circuitry for identifying at least one modulator of the one or more variant; and
Circuitry for communicating one or more treatment to a system user, wherein the one or more treatment includes one or more of the identified at least one modulator of the one or more variant 2110
Wherein the one or more variant of at least one CYP450-family enzyme is directly associated with the individual

FIG. 22

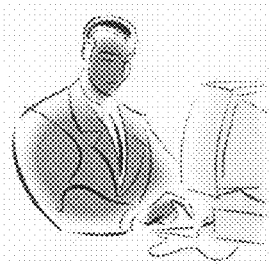

10 System User

1795
Database

1700
A system

1710
Circuitry for accepting input that specifies an individual

1720
Circuitry for accepting input that identifies a first drug therapy associated with the individual 1730
Circuitry for accepting input that identifies a second drug therapy associated with the individual 1740
Circuitry for identifying at least one CYP450-family enzyme that influences metabolism of both the first drug therapy and the second drug therapy 1750
Circuitry for identifying at least one modulator of one or more of the at least one CYP450-family enzyme 1770
Circuitry for communicating one or more treatment to a system user, wherein the treatment includes one or more of the at least one modulator 2200
Circuitry for accepting input specifying one or more variant of at least one CYP450-family gene associated with the individual;
Circuitry for identifying at least one modulator of the one or more variant of at least one CYP450-family gene; and
Circuitry for communicating one or more treatment to a system user, wherein the one or more treatment includes one or more of the identified at least one modulator of the one or more variant of the at least one CYP450-family gene 2210
Wherein the one or more variant of at least one CYP450-family gene is directly associated with the individual

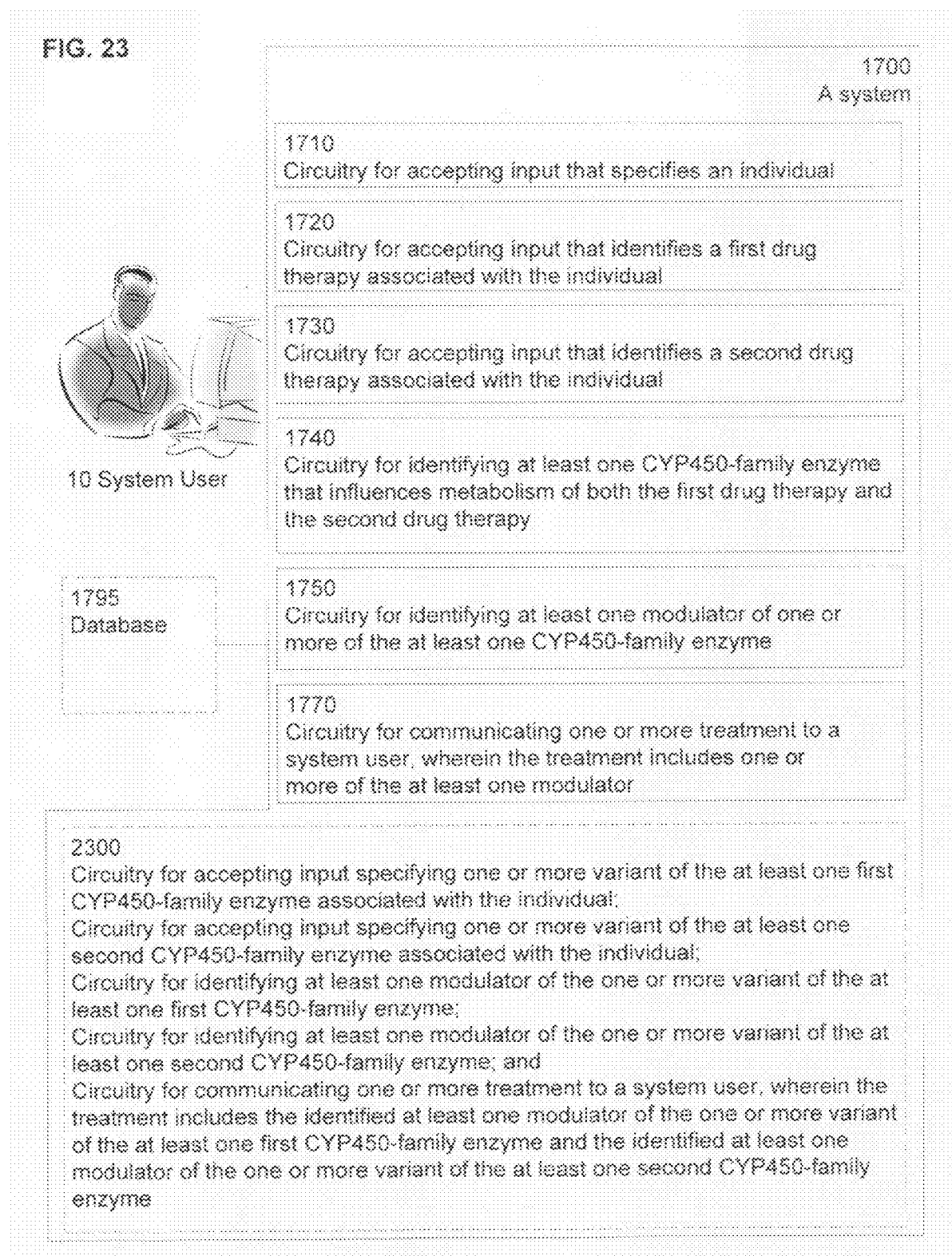

FIG. 24

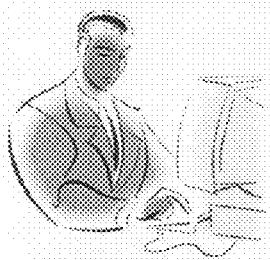
10 System User

1795
Database

1700
A system

1710
Circuitry for accepting input that specifies an individual

1720
Circuitry for accepting input that identifies a first drug therapy associated with the individual 1730
Circuitry for accepting input that identifies a second drug therapy associated with the individual 1740
Circuitry for identifying at least one CYP450-family enzyme that influences metabolism of both the first drug therapy and the second drug therapy 1750
Circuitry for identifying at least one modulator of one or more of the at least one CYP450-family enzyme 1770
Circuitry for communicating one or more treatment to a system user, wherein the treatment includes one or more of the at least one modulator 2400
Circuitry for communicating at least one modulator of one or more of the at least one first CYP450-family enzyme to a system user 2410
Circuitry for communicating at least one modulator of one or more of the at least one second CYP450-family enzyme to a system user 2420
Circuitry for identifying one or more treatments including at least one identified at least one modulator of one or more of the at least one first CYP450-family enzyme and at least one identified at least one modulator of one or more of the at least one second CYP450-family enzyme

FIG. 25

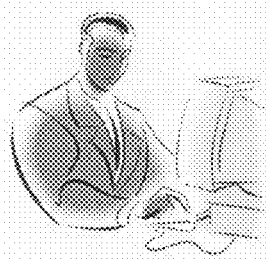
10 System User

1795
Database

1700
A system

1710
Circuitry for accepting input that specifies an individual

1720
Circuitry for accepting input that identifies a first drug therapy associated with the individual 1730
Circuitry for accepting input that identifies a second drug therapy associated with the individual 1740
Circuitry for identifying at least one CYP450-family enzyme that influences metabolism of both the first drug therapy and the second drug therapy 1750
Circuitry for identifying at least one modulator of one or more of the at least one CYP450-family enzyme 1770
Circuitry for communicating one or more treatment to a system user, wherein the treatment includes one or more of the at least one modulator 2500
Circuitry for suggesting one or more dosages of the one or more treatment to a system user;
Circuitry for identifying at least one environmental factor associated with an alteration in activity of at least one of the one or more treatment; and
Circuitry for communicating one or more alternate dosages of the one or more treatment, wherein the one or more alternate dosages are calculated to compensate for the alteration in activity of at least one of the one or more treatment 2510 Circuitry for identifying at least one environmental factor associated with activity of the at least one CYP450-family enzyme; and
circuitry for communicating at least one environmental mitigation strategy to a system user 2520
Wherein the at least one environmental factor is associated with the individual

FIG. 26

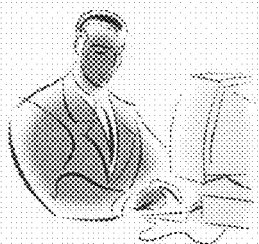
10 System User

1700 A system

1710 Circuitry for accepting input that specifies an individual

1720 Circuitry for accepting input that identifies a first drug therapy associated with the individual 1730 Circuitry for accepting input that identifies a second drug therapy associated with the individual 1740 Circuitry for identifying at least one CYP450-family enzyme that influences metabolism of both the first drug therapy and the second drug therapy 1795 Database 1750 Circuitry for identifying at least one modulator of one or more of the at least one CYP450-family enzyme 1770 Circuitry for communicating one or more treatment to a system user, wherein the treatment includes one or more of the at least one modulator 2600 Circuitry for identifying at least one dietary factor associated with an alteration in activity of at least one of the one or more treatment; and
Circuitry for communicating one or more alternate dosages of the one or more treatment, wherein the one or more alternate dosages are calculated to compensate for the alteration in activity of at least one of the one or more treatment 2610 Circuitry for identifying at least one dietary factor associated with activity of the at least one CYP450-family enzyme; and
Circuitry for communicating at least one dietary mitigation strategy to a system user 2620 Wherein the at least one dietary factor is associated with the individual

COMPUTATIONAL METHODS AND SYSTEMS FOR SUGGESTING MODULATORS OF CYP450 AS TREATMENT OPTIONS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

Related Applications:

For purposes of the USPTO extra-statutory requirements, the present application constitutes a continuation-in-part of U.S. patent application Ser. No. 12/319,153, entitled COMPUTATIONAL METHODS AND SYSTEMS FOR TREATMENT IN RELATION TO MODULATION OF CYP450 ENZYME ACTIVITY, naming Mahalaxmi Gita Bangera, Roderick A. Hyde, Muriel Y. Ishikawa, Elizabeth A. Sweeney, Lowell L. Wood, Jr., and Victoria Y. H. Wood as inventors, filed Dec. 30, 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

In one aspect, a method includes but is not limited to: accepting input that specifies an individual; accepting input that identifies a drug therapy associated with the individual; identifying at least one first CYP450-family enzyme that influences metabolism of the drug therapy associated with the individual; identifying at least one second CYP450-family enzyme that influences metabolism of the drug therapy associated with the individual; identifying at least one modulator of one or more of the at least one first CYP450-family enzyme; identifying at least one modulator of one or more of the at least one second CYP450-family enzyme; and invoking circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme.

In one aspect, a method includes but is not limited to: accepting input that specifies an individual; accepting input that identifies a first drug therapy associated with the individual; accepting input that identifies a second drug therapy associated with the individual; identifying at least one CYP450-family enzyme that influences metabolism of both the first drug therapy and the second drug therapy; identifying at least one modulator of one or more of the at least one CYP450-family enzyme; and invoking circuitry for communicating one or more treatment to a system user, wherein the one or more treatment includes one or more of the identified at least one modulator.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to: circuitry for accepting input that specifies an individual; circuitry for accepting input that identifies a drug therapy associated with the individual; circuitry for identifying at least one first CYP450-family enzyme that influences metabolism of the drug therapy associated with the individual; circuitry for identifying at least one second CYP450-family enzyme that influences metabolism of the drug therapy associated with the individual; circuitry for identifying at least one modulator of one or more of the at least one first CYP450-family enzyme; circuitry for identifying at least one modulator of one or more of the at least one second CYP450-family enzyme; and circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme.

In one aspect, a system includes but is not limited to: circuitry for accepting input that specifies an individual; circuitry for accepting input that identifies a drug therapy associated with the individual; circuitry for identifying at least one first CYP450-family enzyme that influences metabolism of the drug therapy associated with the individual; circuitry for identifying at least one second CYP450-family enzyme that influences metabolism of the drug therapy associated with the individual; circuitry for identifying at least one modulator of one or more of the at least one first CYP450-family enzyme; circuitry for identifying at least one modulator of one or more of the at least one second CYP450-family enzyme; and circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme.

The foregoing summary is illustrative only and is not intended to be in any way limiting. In addition to the illustrative aspects, embodiments, and features described above, further aspects, embodiments, and features will become apparent by reference to the drawings and the following detailed description. In addition to the foregoing, various other method and/or system and/or program product aspects are set forth and described in the teachings such as text (e.g., claims and/or detailed description) and/or drawings of the present disclosure.

BRIEF DESCRIPTION OF THE FIGURES

FIG. 2 is a diagram illustrating some aspects of a system such as the one depicted in FIG. 1.
FIG. 3 is a diagram showing some aspects of a system such as the one depicted in FIG. 1.
FIG. 4 is a diagram illustrating some aspects of a system such as the one depicted in FIG. 1.
FIG. 5 is a diagram showing some aspects of a system such as the one depicted in FIG. 1.
FIG. 6 is a diagram illustrating some aspects of a system such as the one depicted in FIG. 1.
FIG. 7 is a diagram showing some aspects of a system such as the one depicted in FIG. 1.
FIG. 8 is a diagram illustrating some aspects of a system such as the one depicted in FIG. 1.
FIG. 9 is a diagram showing some aspects of a system such as the one depicted in FIG. 1.
FIG. 10 is a diagram illustrating some aspects of a system such as the one depicted in FIG. 1.
FIG. 11 is a diagram showing some aspects of a system such as the one depicted in FIG. 1.
FIG. 12 is a diagram illustrating some aspects of a system such as the one depicted in FIG. 1.
FIG. 13 is a diagram showing some aspects of a system such as the one depicted in FIG. 1.
FIG. 14 is a diagram illustrating some aspects of a system such as the one depicted in FIG. 1.
FIG. 15 is a diagram showing some aspects of a system such as the one depicted in FIG. 1.
FIG. 16 is a diagram showing some aspects of a system such as the one depicted in FIG. 1.
FIG. 17 is a diagram illustrating some aspects of a system.
FIG. 18 is a diagram showing some aspects of a system such as the one depicted in FIG. 17.
FIG. 19 is a diagram illustrating some aspects of a system such as the one depicted in FIG. 17.
FIG. 20 is a diagram showing some aspects of a system such as the one depicted in FIG. 17.
FIG. 21 is a diagram illustrating some aspects of a system such as the one depicted in FIG. 17.
FIG. 22 is a diagram showing some aspects of a system such as the one depicted in FIG. 17.
FIG. 23 is a diagram illustrating some aspects of a system such as the one depicted in FIG. 17.
FIG. 24 is a diagram showing some aspects of a system such as the one depicted in FIG. 17.
FIG. 25 is a diagram illustrating some aspects of a system such as the one depicted in FIG. 17.
FIG. 26 is a diagram showing some aspects of a system such as the one depicted in FIG. 17.

The use of the same symbols in different drawings typically indicates similar or identical items.

DETAILED DESCRIPTION

Figure 1:
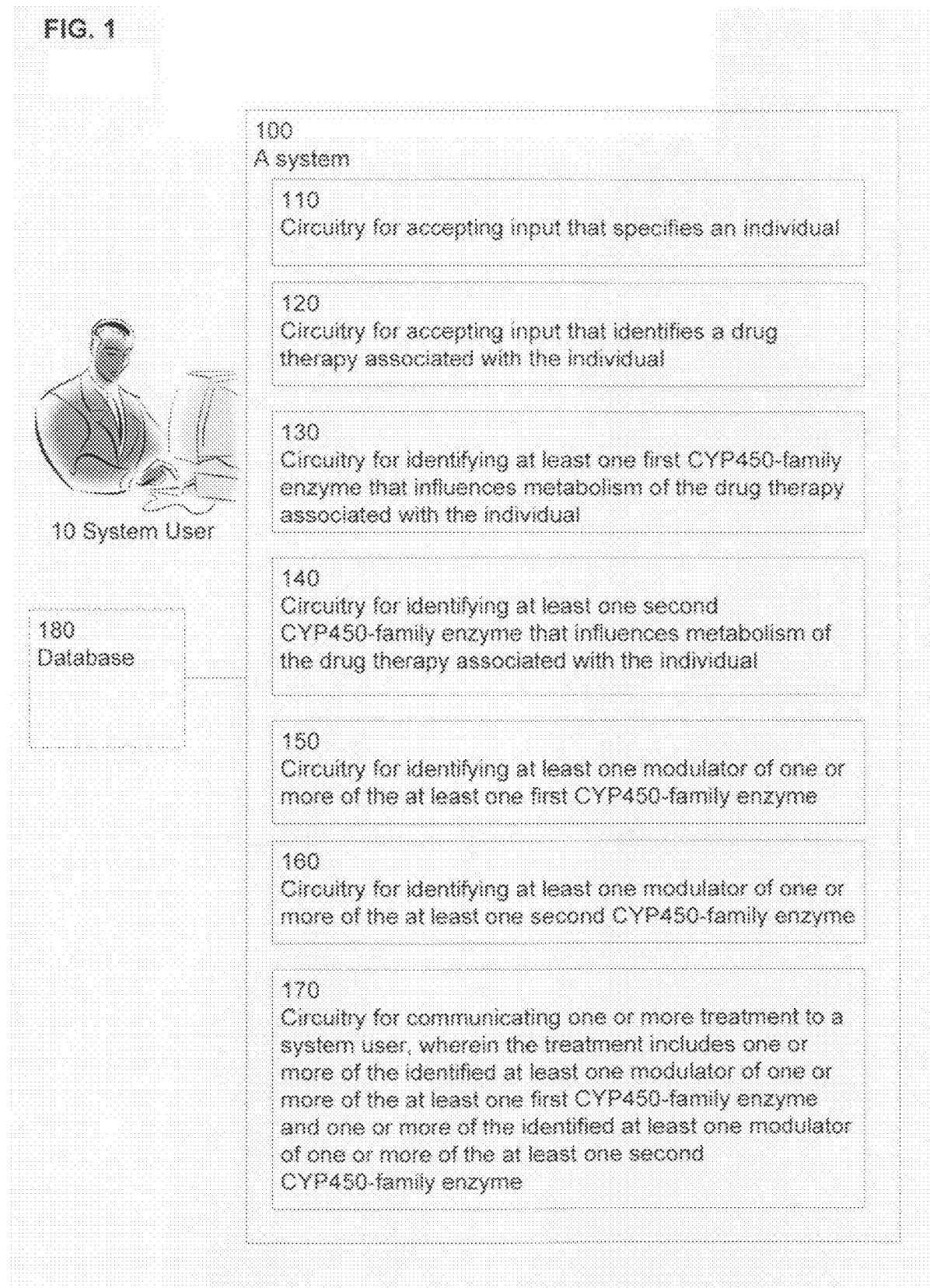
FIG. 1 is a diagram showing some aspects of a system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 depicts some aspects of a system including circuitry. A system 100 may include: circuitry for accepting input that specifies an individual 110; circuitry for accepting input that identifies a drug therapy associated with the individual 120; circuitry for identifying at least one first CYP450-family enzyme that influences metabolism of the drug therapy associated with the individual 130; circuitry for identifying at least one second CYP450-family enzyme that influences metabolism of the drug therapy associated with the individual 140; circuitry for identifying at least one modulator of one or more of the at least one first CYP450-family enzyme 150; circuitry for identifying at least one modulator of one or more of the at least one second CYP450-family enzyme 160; and circuitry for communicating one or more treatment to a system user, wherein the treatment includes one or more of the identified at least one modulator of one or more of the at least one first CYP450-family enzyme and one or more of the identified at least one modulator of the at least one second CYP450-family enzyme 170. The system 100 may include or may be connected to at least one database, such as that depicted as database 180. A database may be a publicly-available, privately-available, or a limited-access database, and may include, for example, information regarding: CYP450-family enzymes, genes and variants; metabolic pathways that include or are influenced by CYP450-family enzymes; drug therapies; modulators of CYP450-family enzymes and variants; treatments, including those that contain at least one modulator of a CYP450-family enzyme; population-based data regarding individuals, CYP450-family variants, or environmental exposures; dosage schedules; dietary factors; and specific data regarding individuals. A system 100 may accept input and communicate with a system user 10. Depending on the embodiment, a system may be implemented by circuitry or a computing device.

A system may include at least one computer program for use with at least one computer system and wherein the computer program includes a plurality of instructions including but not limited to: one or more instructions for accepting input that specifies an individual; one or more instructions for accepting input that identifies a drug therapy associated with the individual; one or more instructions for identifying at least one first CYP450-family enzyme that influences metabolism of the drug therapy associated with the individual; one or more instructions for identifying at least one second CYP450-family enzyme that influences metabolism of the drug therapy associated with the individual; one or more instructions for identifying at least one modulator of one or more of the at least one first CYP450-family enzyme; one or more instructions for identifying at least one modulator of one or more of the at least one second CYP450-family enzyme; and one or more instructions for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme.

A system may include at least one computer program for use with at least one computer system and wherein the computer program includes a plurality of instructions including but not limited to: one or more instructions for accepting input that specifies an individual; one or more instructions for accepting input that identifies a first drug therapy associated with the individual; one or more instructions for accepting input that identifies a second drug therapy associated with the individual; one or more instructions for identifying at least one CYP450-family enzyme that influences metabolism of both the first drug therapy and the second drug therapy; one or more instructions for identifying at least one modulator of one or more of the at least one CYP450-family enzyme; and one or more instructions for communicating one or more treatment to a system user, wherein the one or more treatment includes one or more of the at least one modulator.

A system, such as systems 100 and 1700, may be connected to a user interface and communicate with a system user, such as system user 10. A user interface may include visual interfaces such as monitors or display devices, may include audio devices that communicate through sound or vibration, may include tactile interfaces, or may include some combination of types of user interfaces. A user interface may be used by the system user to input information or data into the system. For example, the user interface may include one or more: keyboards; sound receivers; computer mouses; "dropdown" menu options; or touchpads. A user interface may be used to communicate information from the system to the user. For example, a user interface may include one or more of: sound transmitters; optical transmitters; monitors; or visual interaction interfaces. A system user may include medical personnel such as a physician, nurse, pharmacist or therapist, or may include a medical team. A system user may include researchers, scientists, or medical investigators, such as those involved in, for example, a clinical trial or a research program including human subjects. In some instances a system user may include drug developers, such as drug testing personnel or experimental pharmacists. In some instances, a system user may include patients or individuals associated with one or more drug therapies. Although system user 10 is shown herein as a single illustrated figure, system user 10 may be representative of a human user, a robotic user (e.g., computational entity), and/or substantially any combination thereof (e.g., a user may be assisted by one or more robotic agents) unless context dictates otherwise. In general, the same may be said of "sender" and/or other entity-oriented terms as such terms are used herein unless context dictates otherwise.

A system user may communicate input with the system. For example, a system user may type into a keyboard or manipulate preset visual menus via mouse, touchscreen, or other user interface. For example, a system user may make sound or visual cues which are interpreted as input by the user interface. A system user may, for example, send input to communicate with the system. Input may include information that specifies an individual. Input may include information that identifies a drug therapy associated with the individual. Input may include information specifying one or more variant of at least one CYP450-family enzyme that influences metabolism of at least one drug therapy associated with the individual.

A system may communicate with a system user. For example, a system may communicate one or more treatment to a system user. For example, a system may invoke circuitry for communicating one or more treatment to a system user. A system may communicate with a system user through a user interface.

A "drug therapy," as used herein, includes compounds, medicinals, and therapies including drugs which are reasonably expected to produce a physiological effect when administered. A drug therapy may be intended for administration orally, intravenously, through inhalation, transdermally, through a combination of routes, or through other mechanisms as known to those of skill in the art. A drug therapy may include a schedule of dosages, such as daily, weekly, or monthly dosing. A drug therapy may include a schedule of dosages, which may include staggered dosages, dosages at specific time intervals, or dosages in combination with other events (such as meals, test results, or the administration of other drugs). A drug therapy may include one or more active ingredients in combination with fillers, stabilizers, encapsulation materials, diluents, solvents, or other conventional materials. A drug therapy may be associated with the individual in the past, present or a future state. A drug therapy may have been previously administered to the individual, be currently taken by the individual, or proposed for future administration to the individual. A drug therapy may include prescription medication, non-prescription medication, or some combination thereof. A drug therapy may include, for example, diphenhydramine, itraconazole, erythromycin, cimetidine, clarithromycin, diltiazem, nefazodone, mibefradil, cyclosporine, felodipine, nimodipine, nifedipine, amlodipine, nisoldipine, cyclophosphamide, ifosfamide, etoposide, teniposide, tamoxifen, taxol (paclitaxel), vinca alkaloids, tropisetron, odansetron, pravastatin, fluvastatin, atorvastatin, cerivastatin, lovastatin and simvastatin. A drug therapy may include therapy utilizing descarbothoxyloratadine (DHL) dispensed in accordance with the methods described in U.S. Pat. No. 5,731,319 to Aberg, entitled "Methods for treating disorders using descarbothoxyloratadine," which is herein incorporated by reference. In some aspects, a drug therapy may include nutritional supplements such as vitamin or protein supplements, or may include herbal-based therapy. Herbal therapies may include traditional therapies, including Chinese, Indian, or European traditional therapies. In some aspects, a drug therapy may be nutritional or food-based, such as when a food or drink is ingested for its physiological effects. A drug therapy may include, for example, St. John's wort. A drug therapy may be a standard therapy, such as one that may be used as part of therapy for an identified condition as part of the standard of care. A drug therapy may be identified as a potential drug therapy. In some instances, a potential drug therapy may be subject to an additional screening process in addition to the methods and systems described herein. For example, a drug therapy may be screened using the methods described in US Patent Application No. 20040180392 to Prueksaritanont, entitled "Screening and selection methods for statin drug combinations," which is herein incorporated by reference.

A "CYP450-family enzyme," as used herein, may include any of the polypeptides encoded by the cytochrome p-450 family of genes. For example, a CYP450-family enzyme may include polypeptides encoded by one or more of the following genes: CYP1A1, CYP1A2, CYP2C9, CYP2A6, CYP2B6, CYP2C8, CYP2C9, CYP2C19, CYP2D6, CYP2E1, CYP3A4, and CYP3A5. A CYP450-family enzyme may include, for example, the enzyme encoded by the CYP1A1 gene which may be referred to in various contexts as the CYP1A1 protein, or the CYP1A1 enzyme, or cytochrome p450 1A1, or xenobiotic monooxygenase, or aryl hydrocarbon hydroxylase, or flavoprotein-linked monooxygenase, or dioxin-inducible cytochrome P1-450, or cytochrome p450 polypeptide 1 subfamily I (aromatic compound-inducible). For example, CYP450-family enzymes include a group of enzymes which are steroidogenic, as described in: Hanukoglu, Steroidogenic enzymes: structure, function, and role in regulation of steroid hormone biosynthesis. J. Steroid Biochem. Mol. Biol. 43:779-804, 1992, which is herein incorporated by reference.

A CYP450-family enzyme may influence metabolism of a drug therapy either directly or indirectly. For example, a CYP450-family enzyme may influence metabolism of a drug therapy by directly acting as a cofactor in the metabolism of some portion of the drug therapy. For example, a CYP450-family enzyme may influence metabolism of a drug therapy by directly participating in one or more reactions as part of the physiological processing of some portion of the drug therapy. For example, a CYP450-family enzyme may influence metabolism of a drug therapy by indirectly influencing a metabolic pathway that includes the metabolism of some portion of the drug therapy. A drug therapy may be known in the art to be metabolized by a CYP450-family enzyme, such as, for example, alporzolam, celocoxib, erythromycin, haloperidol, lovastatin, paroxetine, quinidine and trazolam (see Kalra, Cytochrome P450 enzyme isoforms and their therapeutic implications: an update, Indian J. Med. Sci. 61: 102-116, 2007; which is herein incorporated by reference). A drug therapy may be identified with a metabolism that may be influenced by a CYP450-family enzyme through computational or predictive methods, such as those described in US Patent Application 20030212497 to Korzekwa, entitled "Relative rates of cytochrome P450 metabolism," which is incorporated by reference herein. A drug therapy may be predicted to be metabolized by one or more CYP450-family enzymes by methods such as those described in U.S. Pat. No. 6,625,547 to Korezkwa, entitled "Relative rates of Cytochrome P450 metabolism," which is herein incorporated by reference.

Some aspects of the systems and methods described herein include identifying at least one modulator of one or more CYP450-family enzyme. A "modulator" of a CYP450-family enzyme, as used herein, includes any compound, material, drug, biologic, chemical, or agent that is predicted or known to act to modulate the activity of at least one CYP450-family enzyme. For example, a modulator of a CYP450-family enzyme may be a compound that is predicted to inhibit the enzymatic activity of the CYP450-family enzyme. For example, a modulator of a CYP450-family enzyme may be a compound that is predicted to cleave the CYP450-family enzyme at one or more sites. For example, a modulator may include a compound predicted to bind to one or more CYP450-family enzymes in a binding assay such as those described in U.S. Pat. No. 6,790,632 to Zweig, entitled "Membrane receptor reagent and assay," which is herein incorporated by reference. For example, a modulator may be a compound that is predicted to enhance the enzymatic activity of the CYP450-family enzyme. For example, a modulator may include a compound that is known or predicted to increase or decrease transcription of at least one CYP450-family gene corresponding to at least one CYP450-family enzyme, and therefore is predicted to result in the increased expression and activity of the CYP450-family enzyme. For example, a modulator may be identified through methods such as those described in U.S. Pat. No. 6,610,489 to Wolffe, entitled "Pharmacogenomics and identification of drug targets by reconstruction of signal transduction pathways based on sequences of accessible regions," which is herein incorporated by reference. For example, a modulator may include a RNAi compound that acts or is predicted to act to limit the available RNA transcribed from a CYP450-family gene and therefore limit the levels of CYP450-family enzyme available for activity. For example, a modulator may include RNAi oligonucleotides as described by Chen et al., or be developed using the methods discussed by Chen et al (Chen et al., Small interfering RNA-mediated silencing of Cytochrome p450 3A4 gene, DMD Fast Forward, published Jun. 7, 2006 as doi: 10.1124/dmd.106.009837, which is herein incorporated by reference).

For example, a modulator may include a snRNA compound that acts or is predicted to act to limit the available RNA transcribed from a CYP450-family gene and therefore limit the levels of CYP450-family enzyme available for activity. For example, a modulator may include an antisense oligonucleotide-containing compound that acts or is predicted to act to limit the available RNA transcribed from a CYP450-family gene and therefore limit the levels of CYP450-family enzyme available for activity. For example, a modulator may include oligomers such as those described in US Patent Application No. 20040229829 to Iversen, entitled "Enzyme inhibitors for metabolic redirection," which is incorporated by reference herein. For example, a modulator may be developed incorporating the methods described in U.S. Pat. Nos. 6,673,778 and 6,686,338 to Iversen, entitled "Enzyme inhibitors for metabolic redirection," which is incorporated by reference herein. For example, a modulator may include at least one double-stranded RNA oligonucleotide such as those described in US Patent Application No. 20050222071 to Duranton, entitled "Topical administrations of at least one double-stranded RNA oligonucleotide (dsRNA)," which is herein incorporated by reference. For example, a modulator may be a compound that is known or predicted to act to increase translation of the RNA transcript from the CYP450-family gene and therefore increase available CYP450-family enzyme. For example, a modulator may include a compound that increases metabolic catalysis of the CYP450-family enzyme, thereby decreasing the bioavailability of the CYP450-family enzyme. For example, a modulator may include a compound that alters metabolic catalysis of the CYP450-family enzyme, thereby increasing or decreasing the bioavailability of the CYP450-family enzyme. A modulator may be directed to a specific anatomic location, such as an organ, region, or area of the body, for example, the small intestine, the large intestine, the stomach, the liver, or the kidneys. For example, a modulator may be delivered into a body within a particle such as those described in US Patent Application Nos. 20040052865 and 20060188562 to Gower, entitled "Materials and methods for drug delivery and uptake," which are herein incorporated by reference. A modulator may include methods and compositions such as those described in US Patent Application No. 20020142950 to Hayward, entitled "Methods for enhancing the bioavailability of a drug," which is incorporated by reference herein. A modulator may be predicted to bind to at least one CYP450-family enzyme, for example using prediction methods such as those described in US Patent Application No. 20030167135 to Ewing, entitled "Non-linear modeling of biological activity of chemical compounds," which is incorporated by reference herein. A modulator may be developed in part through computational methods such as those described in Jenwitheesuk et al., Novel paradigms for drug discovery: computational multitarget screening, Trends in Pharmacological Sciences 29(2), 62-71, 2008, which is herein incorporated by reference.

In some aspects, a system includes circuitry for communicating one or more treatment to a system user. A "treatment," as used herein, may include a therapy, medicinal, plan of action, dosage schedule, course of treatment or a combination thereof which is reasonably expected to mitigate a medical situation experienced by the individual. In some aspects, a treatment may include a known drug treatment, including pharmaceutical treatments, herbal remedies, traditional therapy (such as traditional Chinese, Indian, or European remedies) or a combination thereof. In some aspects, a treatment may be directed to a known medical situation or it may be directed to a nonapparent, hypothetical, predicted or supposed medical situation. In some aspects, a treatment may include a negative suggestion (e.g. "do not consume grapefruit, or starfruit, containing products"). In some aspects, a treatment may include a positive suggestion (e.g. include a goal to keep BMI in target range). A treatment may include one or more of the identified at least one modulator of one or more of the at least one first CYP450-family enzyme and one or more of the identified at least one modulator of one or more of the at least one second CYP450-family enzyme. For example, a treatment may include a compound that includes both one or more of the identified at least one modulator of one or more of the at least one first CYP450-family enzyme and one or more of the identified at least one modulator of one or more of the at least one second CYP450-family enzyme in the same intended dosage or administration. For example, a treatment may include one or more of the identified at least one modulator of one or more of the at least one first CYP450-family enzyme and one or more of the identified at least one modulator of one or more of the at least one second CYP450-family enzyme in distinct dosages or administrations, including via different modes of administration (e.g. oral and intravenous). A treatment may include aspects or compositions targeted for delivery in certain regions or to certain tissues. A treatment may be delivered through targeted delivery or particle-based delivery, such as those described in US Patent Application No. 20020142950 to Hayward, entitled "Methods for enhancing the bioavailability of a drug," which is incorporated by reference herein. A treatment may include topical administration, for example as described in U.S. Pat. No. 5,658,881 to Gelland, entitled "Method for topical inhibition of the metabolic activity of Cytochrome P450," which is herein incorporated by reference. A treatment may be further refined with methods such as those described in U.S. Pat. No. 6,037,157 to Norbeck, entitled "Method for improving pharmacokinetics," which is herein incorporated by reference. A treatment may be one or more treatments such as those described in U.S. Pat. No. 7,208,600 to Cottrell, entitled "Inhibitors of serine proteases, particularly HCV NS3-NS4A proteases," which is herein incorporated by reference. A treatment may be one or more treatments such as those described in U.S. Pat. No. 7,378,422 to Perni, entitled "Inhibitors of serine proteases, particularly HCV NS3-NS4A protease," which is herein incorporated by reference.

In some embodiments, an individual may be a generic or population-based individual and one or more treatments may be developed in advance, and stored until such time as they become needful for one or more patients in a given situation.

In some embodiments, treatments may include one or more drugs packaged or sorted in such a manner as to facilitate suggested dosages or dosage schedules such as those developed by methods and systems disclosed herein. For example, a treatment may be: dispensed or packaged in a manner to facilitate daily, weekly, or monthly dosages; or packaged or dispensed in combinations and composition amounts for each administration.

In some embodiments, systems and methods such as those described herein may be used in conjunction with methods for assessing disease susceptibility associated with dietary and lifestyle risk factors, such as those described in US Patent Application Nos. 20030023387 and 20060178837 to Gill-Garrison entitled "Computer-assisted means for assessing lifestyle risk factors," which are incorporated by reference herein.

In some embodiments, systems and methods such as those described herein may be used in conjunction with methods to optimize drug selection, such as those described in US Patent Application 20060253263 to Meshkin, entitled "Method to optimize drug selection, dosing and evaluation and to help predict therapeutic response and toxicity from immunosuppressant therapy," which is herein incorporated by reference.

In some embodiments, systems and methods such as those described herein may be used in conjunction with information methods and systems for generating data for optimizing a medical treatment, such as those described in US Patent Application No. 20060289019 to Marchand, entitled "Information method and system for generating data for optimizing a medical treatment, and equipment used in this system," which is herein incorporated by reference.

In some embodiments, systems and methods such as those described herein may be used in conjunction with methods for selecting medications, such as those described in US Patent Application No. 20070003931 to Mrazek, entitled "Methods for selecting medications," which is herein incorporated by reference.

With reference now to FIG. 2, a system 100 may include circuitry for accepting input that specifies an individual 110. In some aspects, a system 100 may include circuitry for accepting input that specifies an individual 110 wherein the individual is a representative individual 200. In some aspects, an individual may be a specific identified person or entity, such as an individual person identified by name (e.g. Jane Doe) or identification number (e.g. 12345). In some aspects, an individual may be a representative individual. For example, the individual may be a composite, median, average or hypothetical individual. For example, the individual may include representative characteristics from a population, cohort or group and represent aspects of the group. For example, the individual may be specified generally by age, gender, race, body mass, disease state, health status or other physiological condition. For example, the individual may be identified as a 55 year old African-American male with a history of heart disease. For example, the individual may be identified as a 35 year old Caucasian woman with type I diabetes who smokes. For example, the individual may be identified as a 45 year old Asian man with a BMI of 30 and asthma. For example, the individual may be identified as a woman of mixed racial ancestry in her sixth decade and no known substantial medical history. In some aspects, an individual may be specified by their relationship to another person, such as, for example, "mother of patient XYZ" or "brother of individual with heart disease." An individual may be specified by their inclusion in a specific ethnic, population or family group, such as, for example, "African-American," "first-degree relative of patient VPR" or "predominately of German descent."

With reference now to FIGS. 2 and 3, a system 100 may include circuitry for accepting input that identifies a drug therapy associated with the individual 120. In some aspects, a system 100 may include circuitry for accepting input that identifies a drug therapy associated with the individual 120 wherein the drug therapy includes a statin therapy 210. For example, the statin therapy may include atorvastatin, cerivastatin, lovastatin, fluvastatin, cerivastatin, pravastatin, and simvastatin. In some aspects, a system 100 may include circuitry for accepting input that identifies a drug therapy associated with the individual 120 wherein the drug therapy includes an acetaminophen therapy 220. For example, the acetaminophen therapy may include acetaminophen administered as a distinct drug therapy, or may include acetaminophen administered in combination with one or more other drugs. For example, the acetaminophen therapy may include compounds such as those containing acetaminophen in combination with opioids such as codeine and dihydrocodeine. For example, the acetaminophen therapy may include compounds such as those containing acetaminophen in combination with at least one of: propoxyphene napsylate; doxylamine succinate; butalbital; and caffeine. In some aspects, a system 100 may include circuitry for accepting input that identifies a drug therapy associated with the individual 120 wherein the drug therapy includes a cancer chemotherapy 230. For example, a cancer chemotherapy may include cyclophosphamide, ifosfamide, etoposide, teniposide, tamoxifen, taxol (paclitaxel) and vinca alkaloids. A cancer chemotherapy may include heterocyclic compound-based therapy, such as those described in US Patent Application No. 20050049294 to Palladino, entitled "Methods of using [3.2.0]heterocyclic compounds and analogs thereof," which is herein incorporated by reference. In some aspects, a system 100 may include circuitry for accepting input that identifies a drug therapy associated with the individual 120 wherein the drug therapy includes a hormone-related therapy 300. For example, a hormone-related therapy may include hormone-related therapy may include therapy to modulate levels of a steroid hormone.

Examples of steroid hormones or related compounds used as part of a therapy may include, but are not limited to, natural and synthetic compounds, metabolites, modulators, or analogs thereof. Therapies that may be used to alter estrogen levels, for example, may include but are not limited to natural compounds with estrogenic activity such as estradiol (estradiol-17β), estriol, estrone, and their metabolites; synthetic steroidal compounds having estrogenic activity such as estradiol 17β-acetate, estradiol 17β-cypionate, estradiol 17β-propionate, estradiol 3-benzoate, ethinyl estradiol, piperazine estrone sulfate, mestranol, and quinestrol; synthetic non-steroidal compounds having estrogenic activity such as diethylstilbestrol, chlorotrianisene, and methallenestril; and plant derived phytoestrogens. Esters, conjugates and prodrugs of suitable estrogens may also be used. In some instances, a combination of estrogens may be used, see e.g. U.S. Pat. No. 6,911,438, which is incorporated herein by reference, which provides a combination of three estrogens 2-hydroxyestrone, 17-β estradiol, and estriol, for example in a ratio. In some instances, steroid hormone levels may be altered by providing a natural precursor such as, for example, testosterone, which may be converted in vivo to estradiol, or androstenedione, which may be convered to estrone or may be convered to testosterone.

Therapies that may be used to alter progesterone levels, for example, include but are not limited to natural and synthetic compounds having progestational activity, such as, for example, progesterone, levonorgestrel, norethindrone, norethindrone acetate, desogestrel, gestodene, dienogest, norgestimate, cyproterone acetate, norelgestromin, etonogestrel, ethynodiol diacetate, norgestrel, trimegestone, medroxyprogesterone acetate, chlormadinone acetate, drospirenone, and other natural and/or synthetic gestagens. Esters, conjugates, and prodrugs of suitable progestins may also be used. Additional compounds include metabolites and/or analogs of progesterone. Therapies that may be used as part of a treatment regimen to alter testosterone and androgen levels, for example, include but are not limited to natural androgens and metabolites thereof such as testosterone, dihydrotestosterone (DHT), dehydroepiandrosterone (DHEA), dehydroepiandrosterone sulfate (DHEAS), androstenedione, androst-5-ene-3β,17β-diol; synthetic androgens such as testosterone undecanoate, testosterone propionate, testosterone cypionate, testosterone enanthate, methyltestosterone, fluoxymesterone, oxymetholone, oxandrolone, nandrolone decanoate.

A treatment regimen to alter levels of one or more hormones may include compounds that stimulate the synthesis of one or more hormones. Such compounds may include gonadotropin hormones such as, for example, luteinizing hormone (LH) and follicle stimulating hormone (FSH), which modulate testosterone, estrogen and progesterone levels during the menstrual cycle. Examples of purified follicle stimulating hormone include but are not limited to urofollitropin (uFSH), recombinant forms of follicle stimulating hormone (rFSH) follitropin alfa and follitropin β. Examples of luteinizing hormone include recombinant human luteinizing hormone (rLH) lutropin.

In some instances, steroid hormone levels may be altered by providing a therapy with enzymatic activity able to convert a naturally occurring precursor so as to alter a hormone level, for example a CYP450-family enzyme, or analog or modulator thereof. The treatment regimen might include modulating the activity of a resident enzyme, such as one active in steroidogenesis, by adding an inhibitor or activator.

A system 100 may include circuitry for identifying at least one first CYP450-family enzyme that influences metabolism of the drug therapy associated with the individual 130. In some aspects, circuitry for identifying at least one first CYP450-family enzyme that influences metabolism of the drug therapy associated with the individual 130 may include circuitry wherein the at least one first CYP450-family enzyme that influences metabolism of the drug therapy influences metabolism directly 310. In some aspects, circuitry for identifying at least one first CYP450-family enzyme that influences metabolism of the drug therapy associated with the individual may include circuitry wherein the at least one first CYP450-family enzyme that influences metabolism of the drug therapy influences metabolism indirectly. A system 100 may include circuitry for identifying at least one second CYP450-family enzyme that influences metabolism of the drug therapy associated with the individual 140. In some aspects, circuitry for identifying at least one second CYP450-family enzyme that influences metabolism of the drug therapy associated with the individual 140 may include circuitry wherein the at least one second CYP450-family enzyme that influences metabolism of the drug therapy influences metabolism directly 320. In some aspects, circuitry for identifying at least one second CYP450-family enzyme that influences metabolism of the drug therapy associated with the individual may include circuitry wherein the at least one second CYP450-family enzyme that influences metabolism of the drug therapy influences metabolism indirectly. The at least one CYP450-family enzyme that influences metabolism of the drug therapy associated with the individual may be known or predicted to influence metabolism of the drug therapy associated with the individual. The at least one CYP450-family enzyme that influences metabolism of the drug therapy may influence metabolism through directly metabolizing all or some component of the drug therapy or it may influence metabolism of the drug therapy indirectly through an effect on a metabolic pathway. The at least one CYP450-family enzyme that influences metabolism of the drug therapy may influence metabolism directly, such as through acting directly on some component of the drug therapy or acting in concert with other biological factors on the metabolism of some component of the drug therapy.

With reference now to FIGS. 4 and 5, in some aspects a system 100 includes circuitry for identifying at least one modulator of one or more of the at least one first CYP450-family enzyme 150, which may include wherein the at least one modulator of one or more of the at least one first CYP450-family enzyme is an endogenous modulator 400. In some aspects a system 100 includes circuitry for identifying at least one modulator of one or more of the at least one second CYP450-family enzyme 160, which may include wherein the at least one modulator of one or more of the at least one second CYP450-family enzyme is an endogenous modulator 420. An "endogenous modulator," as used herein, includes a modulator that includes components that are endogenous to the individual, such as endogenous proteins, polypeptides, RNA species, or signaling molecules. In some aspects a system 100 includes circuitry for identifying at least one modulator of one or more of the at least one first CYP450-family enzyme 150, which may include wherein the at least one modulator of one or more of the at least one first CYP450-family enzyme is an exogenous modulator 410. In some aspects a system 100 includes circuitry for identifying at least one modulator of one or more of the at least one second CYP450-family enzyme 160, which may include wherein the at least one modulator of one or more of the at least one second CYP450-family enzyme is an exogenous modulator 430. An "exogenous modulator," as used herein, includes a modulator that includes components that are exogenous to the individual, such as, for example, externally-derived drugs, xenobiotics, compounds, active ingredients or materials. In some aspects, an exogenous modulator may be derived from a biological source, such as a protein or polypeptide that is purified from biological materials. In some aspects a system 100 includes circuitry for identifying at least one modulator of one or more of the at least one first CYP450-family enzyme 150, which may include wherein the at least one modulator of one or more of the at least one first CYP450-family enzyme is a synthetic modulator 500. In some aspects a system 100 includes circuitry for identifying at least one modulator of one or more of the at least one second CYP450-family enzyme 160, which may include wherein the at least one modulator of one or more of the at least one second CYP450-family enzyme is a synthetic modulator 510. As used herein a "synthetic modulator" includes a compound or component which is entirely or substantially synthetic, such as, for example, a chemical compound which is laboratory-derived or chemically created.

As illustrated in FIG. 6, a system may include: circuitry for suggesting one or more dosages of the one or more treatment to a system user; circuitry for identifying at least one environmental factor associated with an alteration in activity of at least one of the one or more treatment; and circuitry for communicating one or more alternate dosages of the one or more treatment to a system user, wherein the one or more alternate dosages are calculated to compensate for the alteration in activity of at least one of the one or more treatment 600. For example, at least one environmental factor may include pollutants, carcinogens, food additives, or gases. For example, at least one environmental factor may include exposure to sunlight or UV light. Environmental factors such as exposure to sunlight or UV light may influence an individual's vitamin D levels or be relevant to interactions with drug therapies that increase an individual's photosensitivity. One or more of the at least one environmental factor may include factors that are predicted to be internalized by an individual, such as, for example, factors that may be ingested, absorbed transdermally, or inhaled. For example, at least one environmental factor may include carbon tetrachloride, halothane, or isoflurane. In some instances, the at least one environmental factor may be associated with reduced activity of at least one of the one or more treatment, whereas in other instances the at least one environmental factor may be associated with increased activity of at least one of the one or more treatment. In some instances, there may be a plurality of environmental factors which in combination are associated with an alteration in activity of at least one of the one or more treatment. In some instances, the at least one environmental factor may be known to influence the activity of at least one of the one or more treatment, while in other instances the at least one environmental factor may be predicted or theorized to influence the activity of at least one of the one or more treatment. In some embodiments, the at least one environmental factor may be directly associated with the alteration in activity, such as when some component of the environmental factor directly influences or modulates the treatment. In some embodiments, the at least one environmental factor may be indirectly associated with the alteration in activity, such as when some component of the environmental factor indirectly effects metabolism or activity of the one or more treatment.

As illustrated in FIG. 7, in some embodiments a system 100 may include circuitry for suggesting one or more dosages of the one or more treatment to a system user; circuitry for identifying at least one dietary factor associated with an alteration in activity of at least one of the one or more treatment; and circuitry for communicating one or more alternate dosages of the one or more treatment to a system user, wherein the one or more alternate dosages are calculated to compensate for the alteration in activity of at least one of the one or more treatment 700. A dietary factor may include known, suspected, hypothesized or predicted factors. A dietary factor may include food components, food additives, beverage components, beverage additives, pathogens, contaminants, and packaging material. A dietary factor may include, for example, pomegranate, star fruit or grapefruit, or ingestible materials containing derivatives thereof.

As depicted in FIG. 8, in some embodiments a system 100 may include circuitry for suggesting one or more dosage schedules of the one or more treatment to a system user; circuitry for identifying at least one environmental factor associated with an alteration in activity of at least one of the one or more treatment; and circuitry for communicating one or more alternate dosage schedules of the one or more treatment to a system user, wherein the one or more alternate dosage schedules are calculated to compensate for the alteration in activity of at least one of the one or more treatment 800. A dosage schedule may include, for example, timing of dosages, such as hourly, periodically, daily, weekly or monthly schedules. A dosage schedule may include, for example, content of dosages, such as a quantity or amount in each dosage. A dosage schedule may include, for example, dosages in relation to other events, such as test results, meal timing, food ingested, beverages ingested, or other medications administered.

As shown in FIG. 9, in some embodiments a system 100 may include circuitry for suggesting one or more dosage schedules of the one or more treatment to a system user; circuitry for identifying at least one dietary factor associated with an alteration in activity of at least one of the one or more treatment; and circuitry for communicating one or more alternate dosage schedules of the one or more treatment to a system user, wherein the one or more alternate dosage schedules are calculated to compensate for the alteration in activity of at least one of the one or more treatment 900. A dietary factor may include, for example, known, suspected, hypothesized or predicted factors. A dietary factor may include, for example, food components, food additives, beverage components, beverage additives, pathogens, contaminants, and packaging material. A dietary factor may include, for example, pomegranate, star fruit or grapefruit, or ingestible materials containing derivatives thereof.

As illustrated in FIG. 10, in some embodiments a system 100 may include circuitry for accepting input specifying one or more variant of at least one CYP450-family enzyme that influences metabolism of the drug therapy associated with the individual; circuitry for identifying at least one modulator of at least one of the one or more variant; and circuitry for communicating one or more treatment to a system user, wherein the treatment includes the identified at least one modulator of at least one of the one or more variant 1000. In some embodiments a system 100 with circuitry 1000 may include circuitry wherein the one or more variant of at least one CYP450-family enzyme is directly associated with the individual 1010.

One or more variant of at least one CYP450-family enzyme may include, for example, one or more polymorphisms in the gene encoding the CYP450-family enzyme, such as, for example, single nucleotide polymorphisms (SNPs), insertions, deletions, repeat number polymorphisms, or segment polymorphisms. One or more variant of at least one CYP450-family enzyme may include, for example, one or more variants in the amino acid sequence encoding the CYP450-family enzyme. One or more variant of at least one CYP450-family enzyme may include, for example, one or more variants in the quantity, activity or stability of the at least one CYP450-family enzyme. In some embodiments, the one or more variant of at least one CYP450-family enzyme is directly associated with the individual. In some embodiments, the one or more variant of at least one CYP450-family enzyme is indirectly associated with the individual. The one or more variant of at least one CYP450-family enzyme may be directly associated with the individual, for example, by being a known variant encoded that individual's genome, such as a polymorphism in a gene encoding the CYP450-family enzyme. See, for example, abstracts of the Personalized Medicine Europe: Health Genes and Society meeting held Jun. 19-21, 2005 at Tel-Aviv University, Israel, published in Personalized Medicine, 2(2) 143-184 (2005), which are incorporated by reference herein. See, for example, Kirchheiner, The CYP2C9 polymorphism from enzyme kinetics towards a genotype-adjusted drug therapy, abstracts of the Personalized Medicine Europe: Health Genes and Society, as above, page 157, which is incorporated by reference herein.

Input specifying one or more variant of at least one CYP450-family enzyme or gene may be derived from information generated in an assay. For example, information regarding at least one CYP450-family gene may be generated from the AmpliChip Assay (AmpliChip CYP Test Package Insert (10/2007), Roche Molecular Systems, Inc., Pleasanton, Calif., which is herein incorporated by reference). For example, methods and assays such as those described in US Patent Application No. 20040241714 to Branch, entitled "Methods of assessment of drug metabolizing enzymes," which is herein incorporated by reference, may generate information from which input that associates an individual with one or more variant of a CYP450-family gene or enzyme is derived. For example, information which associates an individual with variant activity of the CYP450-family enzyme CYP2D6 may be generated by method and compositions such as those described in US Patent Application No. 20070026480 to Modak, entitled "Method and composition to evaluate Cytochrome P450 2D6 isoenzyme activity using a breath test," which is herein incorporated by reference. For example, information that may be associated with an individual relating to a variant CYP450-family enzyme may be generated by methods and compositions such as those described in US Patent Application No. 20080085240 to Flockhart, entitled "Method and composition to evaluate Cytochrome P450 2C19 isoenzyme activity using a breath test," which is herein incorporated by reference. For example, information that associates an individual with a CYP450-family gene variant may be generated with assays and methods such as those described in U.S. Pat. No. 7,179,597 to Woosley, entitled "Genetic diagnosis for QT prolongation related adverse drug reactions," which is incorporated by reference herein.

As depicted in FIG. 11, in some embodiments a system 100 includes: circuitry for accepting input specifying one or more variant of at least one CYP450-family gene that influences metabolism of the drug therapy associated with the individual; circuitry for identifying at least one modulator of at least one of the one or more variant of at least one CYP450-family gene; and circuitry for communicating one or more treatment to a system user, wherein the treatment includes the identified at least one modulator of at least one of the one or more variant of at least one CYP450-family gene 1100. Some embodiments of a system 100 may include circuitry wherein the one or more variant of at least one CYP450-family gene is directly associated with the individual 1110. Some embodiments of a system 100 may include circuitry wherein the one or more variant of at least one CYP450-family gene is indirectly associated with the individual.

As illustrated in FIG. 12, in some embodiments a system 100 includes: circuitry for accepting input specifying one or more variant of the at least one first CYP450-family enzyme that influences metabolism of the drug therapy associated with the individual; circuitry for accepting input specifying one or more variant of the at least one second CYP450-family enzyme that influences metabolism of the drug therapy associated with the individual; circuitry for identifying at least one modulator of the one or more variant of the at least one first CYP450-family enzyme; circuitry for identifying at least one modulator of the one or more variant of the at least one second CYP450-family enzyme; and circuitry for communicating one or more treatment to a system user, wherein the treatment includes the identified at least one modulator of the one or more variant of the at least one first CYP450-family enzyme and the identified at least one modulator of the one or more variant of the at least one second CYP450-family enzyme 1200.

As shown in FIG. 13, in some embodiments a system 100 includes circuitry for communicating at least one modulator of one or more of the at least one first CYP450-family enzyme to a system user 1300. In some embodiments, a system 100 includes circuitry for communicating at least one modulator of one or more of the at least one second CYP450-family enzyme to a system user 1310. In some embodiments, a system 100 includes circuitry for identifying one or more treatments including at least one identified at least one modulator of one or more of the at least one first CYP450-family enzyme and at least one identified at least one modulator of one or more of the at least one second CYP450-family enzyme 1320.

As depicted in FIG. 14, in some embodiments a system 100 includes circuitry for identifying at least one environmental factor associated with activity of at least one CYP450-family enzyme that influences metabolism of the drug therapy associated with the individual; and circuitry for communicating at least one environmental mitigation strategy to a system user 1400. In some embodiments circuitry 1400 includes circuitry wherein the at least one environmental factor is associated with the individual 1410. An environmental mitigation strategy may include, for example, suggestions to decrease exposure to an environmental factor, such as a suggestion to decrease exposure to a chemical present in the environment. An environmental mitigation strategy may include, for example, suggestions to increase exposure to an environmental factor, such as a suggestion to increase exposure to fresh air, or to drink extra water. In some embodiments, the at least one environmental factor is associated with the individual.

For example, the environmental exposure may be directly associated with the individual, such as when data indicates that the individual is, has been, or may be directly exposed to the environmental factor. For example, a system user may input information into the system associating an individual with past exposure to an environmental factor. For example, a system may directly associate an individual with exposure to an environmental factor through association with some aspect of information available regarding the individual, such as home address, work address, mode of travel, work history or profession, when the aspect of information available regarding the individual is directly associated with the environmental factor. For example, a particular work site may be known to be contaminated with an industrial solvent, or a particular profession may be known to be associated with exposure to outside air. For example, the environmental exposure may be indirectly associated with the individual, such as when data indicates that the individual has the potential to be or have been exposed to the environmental factor. For example, a system user may input information into the system associating an individual with symptoms or characteristics indicating potential past exposure to an environmental factor. For example, a system may indirectly associate an individual with exposure to an environmental factor through association with some aspect of information available regarding the individual, such as general assumptions or unsubstantiated information regarding environmental factors that may be present in the individual's home address, work address, mode of travel, work history or profession.

FIG. 15 illustrates some embodiments of a system 100. In some embodiments, a system 100 may include circuitry for identifying at least one dietary factor associated with activity of at least one CYP450-family enzyme that influences metabolism of the drug therapy associated with the individual; and circuitry for communicating at least one dietary mitigation strategy to a system user 1500. In some embodiments, circuitry 1500 may include circuitry wherein the at least one dietary factor is associated with the individual 1510. For example, a dietary factor may include a known food or beverage component, additive, pathogen or contaminant. In some instances, a dietary factor may have a temporal component, such as when it has an associated frequency of an event (e.g. "eats pork no more often than once a week" or "drinks coffee daily"). A dietary factor may be directly associated with the individual, such as, for example, when a system user has inputted information into the system indicating that the individual consumes or does not consume a certain food or beverage (e.g. "eats red meat" or "drinks grapefruit juice" or "does not drink milk"). A dietary factor may be indirectly associated with the individual, such as, for example, when a system user has inputted information into the system indicating that the individual belongs to a group or class which is generally associated with particular dietary factors (e.g. "individual is a vegetarian" may indirectly be associated with exposure to vegetables and not exposure to red meat or "individual has allergy to peanuts" may indirectly be associated with reduced exposure to peanut-containing products, including foods cooked with peanut oil.)

In some embodiments, a system 100 may include circuitry for identifying at least one environmental factor associated with activity of at least one CYP450-family enzyme that influences metabolism of the drug therapy associated with the individual, circuitry for requesting information regarding one or more of the at least one environmental factor in relation to the individual, and circuitry for communicating at least one environmental mitigation strategy to a system user 1520. For example, exposure to sunlight may be associated with vitamin D levels and therefore activity of at least one CYP450-family enzyme that is influenced by metabolic vitamin D levels. For example, exposure to tobacco products, such as tobacco smoke, may influence the activity of at least one CYP450-family enzyme in an individual.

FIG. 16 depicts some aspects of a system 100. In some embodiments, a system 100 may include: circuitry for associating at least one anatomic location with predicted activity of the at least one first CYP450-family enzyme; circuitry for associating the at least one anatomic location with one or more of the at least one modulator of the at least one first CYP450-family enzyme; and circuitry for communicating one or more treatment to a system user, wherein the treatment includes the at least one modulator of the at least one first CYP450-family enzyme associated with the at least one anatomic location 1600. An anatomic location, as used herein, may include a body part, tissue, or portions thereof (e.g. "the liver" or "the aorta" or "the vasculature"). In some embodiments, a system 100 includes circuitry for associating at least one anatomic location with predicted activity of the at least one second CYP450-family enzyme; circuitry for associating the at least one anatomic location with one or more of the at least one modulator of the at least one second CYP450-family enzyme; and circuitry for communicating one or more treatment to a system user, wherein the treatment includes the at least one modulator of the at least one second CYP450-family enzyme associated with the at least one anatomic location 1610. In some embodiments, a CYP450-family enzyme may have known or suspected activity in a particular anatomic location, wherein the anatomic location then becomes particularly medically interesting or amenable to treatment options.

FIG. 17 depicts some aspects of a system 1700. In some embodiments, a system may include: circuitry for accepting input that specifies an individual 1710; circuitry for accepting input that identifies a first drug therapy associated with the individual 1720; circuitry for accepting input that identifies a second drug therapy associated with the individual 1730; circuitry for identifying at least one CYP450-family enzyme that influences metabolism of both the first drug therapy and the second drug therapy 1740; circuitry for identifying at least one modulator of one or more of the at least one CYP450-family enzyme 1750; and circuitry for communicating one or more treatment to a system user, wherein the treatment includes one or more of the at least one modulator 1770. A system may communicate with and receive input from a system user 10. A system may include a database 1795. In some embodiments, circuitry for accepting input that specifies an individual 1710 may include circuitry wherein the individual is a representative individual 1780. In some embodiments, circuitry for accepting input that identifies a first drug therapy associated with the individual 1720 includes circuitry wherein the input that identifies a first drug therapy associated with the individual identifies a statin therapy 1785. In some embodiments, circuitry for accepting input that identifies a second drug therapy associated with the individual 1730 includes circuitry wherein the input that identifies a second drug therapy associated with the individual identifies a statin therapy 1790.

FIG. 18 illustrates aspects of a system 1700. In some embodiments, circuitry for accepting input that identifies a first drug therapy associated with the individual 1720 may include circuitry wherein the input that identifies a first drug therapy associated with the individual identifies a cancer chemotherapy 1800. In some embodiments, circuitry for accepting input that identifies a first drug therapy associated with the individual 1720 may include circuitry wherein the input that identifies a first drug therapy associated with the individual identifies a hormone-related therapy 1810. In some embodiments, circuitry for accepting input that identifies a second drug therapy associated with the individual 1730 includes circuitry wherein the input that identifies a second drug therapy associated with the individual identifies a cancer chemotherapy 1820. In some embodiments, circuitry for accepting input that identifies a second drug therapy associated with the individual 1730 includes circuitry wherein the input that identifies a second drug therapy associated with the individual identifies a hormone-related therapy 1830.

FIG. 19 shows aspects of a system 1700. In some embodiments, circuitry for accepting input that identifies a first drug therapy associated with the individual 1720 may include circuitry wherein the input that identifies a first drug therapy associated with the individual identifies an acetaminophen therapy 1900. In some embodiments, circuitry wherein the input that identifies a first drug therapy associated with the individual identifies an acetaminophen therapy 1900 may include circuitry wherein the identifying at least one CYP450-family enzyme that influences metabolism of both the first drug therapy and the second drug therapy includes identifying a CYP2E enzyme 1910. In some embodiments, circuitry for accepting input that identifies a second drug therapy associated with the individual 1730 may include circuitry wherein the input that identifies a second drug therapy associated with the individual identifies an acetaminophen therapy 1920. In some embodiments, circuitry wherein the input that identifies a second drug therapy associated with the individual identifies an acetaminophen therapy 1920 may include circuitry wherein the identifying at least one CYP450-family enzyme that influences metabolism of both the first drug therapy and the second drug therapy includes identifying a CYP2E enzyme 1930.

FIG. 20 depicts aspects of a system 1700. In some embodiments, circuitry for identifying at least one CYP450-family enzyme that influences metabolism of both the first drug therapy and the second drug therapy 1740 includes circuitry wherein the at least one CYP450-family enzyme that influences metabolism of both the first drug therapy and the second drug therapy directly influences metabolism 2000. In some embodiments, circuitry for identifying at least one modulator of one or more of the at least one CYP450-family enzyme 1750 includes circuitry wherein the at least one modulator of one or more of the at least one CYP450-family enzyme is an endogenous modulator 2010. In some embodiments, circuitry for identifying at least one modulator of one or more of the at least one CYP450-family enzyme 1750 includes circuitry wherein the at least one modulator of one or more of the at least one CYP450-family enzyme is an exogenous modulator 2020. In some embodiments, circuitry for identifying at least one modulator of one or more of the at least one CYP450-family enzyme 1750 includes circuitry wherein the at least one modulator of one or more of the at least one CYP450-family enzyme is a synthetic modulator 2030.

FIG. 21 shows aspects of a system 1700. In some embodiments, a system 1700 may include: circuitry for accepting input specifying one or more variant of at least one CYP450-family enzyme associated with the individual; circuitry for identifying at least one modulator of the one or more variant; and circuitry for communicating one or more treatment to a system user, wherein the one or more treatment includes one or more of the identified at least one modulator of the one or more variant 2100. In some embodiments, circuitry 2100 may include circuitry wherein the one or more variant of at least one CYP450-family enzyme is directly associated with the individual 2110. In some embodiments, a system may include circuitry wherein the one or more variant of at least one CYP450-family enzyme is indirectly associated with the individual. In some embodiments, a system may include circuitry wherein the one or more variant of at least one CYP450-family enzyme is associated with a population or group, which may include the individual.

FIG. 22 depicts aspects of a system 1700. In some embodiments, a system 1700 may include: circuitry for accepting input specifying one or more variant of at least one CYP450-family gene associated with the individual; circuitry for identifying at least one modulator of the one or more variant of at least one CYP450-family gene; and circuitry for communicating one or more treatment to a system user, wherein the one or more treatment includes one or more of the identified at least one modulator of the one or more variant of the at least one CYP450-family gene 2200. In some embodiments, circuitry 2200 may include circuitry wherein the one or more variant of at least one CYP450-family gene is directly associated with the individual 2210. In some embodiments, a system may include circuitry wherein the one or more variant of at least one CYP450-family gene is indirectly associated with the individual. In some embodiments, a system may include circuitry wherein the one or more variant of at least one CYP450-family gene is associated with a population or group, which may include the individual.

FIG. 23 illustrates aspects of a system 1700. Some embodiments include: circuitry for accepting input specifying one or more variant of the at least one first CYP450-family enzyme associated with the individual; circuitry for accepting input specifying one or more variant of the at least one second CYP450-family enzyme associated with the individual; circuitry for identifying at least one modulator of the one or more variant of the at least one first CYP450-family enzyme; circuitry for identifying at least one modulator of the one or more variant of the at least one second CYP450-family enzyme; and circuitry for communicating one or more treatment to a system user, wherein the treatment includes the identified at least one modulator of the one or more variant of the at least one first CYP450-family enzyme and the identified at least one modulator of the one or more variant of the at least one second CYP450-family enzyme 2300.

FIG. 24 shows aspects of a system 1700. In some embodiments, a system 1700 may include circuitry for communicating at least one modulator of one or more of the at least one first CYP450-family enzyme to a system user 2400. Some embodiments of a system 1700 may include circuitry for communicating at least one modulator of one or more of the at least one second CYP450-family enzyme to a system user 2410. Some embodiments of a system 1700 may include circuitry for identifying one or more treatments including at least one identified at least one modulator of one or more of the at least one first CYP450-family enzyme and at least one identified at least one modulator of one or more of the at least one second CYP450-family enzyme 2420.

FIG. 25 depicts aspects of a system 1700. In some embodiments, a system 1700 may include: circuitry for suggesting one or more dosages of the one or more treatment to a system user; circuitry for identifying at least one environmental factor associated with an alteration in activity of at least one of the one or more treatment; and circuitry for communicating one or more alternate dosages of the one or more treatment, wherein the one or more alternate dosages are calculated to compensate for the alteration in activity of at least one of the one or more treatment 2500. In some embodiments, a system 1700 may include: circuitry for identifying at least one environmental factor associated with activity of the at least one CYP450-family enzyme; and circuitry for communicating at least one environmental mitigation strategy to a system user 2510. In some embodiments, circuitry 2510 may include circuitry wherein the at least one environmental factor is associated with the individual 2520. Some embodiments may include where the at least one environmental factor is not directly associated with the individual. Some embodiments may include wherein the at least one environmental factor is associated with a population or group.

FIG. 26 illustrates aspects of a system 1700. In some embodiments, a system 1700 includes: circuitry for identifying at least one dietary factor associated with an alteration in activity of at least one of the one or more treatment; and circuitry for communicating one or more alternate dosages of the one or more treatment, wherein the one or more alternate dosages are calculated to compensate for the alteration in activity of at least one of the one or more treatment 2600. In some embodiments, a system 1700 may include: circuitry for identifying at least one dietary factor associated with activity of the at least one CYP450-family enzyme; and circuitry for communicating at least one dietary mitigation strategy to a system user 2610. Some embodiments of circuitry 2610 may include circuitry wherein the at least one dietary factor is associated with the individual 2620. Some embodiments may include where the at least one dietary factor is not directly associated with the individual. Some embodiments may include wherein the at least one dietary factor is associated with a population or group.

Figure 27:
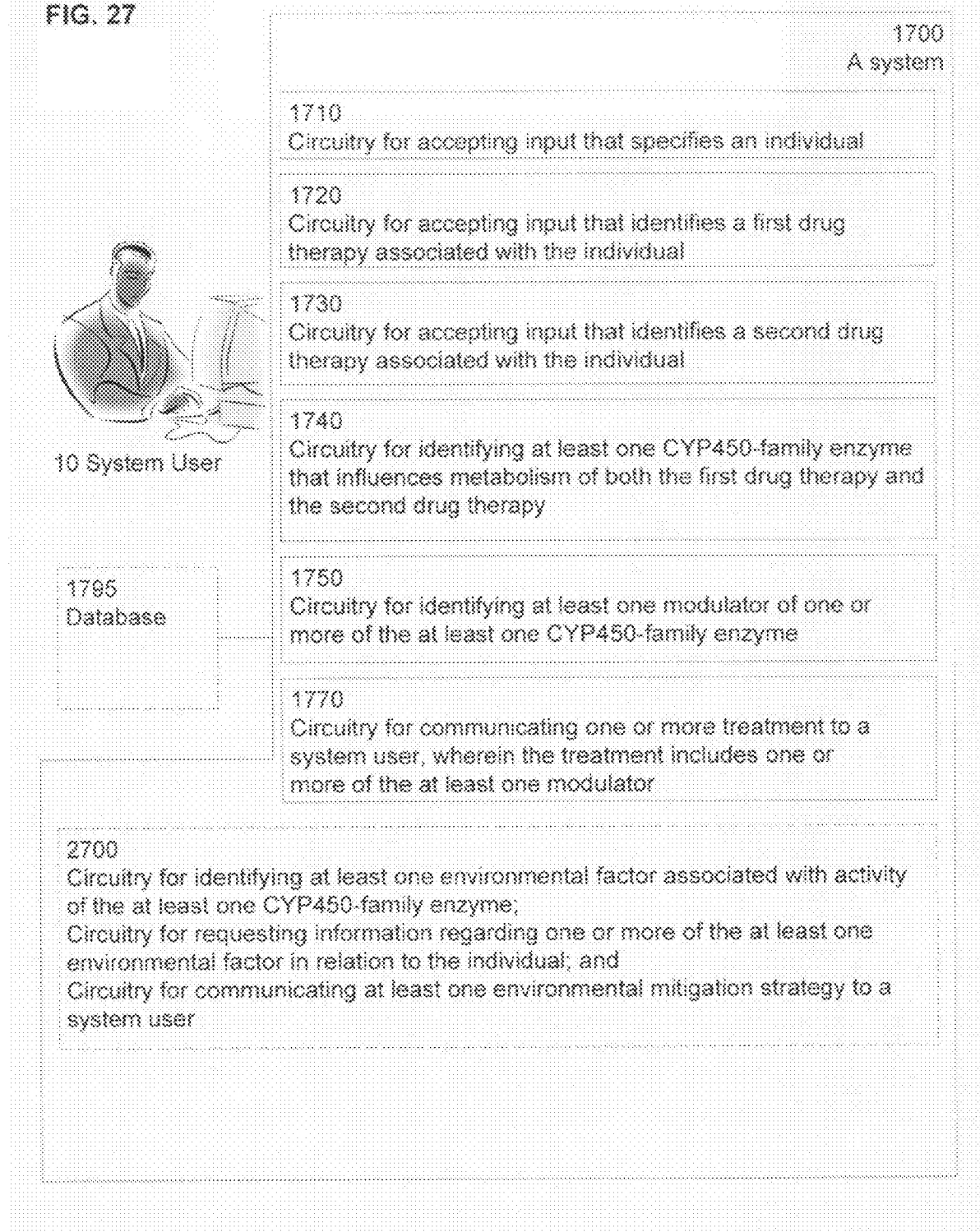
FIG. 27 is a diagram illustrating some aspects of a system such as the one depicted in FIG. 17.

FIG. 27 shows aspects of a system 1700. In some embodiments, a system 1700 includes: circuitry for identifying at least one environmental factor associated with activity of the at least one CYP450-family enzyme; circuitry for requesting information regarding one or more of the at least one environmental factor in relation to the individual; and circuitry for communicating at least one environmental mitigation strategy to a system user 2700.

Figure 28:
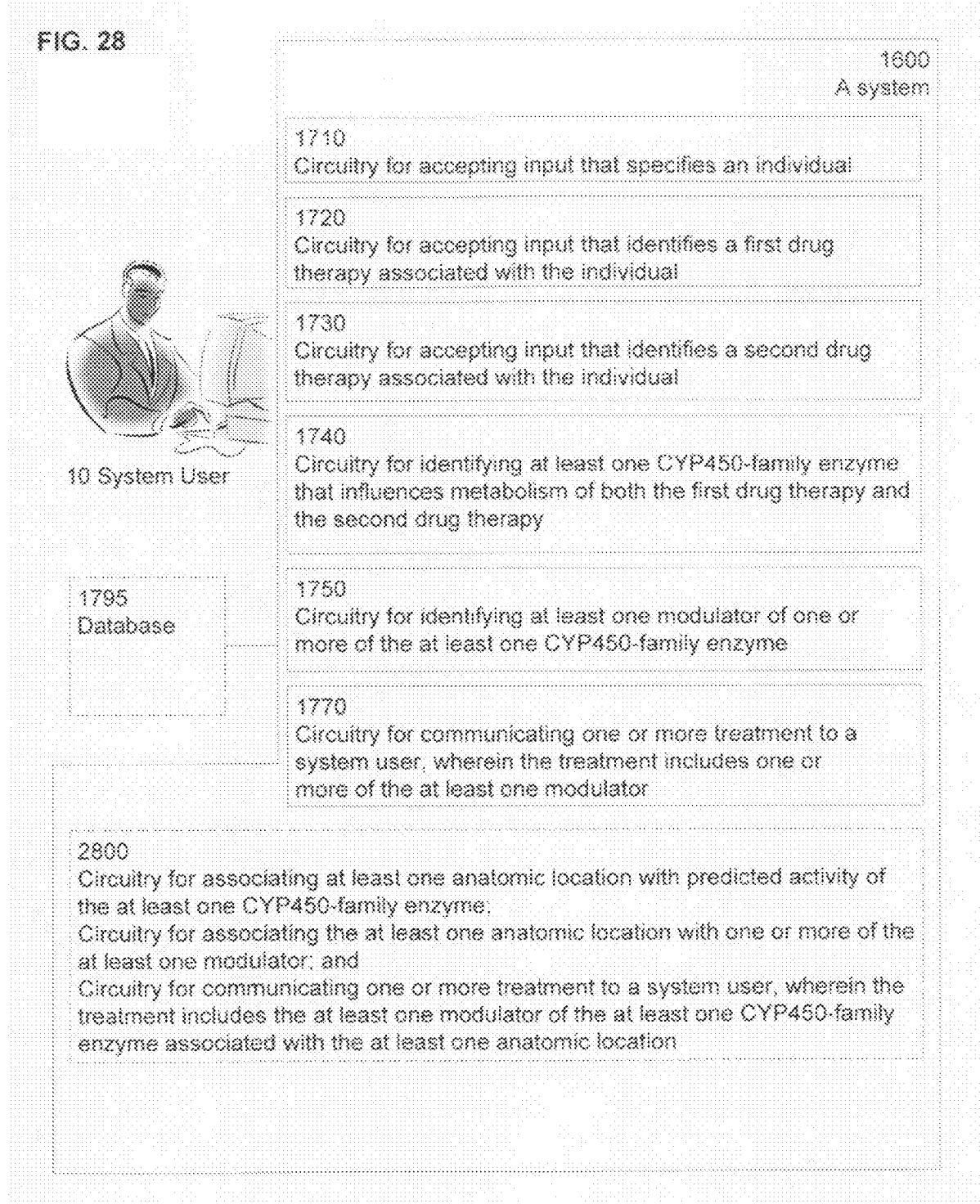
FIG. 28 is a diagram illustrating some aspects of a system such as the one depicted in FIG. 17.

FIG. 28 depicts aspects of a system 1700. In some embodiments, a system 1700 includes: circuitry for associating at least one anatomic location with predicted activity of the at least one CYP450-family enzyme; circuitry for associating the at least one anatomic location with one or more of the at least one modulator; and circuitry for communicating one or more treatment to a system user, wherein the treatment includes the at least one modulator of the at least one CYP450-family enzyme associated with the at least one anatomic location 2800.

Figure 29:
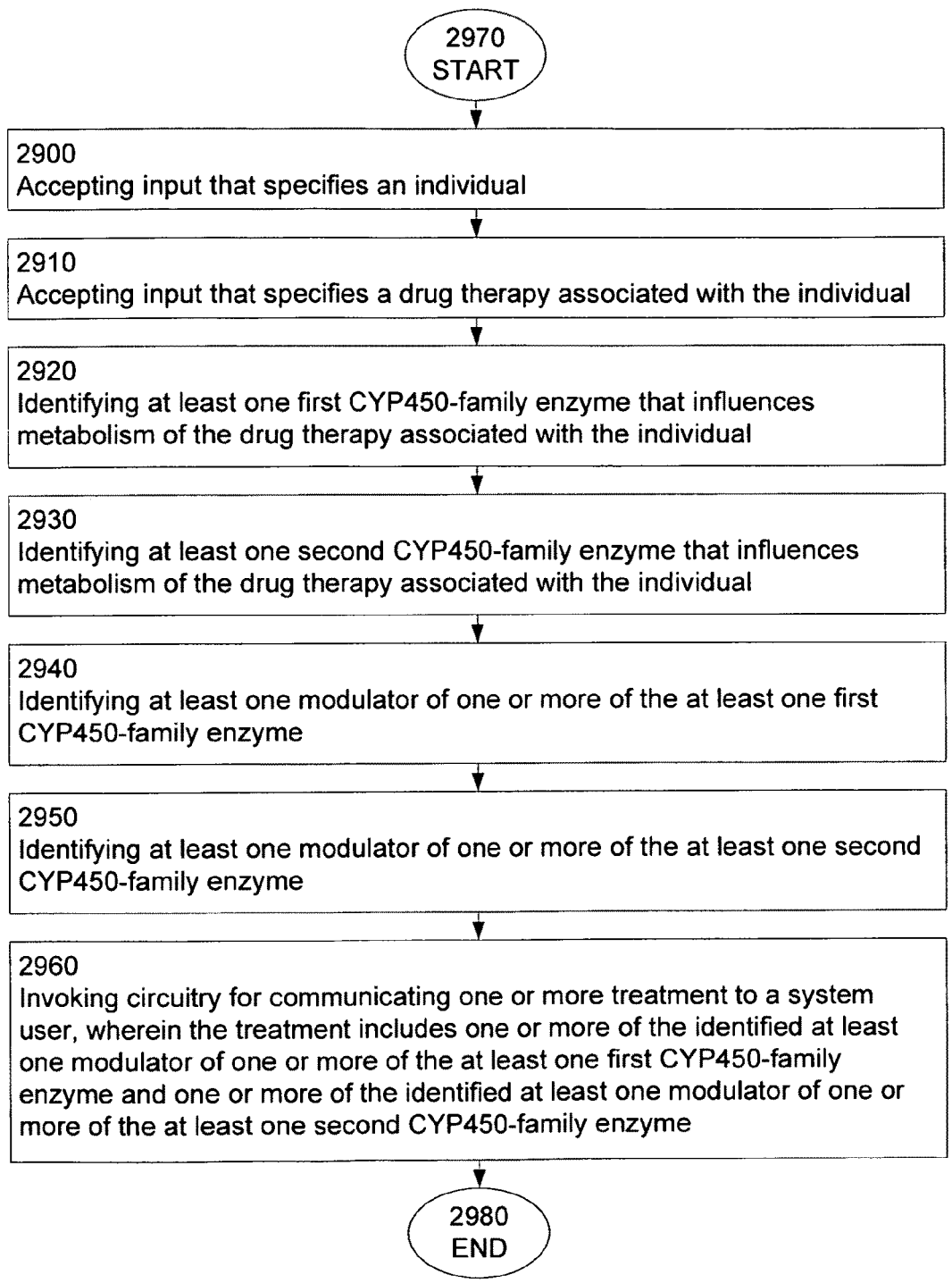
FIG. 29 is a flowchart depicting aspects of a method.

FIG. 29 illustrates aspects of a method. The method begins at the start, depicted as block 2970. It should be noted that any method blocks depicted herein as "start" or "stop" or "end" are for illustrative purposes and do not necessarily mean that the described method must "start" or "end" at a specified method block, or that there are no other method steps contemplated either prior to "start" or after "end" or "stop." The described method could be incorporated into or within another method, for example. Method block 2900 depicts accepting input that specifies an individual. Method block 2910 illustrates accepting input that specifies a drug therapy associated with the individual. Method block 2920 shows identifying at least one first CYP450-family enzyme that influences metabolism of the drug therapy associated with the individual. Method block 2930 shows identifying at least one second CYP450-family enzyme that influences metabolism of the drug therapy associated with the individual. Method block 2940 depicts identifying at least one modulator of one or more of the at least one first CYP450-family enzyme. Method block 2950 illustrates identifying at least one modulator of one or more of the at least one second CYP450-family enzyme. Method block 2960 shows invoking circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme. In some embodiments, one or more steps of a method may be implemented by circuitry, or a computing device. In some embodiments, one or more steps of a method may be performed by or on a computing device or performed by or on circuitry. In some embodiments, one or more steps of a method may invoke circuitry. Method block 2980 depicts the end of the method.

Figure 30:
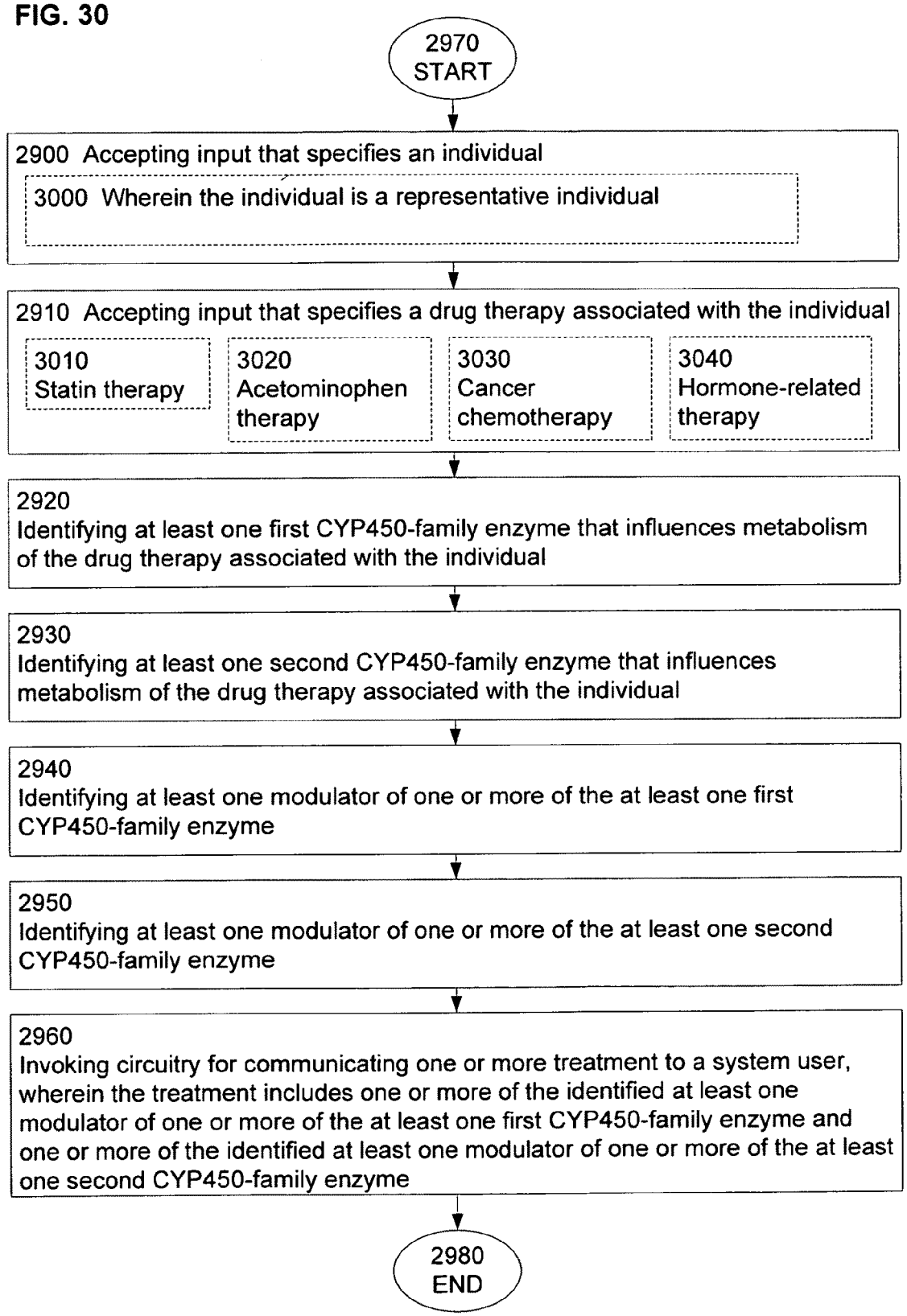
FIG. 30 is a flowchart depicting aspects of a method such as the one shown in FIG. 29.

FIG. 30 shows aspects of a method as depicted in FIG. 29. In some aspects, method block 2900, depicting accepting input that specifies an individual, may include method block 3000, wherein the individual is a representative individual. Method block 2910, illustrating accepting input that specifies a drug therapy associated with the individual, may include one or more of method blocks 3010, 3020, 3030 and 3040. Method block 3010 depicts wherein the drug therapy is a statin therapy. Method block 3020 illustrates wherein the drug therapy is an acetominophen therapy. Method block 3030 shows wherein the drug therapy is a cancer chemotherapy. Method block 3040 depicts wherein the drug therapy is a hormone-related therapy.

Figure 31:
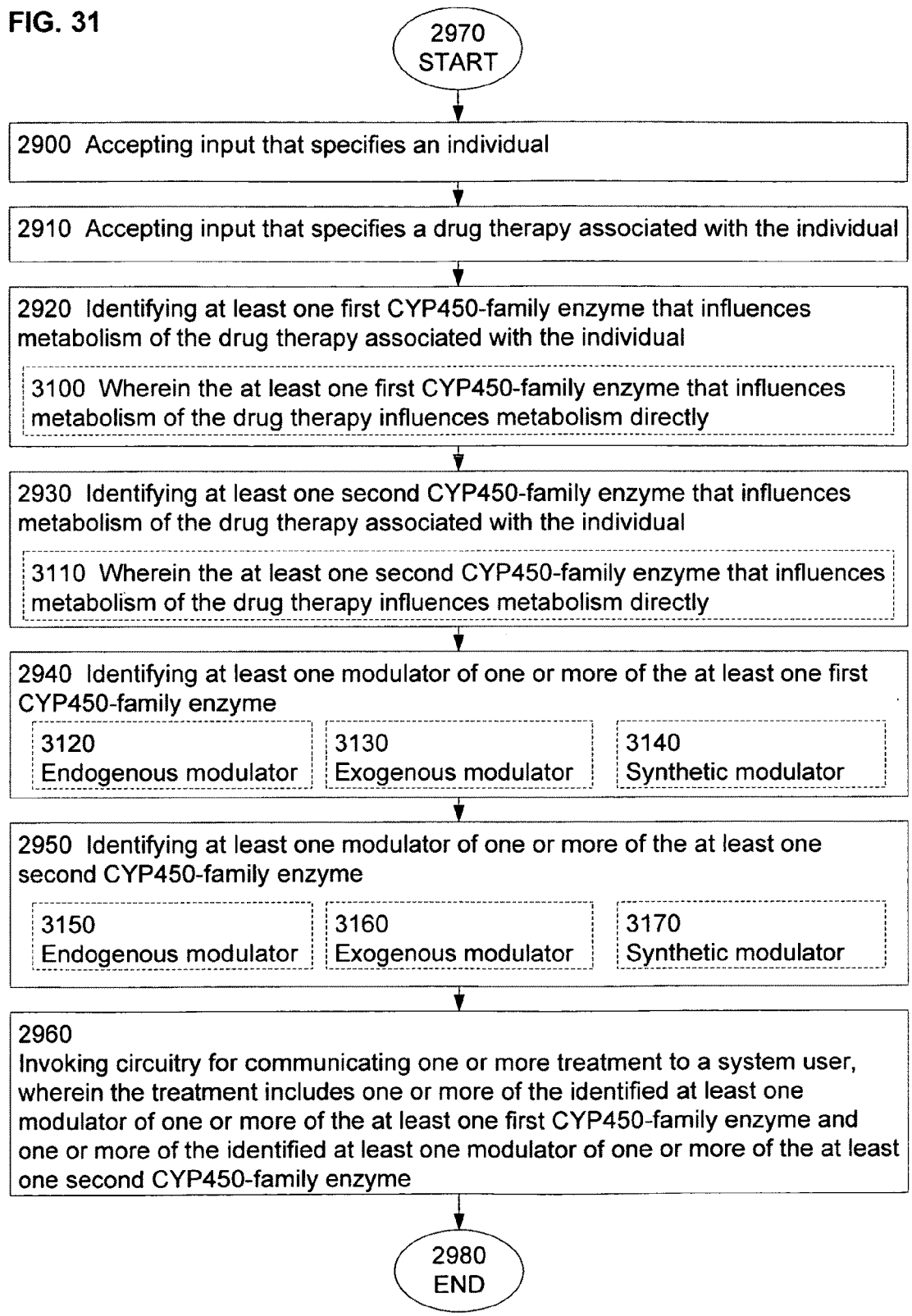
FIG. 31 is a flowchart illustrating aspects of a method such as the one depicted in FIG. 29.

FIG. 31 depicts aspects of a method as shown in FIG. 29. Method block 2920, showing identifying at least one first CYP450-family enzyme that influences metabolism of the drug therapy associated with the individual, may include method block 3100 depicting wherein the at least one first CYP450-family enzyme that influences metabolism of the drug therapy influences metabolism directly. A method may also include wherein the at least one first CYP450-family enzyme that influences metabolism of the drug therapy influences metabolism indirectly. Method block 2930, showing identifying at least one second CYP450-family enzyme that influences metabolism of the drug therapy associated with the individual, may include method block 3110 depicting wherein the at least one second CYP450-family enzyme that influences metabolism of the drug therapy influences metabolism directly. A method may also include wherein the at least one second CYP450-family enzyme that influences metabolism of the drug therapy influences metabolism indirectly. Method block 2940, showing identifying at least one modulator of one or more of the at least one first CYP450-family enzyme, may include one or more of method blocks 3120, 3130, and 3140. Method block 3120 depicts wherein the at least one modulator of one or more of the at least one first CYP450-family enzyme is an endogenous modulator. Method block 3130 illustrates wherein the at least one modulator of one or more of the at least one first CYP450-family enzyme is an exogenous modulator. Method block 3140 depicts wherein the at least one modulator of one or more of the at least one first CYP450-family enzyme is a synthetic modulator. Method block 2950, showing identifying at least one modulator of one or more of the at least one second CYP450-family enzyme, may include one or more of method blocks 3150, 3160, and 3170. Method block 3150 shows wherein the at least one modulator of one or more of the at least one second CYP450-family enzyme is an endogenous modulator. Method block 3160 illustrates wherein the at least one modulator of one or more of the at least one second CYP450-family enzyme is an exogenous modulator. Method block 3170 shows wherein the at least one modulator of one or more of the at least one second CYP450-family enzyme is a synthetic modulator.

Figure 32:
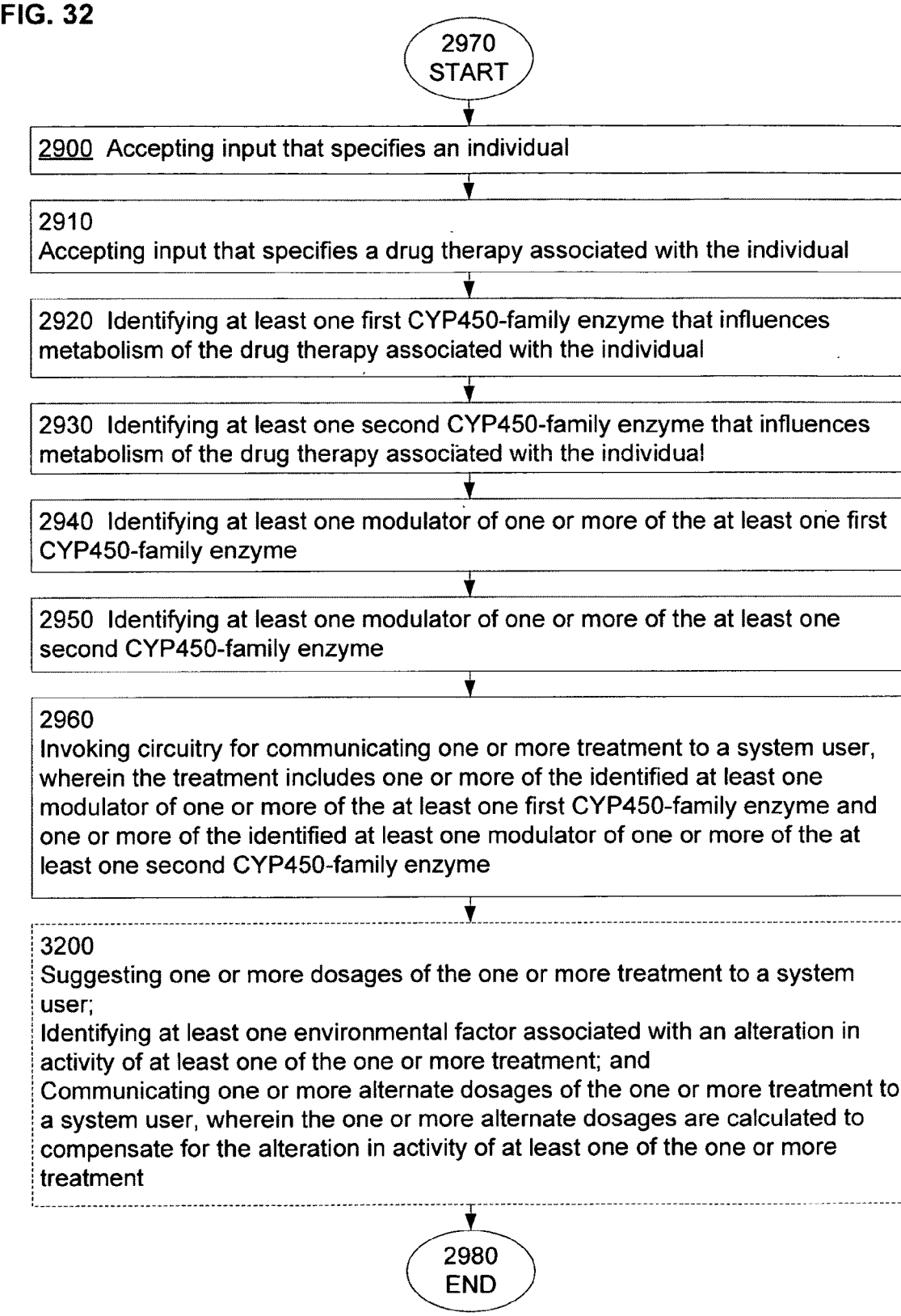
FIG. 32 is a flowchart depicting aspects of a method such as the one shown in FIG. 29.

FIG. 32 illustrates aspects of a method as shown in FIG. 29. A method diagram may include block 3200, illustrating: suggesting one or more dosages of the one or more treatment to a system user; identifying at least one environmental factor associated with an alteration in activity of at least one of the one or more treatment; and communicating one or more alternate dosages of the one or more treatment to a system user, wherein the one or more alternate dosages are calculated to compensate for the alteration in activity of at least one of the one or more treatment.

Figure 33:
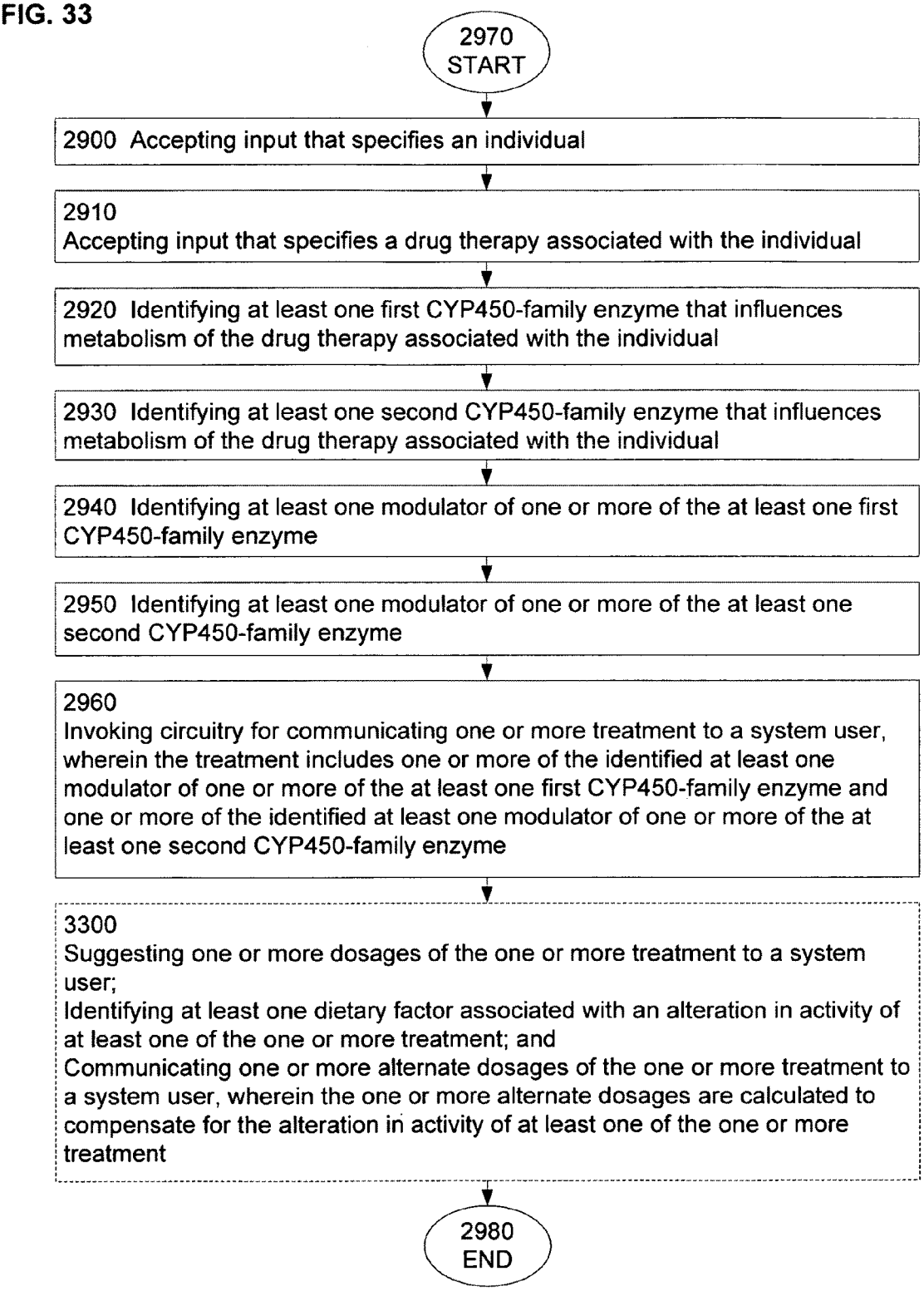
FIG. 33 is a flowchart illustrating aspects of a method such as the one depicted in FIG. 29.

FIG. 33 shows aspects of a method as illustrated in FIG. 29. A method diagram may include block 3300, illustrating: suggesting one or more dosages of the one or more treatment to a system user; identifying at least one dietary factor associated with an alteration in activity of at least one of the one or more treatment; and communicating one or more alternate dosages of the one or more treatment to a system user, wherein the one or more alternate dosages are calculated to compensate for the alteration in activity of at least one of the one or more treatment.

Figure 34:
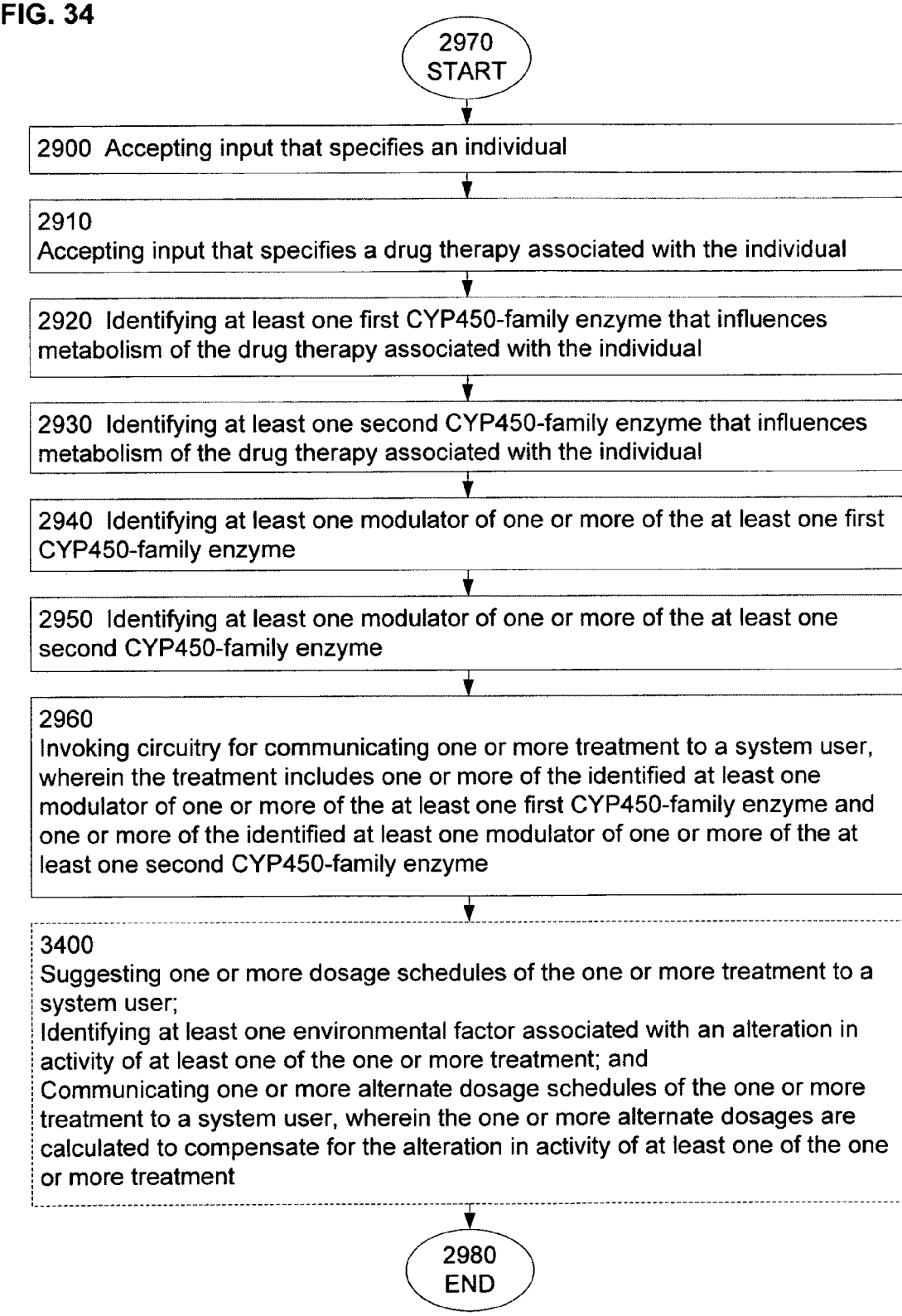
FIG. 34 is a flowchart depicting aspects of a method such as the one shown in FIG. 29.

FIG. 34 depicts aspects of a method as illustrated in FIG. 29. A method diagram may include block 3400, illustrating: suggesting one or more dosage schedules of the one or more treatment to a system user; identifying at least one environmental factor associated with an alteration in activity of at least one of the one or more treatment; and communicating one or more alternate dosage schedules of the one or more treatment to a system user, wherein the one or more alternate dosages are calculated to compensate for the alteration in activity of at least one of the one or more treatment.

Figure 35:
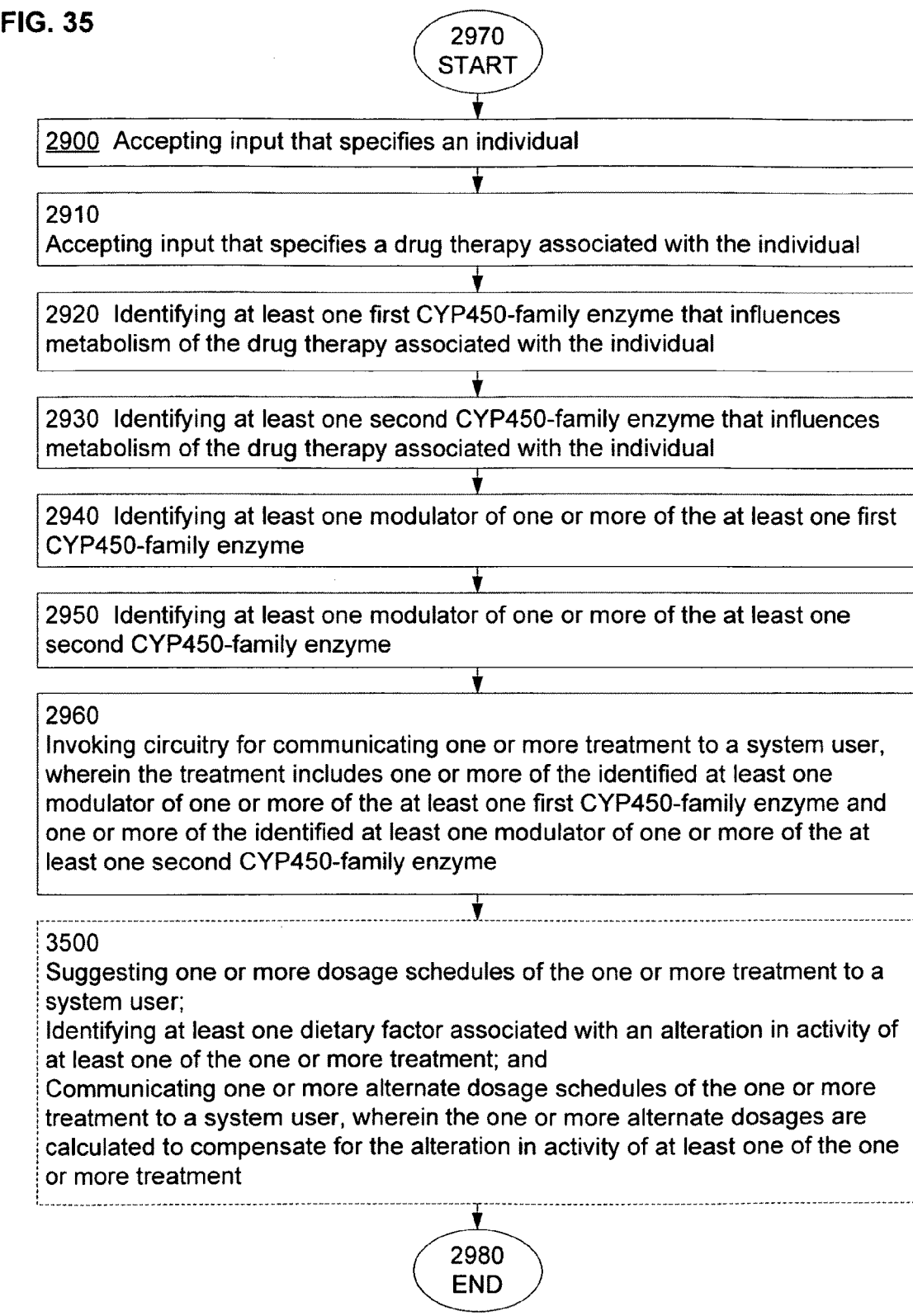
FIG. 35 is a flowchart illustrating aspects of a method such as the one depicted in FIG. 29.

FIG. 35 illustrates aspects of a method as shown in FIG. 29. A method diagram may include block 3500, depicting: suggesting one or more dosage schedules of the one or more treatment to a system user; identifying at least one dietary factor associated with an alteration in activity of at least one of the one or more treatment; and communicating one or more alternate dosage schedules of the one or more treatment to a system user, wherein the one or more alternate dosages are calculated to compensate for the alteration in activity of at least one of the one or more treatment.

Figure 36:
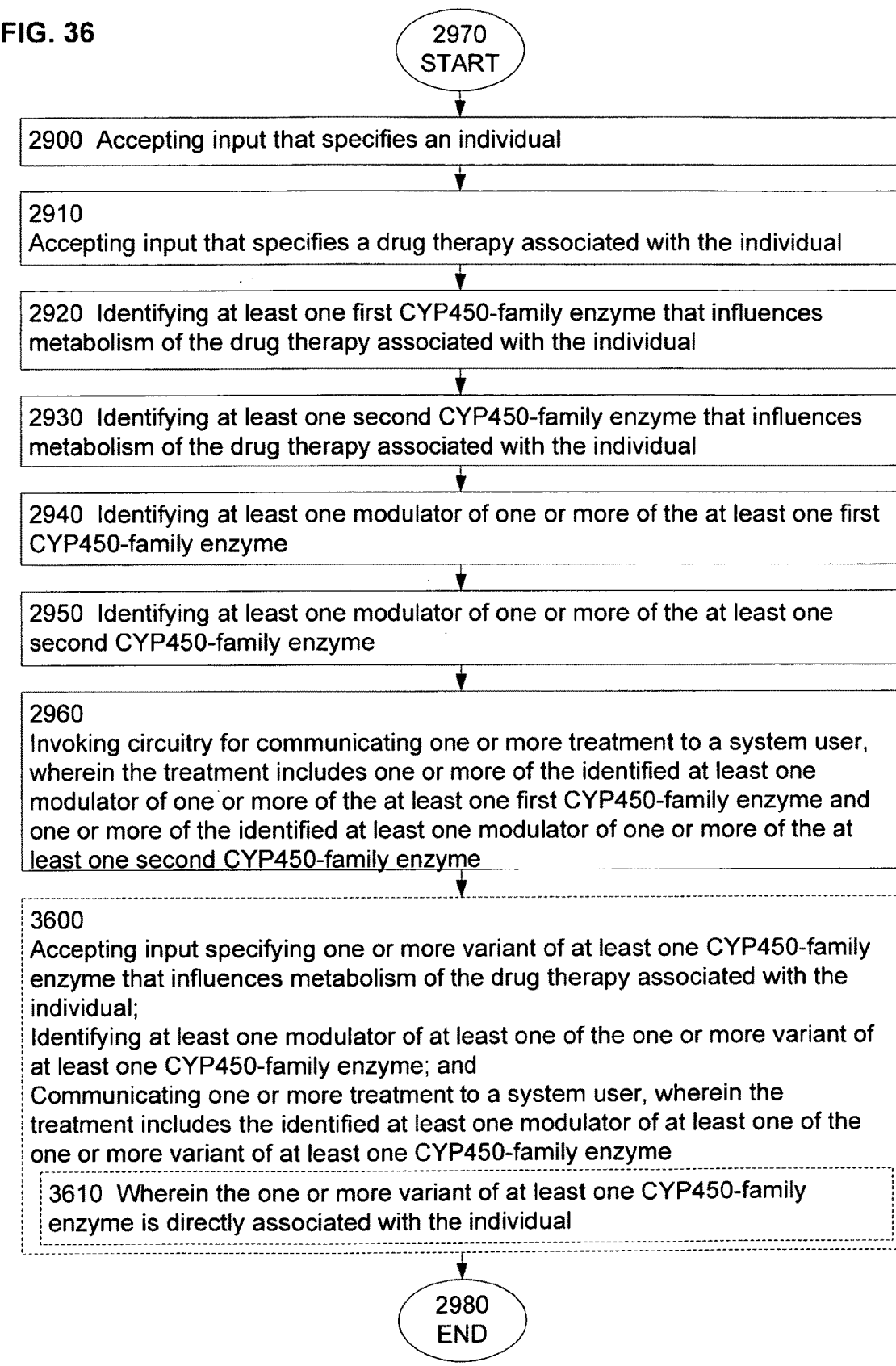
FIG. 36 is a flowchart depicting aspects of a method such as the one shown in FIG. 29.

FIG. 36 shows aspects of a method as depicted in FIG. 29. A method diagram may include block 3600, illustrating: accepting input specifying one or more variant of at least one CYP450-family enzyme that influences metabolism of the drug therapy associated with the individual; identifying at least one modulator of at least one of the one or more variant of at least one CYP450-family enzyme; and communicating one or more treatment to a system user, wherein the treatment includes the identified at least one modulator of at least one of the one or more variant of at least one CYP450-family enzyme. Block 3600 may also include block 3610, showing wherein the one or more variant of at least one CYP450-family enzyme is directly associated with the individual. A method may also include wherein the one or more variant of at least one CYP450-family enzyme is indirectly associated with the individual, for example via indirect biochemical or metabolic testing. A method may also include wherein the one or more variant of at least one CYP450-family enzyme is directly associated with a group or population that includes the individual, for example an ethnic group or patient population.

Figure 37:
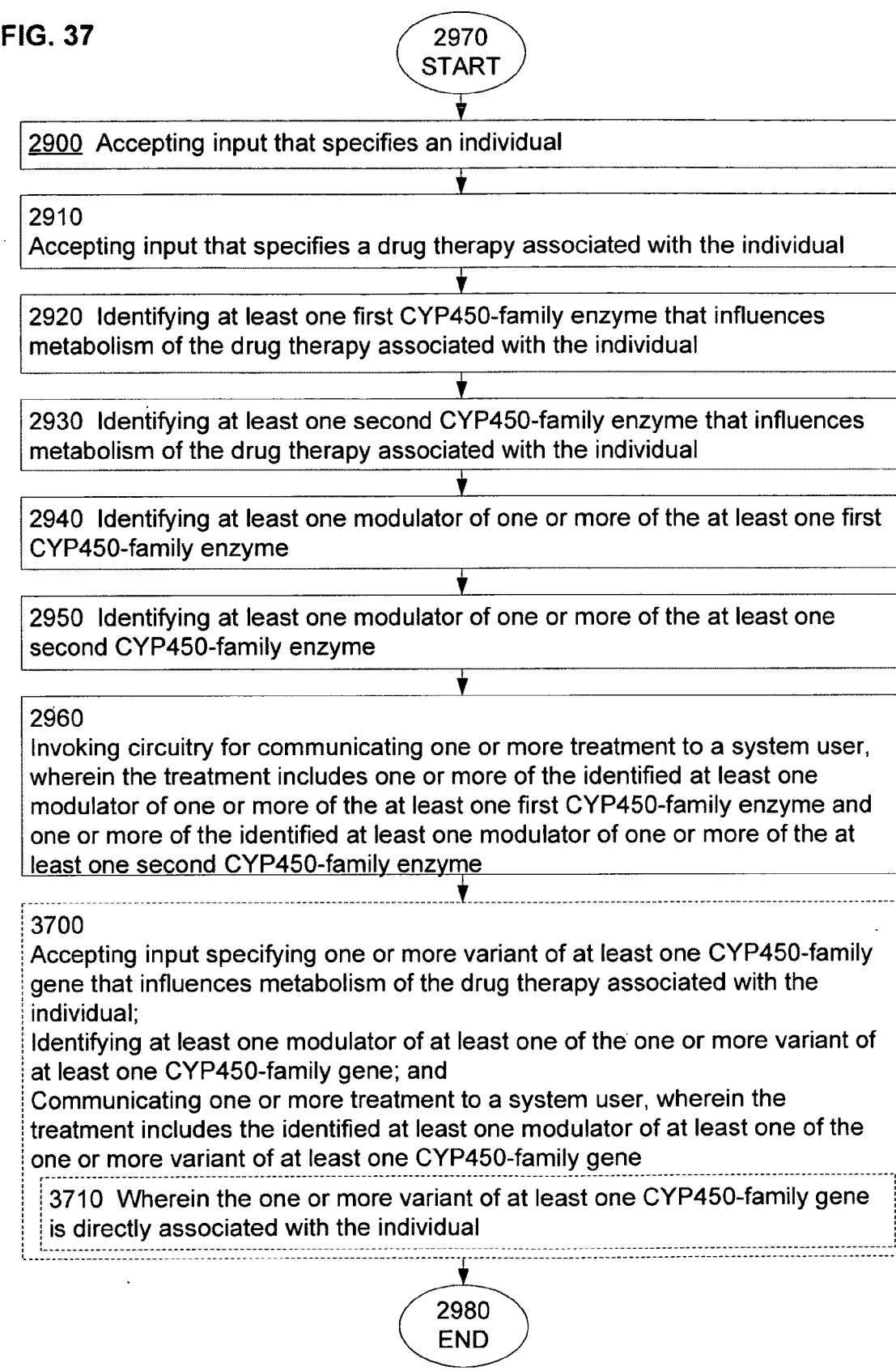
FIG. 37 is a flowchart illustrating aspects of a method such as the one depicted in FIG. 29.

FIG. 37 illustrates aspects of a method as depicted in FIG. 29. A method diagram may include block 3700, showing: accepting input specifying one or more variant of at least one CYP450-family gene that influences metabolism of the drug therapy associated with the individual; identifying at least one modulator of at least one of the one or more variant of at least one CYP450-family gene; and communicating one or more treatment to a system user, wherein the treatment includes the identified at least one modulator of at least one of the one or more variant of at least one CYP450-family gene. Block 3700 may also include block 3710, showing wherein the one or more variant of at least one CYP450-family gene is directly associated with the individual. A method may also include wherein the one or more variant of at least one CYP450-family gene is indirectly associated with the individual, such as, for example, through a family relationship. A method may also include wherein the one or more variant of at least one CYP450-family gene is directly associated with a group or population that includes the individual, such as, for example, an ethnic group or patient population.

Figure 38:
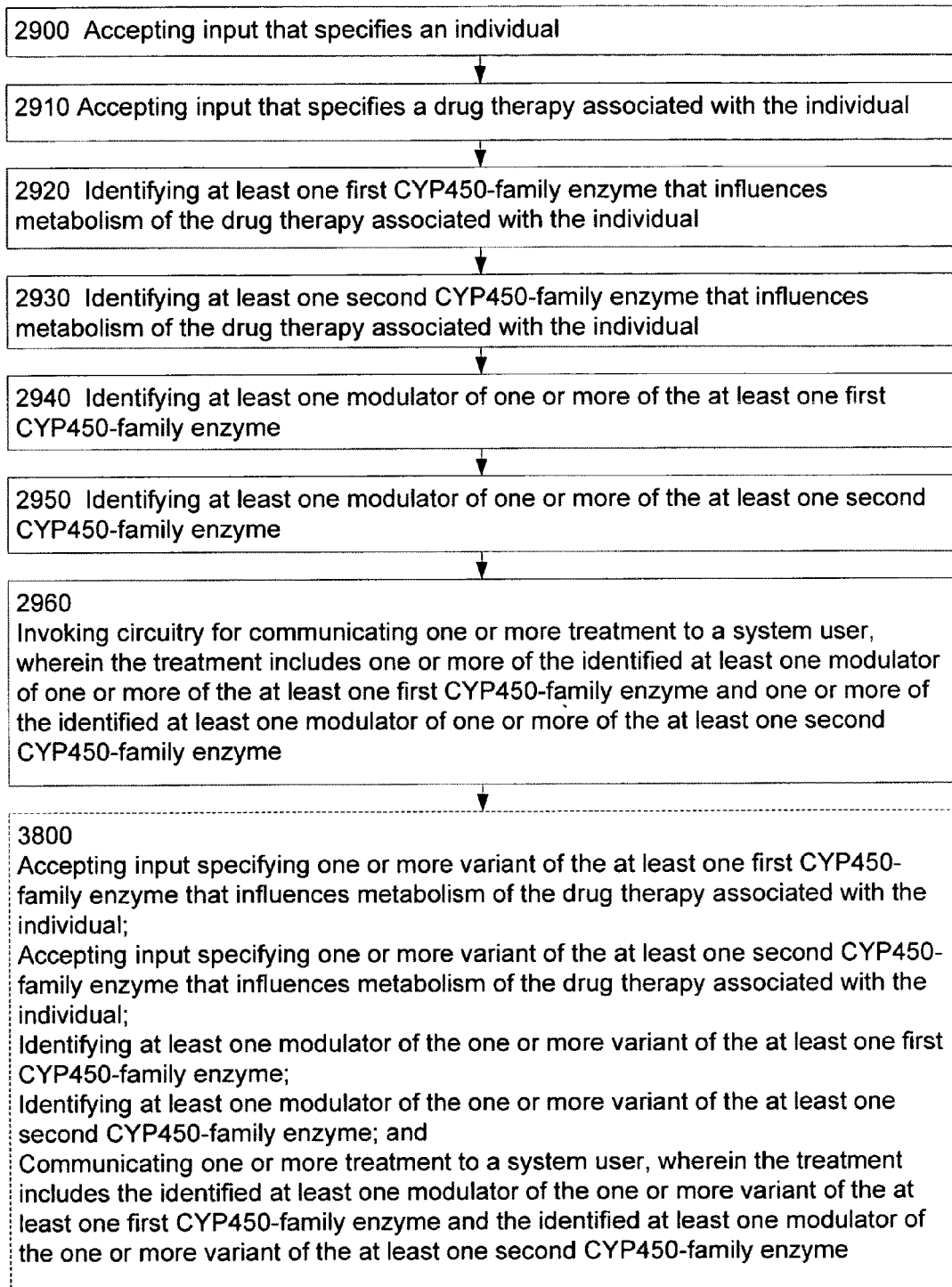
FIG. 38 is a flowchart depicting aspects of a method such as the one shown in FIG. 29.

FIG. 38 shows aspects of a method as depicted in FIG. 29. A method diagram may include block 3800, illustrating: accepting input specifying one or more variant of the at least one first CYP450-family enzyme that influences metabolism of the drug therapy associated with the individual; accepting input specifying one or more variant of the at least one second CYP450-family enzyme that influences metabolism of the drug therapy associated with the individual; identifying at least one modulator of the one or more variant of the at least one first CYP450-family enzyme; identifying at least one modulator of the one or more variant of the at least one second CYP450-family enzyme; and communicating one or more treatment to a system user, wherein the treatment includes the identified at least one modulator of the one or more variant of the at least one first CYP450-family enzyme and the identified at least one modulator of the one or more variant of the at least one second CYP450-family enzyme.

Figure 39:
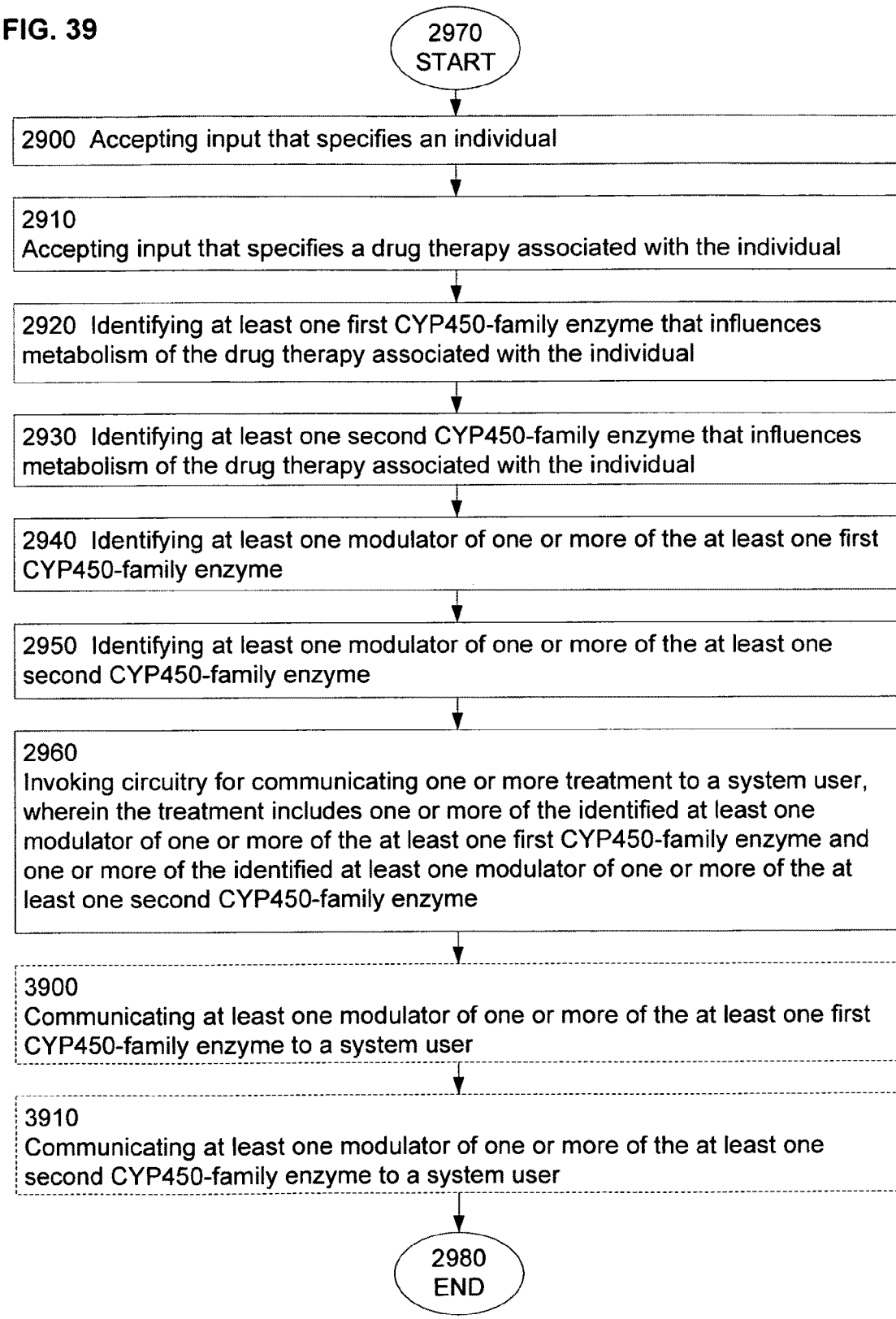
FIG. 39 is a flowchart illustrating aspects of a method such as the one depicted in FIG. 29.

FIG. 39 illustrates aspects of a method as shown in FIG. 29. A method diagram may include block 3900, showing communicating at least one modulator of one or more of the at least one first CYP450-family enzyme to a system user. A method diagram may include block 3910, illustrating communicating at least one modulator of one or more of the at least one second CYP450-family enzyme to a system user.

Figure 40:
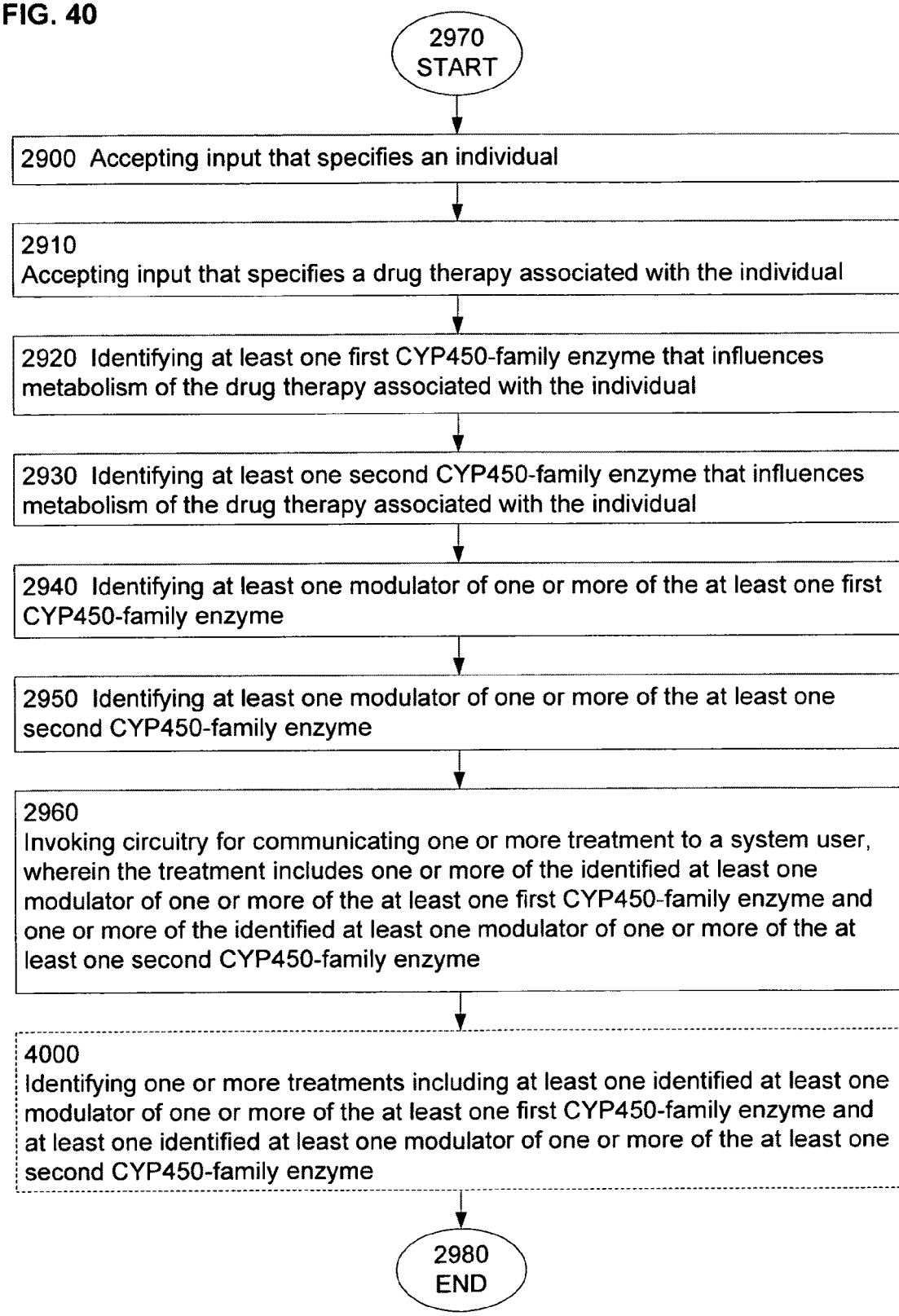
FIG. 40 is a flowchart depicting aspects of a method such as the one shown in FIG. 29.

FIG. 40 depicts aspects of a method as illustrated in FIG. 29. A method diagram may include block 4000, illustrating: identifying one or more treatments including at least one identified at least one modulator of one or more of the at least one first CYP450-family enzyme and at least one identified at least one modulator of one or more of the at least one second CYP450-family enzyme.

Figure 41:
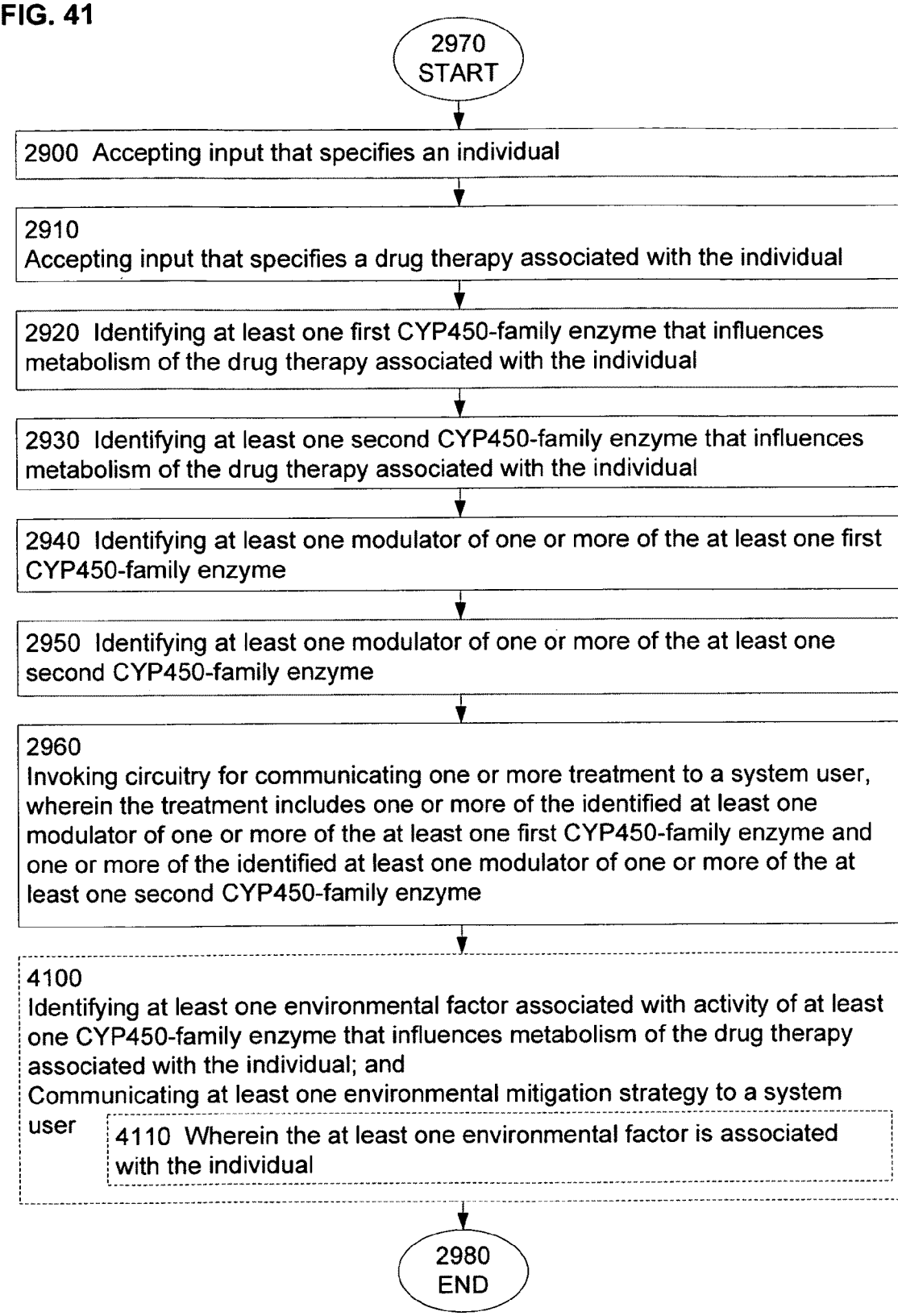
FIG. 41 is a flowchart illustrating aspects of a method such as the one depicted in FIG. 29.

FIG. 41 shows aspects of a method as depicted in FIG. 29. A method diagram may include block 4100, illustrating: identifying at least one environmental factor associated with activity of at least one CYP450-family enzyme that influences metabolism of the drug therapy associated with the individual; and communicating at least one environmental mitigation strategy to a system user. Method block 4100 may include method block 4110, depicting wherein the at least one environmental factor is associated with the individual. In some methods, the at least one environmental factor may not be associated with the individual. In some methods, the at least one environmental factor may be indirectly associated with the individual, such as when the individual is included in a population or group associated with the environmental factor. For example, an individual may be included in the group "employment as a workplace cleaner" and therefore indirectly associated with exposure to carbon tetrachloride.

Figure 42:
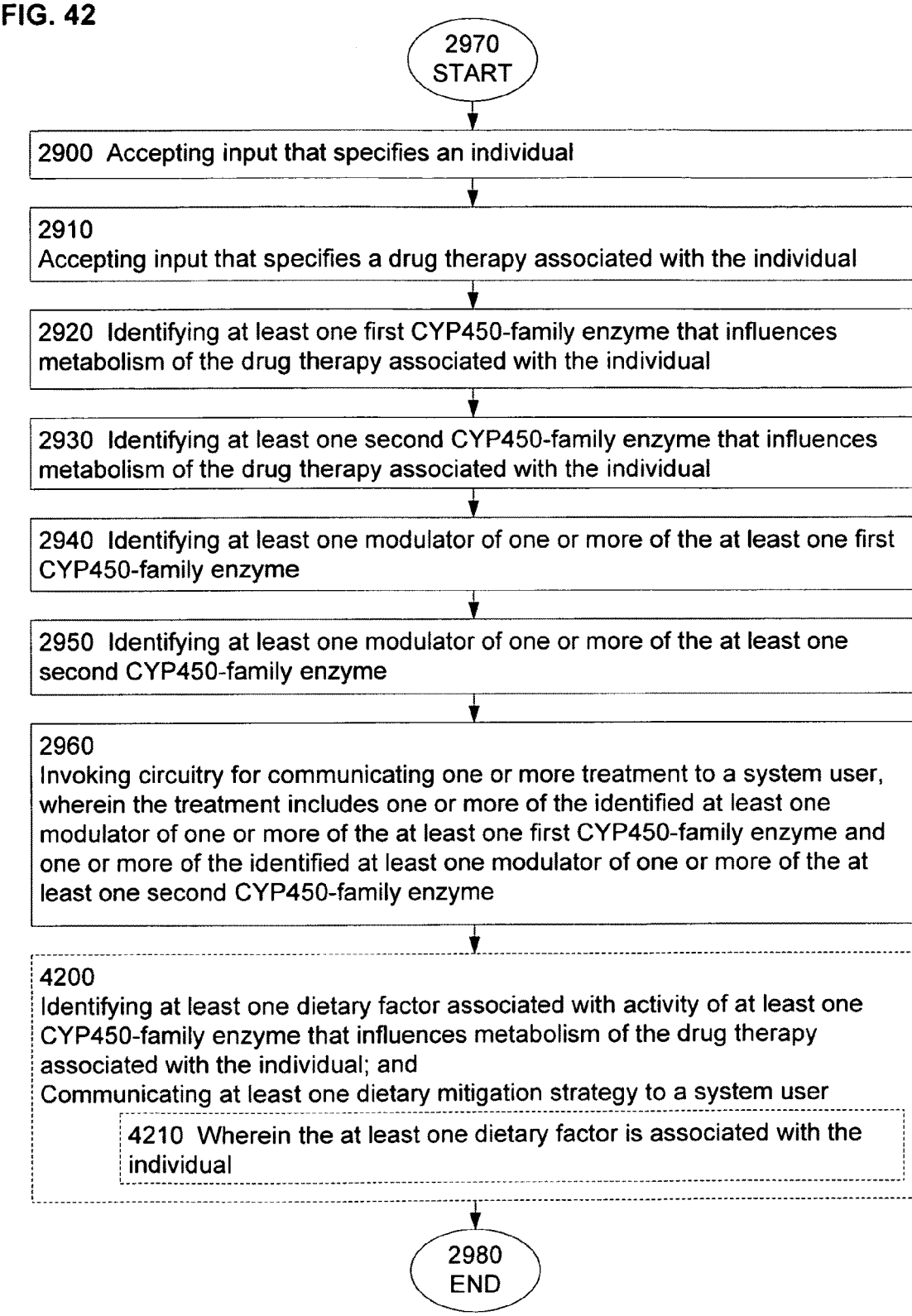
FIG. 42 is a flowchart depicting aspects of a method such as the one shown in FIG. 29.

FIG. 42 depicts aspects of a method as shown in FIG. 29. A method diagram may include block 4200, illustrating: identifying at least one dietary factor associated with activity of at least one CYP450-family enzyme that influences metabolism of the drug therapy associated with the individual; and communicating at least one dietary mitigation strategy to a system user. Method block 4200 may include method block 4210, depicting wherein the at least one dietary factor is associated with the individual. In some methods, at least one dietary factor may not be associated with the individual. In some methods, the at least one dietary factor may be indirectly associated with the individual, such as when the individual is part of a group or population that is associated with at least one dietary factor. For example, an individual may be included in a population of vegetarians and therefore indirectly associated with little or no ingestion of red meat or high ingestion levels of vegetables. For example, an individual may be included in a population of people sensitive to gluten, and therefore indirectly associated with little or no ingestion of baked goods, what-based pasta, or some beverages.

Figure 43:
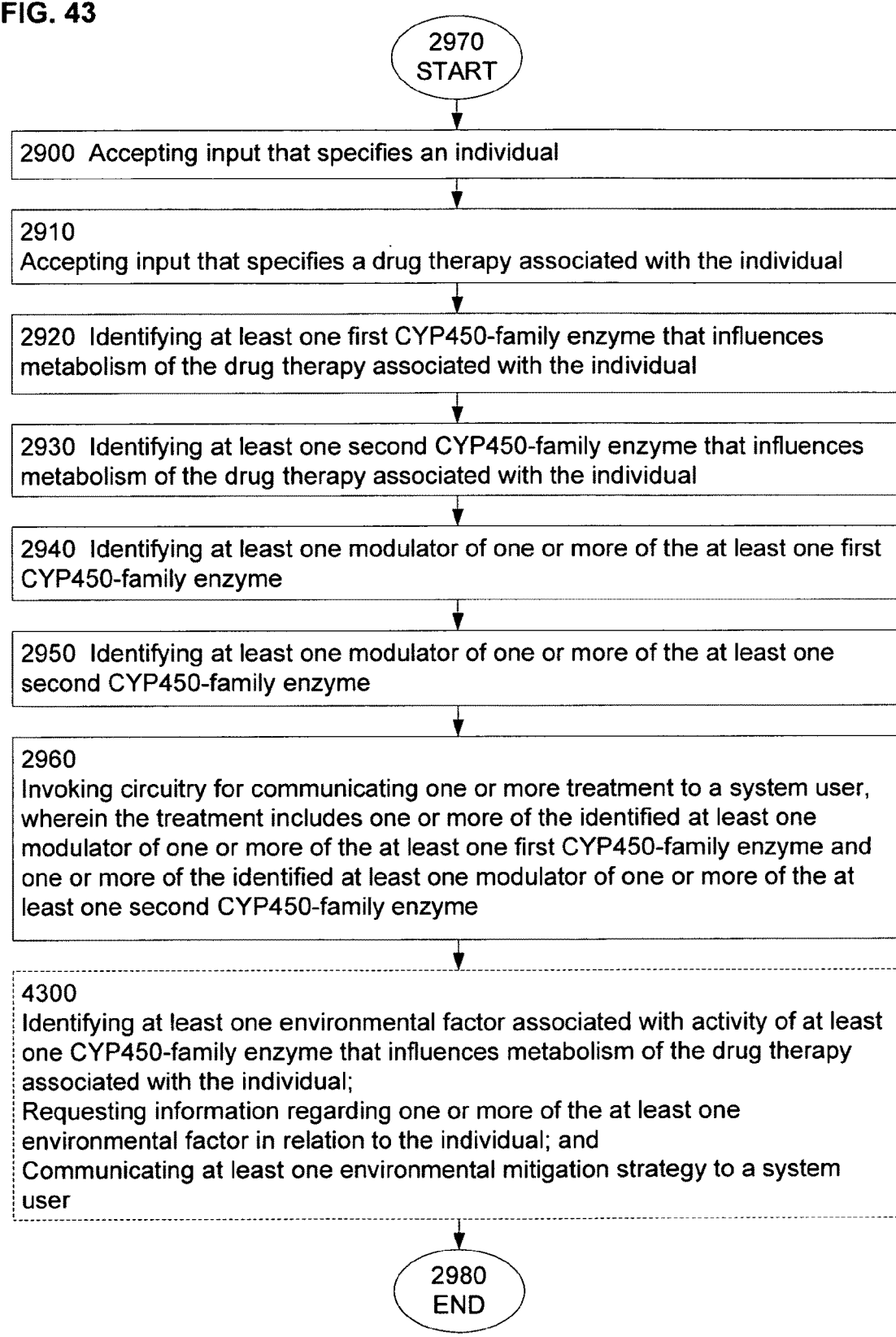
FIG. 43 is a flowchart depicting aspects of a method such as the one shown in FIG. 29.

FIG. 43 shows aspects of a method as illustrated in FIG. 29. A method diagram may include block 4300, showing: identifying at least one environmental factor associated with activity of at least one CYP450-family enzyme that influences metabolism of the drug therapy associated with the individual; requesting information regarding one or more of the at least one environmental factor in relation to the individual; and communicating at least one environmental mitigation strategy to a system user.

Figure 44:
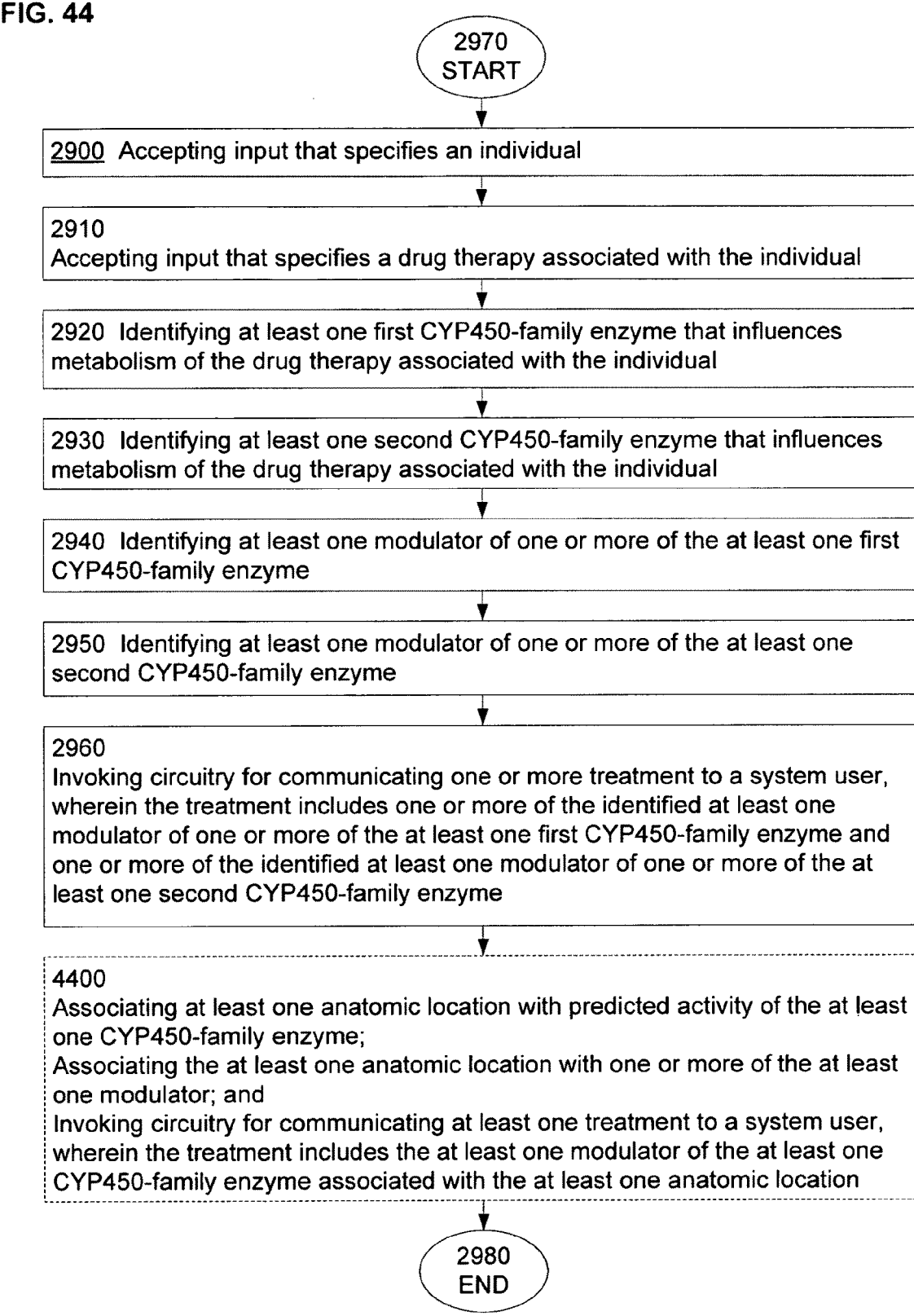
FIG. 44 is a flowchart depicting aspects of a method such as the one shown in FIG. 29.

FIG. 44 illustrates aspects of a method as shown in FIG. 29. A method diagram may include block 4400, showing: associating at least one anatomic location with predicted activity of the at least one CYP450-family enzyme; associating the at least one anatomic location with one or more of the at least one modulator; and invoking circuitry for communicating at least one treatment to a system user, wherein the treatment includes the at least one modulator of the at least one CYP450-family enzyme associated with the at least one anatomic location.

Figure 45:
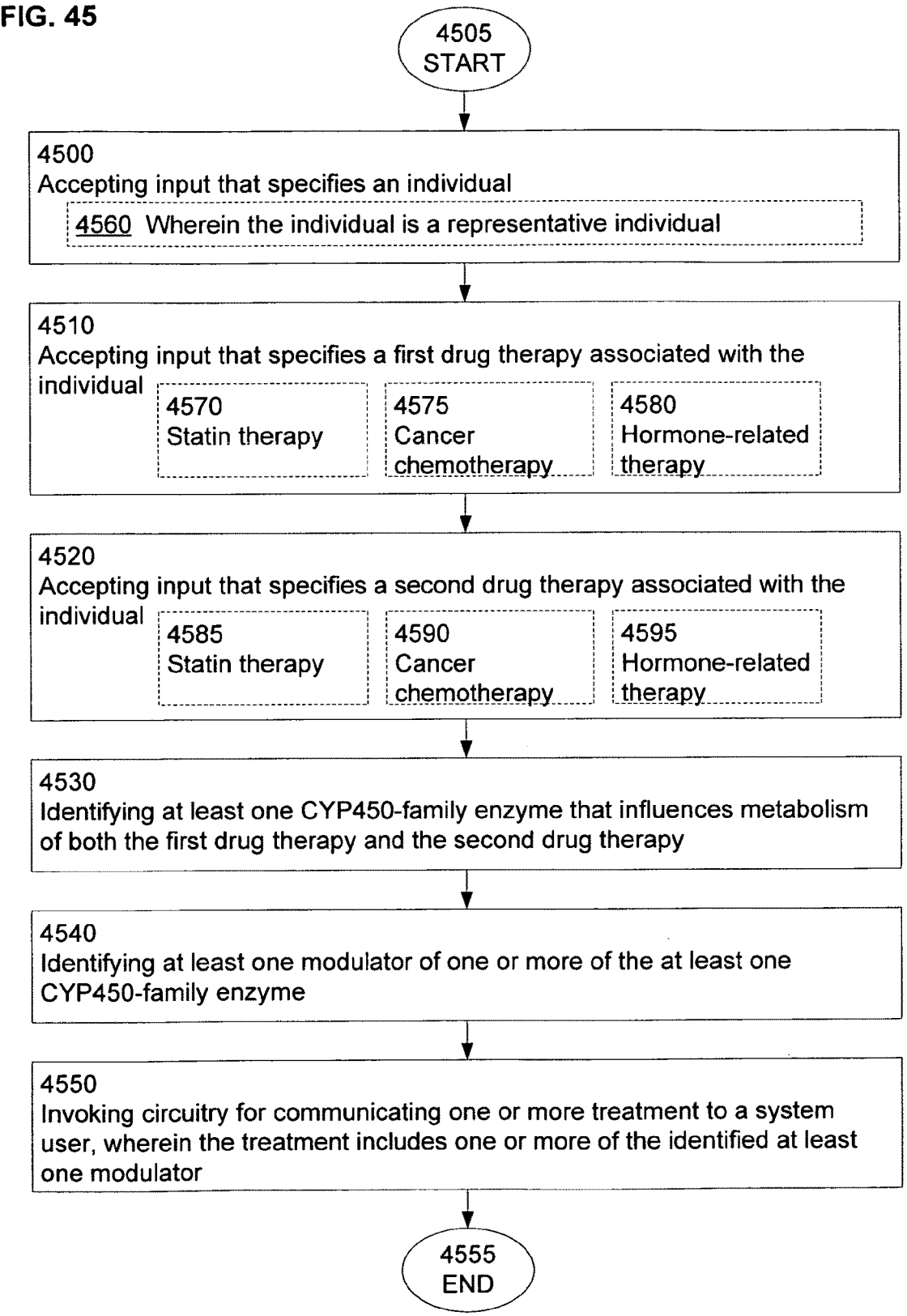
FIG. 45 is a flowchart illustrating aspects of a method.

FIG. 45 depicts aspects of a method. A method start is depicted as block 4505. Method block 4500 illustrates accepting input that specifies an individual. Method block 4500 may include method block 4560 showing wherein the individual is a representative individual. Method block 4100 illustrates accepting input that specifies a first drug therapy associated with the individual. Method block 4510 may include at least one of blocks 4570, 4575 and 4580. Method block 4570 shows wherein the first drug therapy associated with the individual is a statin therapy. Method block 4575 illustrates wherein the first drug therapy associated with the individual is a cancer chemotherapy. Method block 4580 depicts wherein the first drug therapy associated with the individual is a hormone-related therapy. Method block 4520 shows accepting input that specifies a second drug therapy associated with the individual. Method block 4520 may include at least one of block 4585, 4590 and 4595. Method block 4590 illustrates wherein the input that specified a second drug therapy associated with the individual specifies a statin therapy. Method block 4590 depicts wherein the input that specified a second drug therapy associated with the individual specifies a cancer chemotherapy. Method block 4595 shows wherein the input that specified a second drug therapy associated with the individual specifies a hormone-related therapy. Method block 4530 illustrates identifying at least one CYP450-family enzyme that influences metabolism of both the first drug therapy and the second drug therapy. Method block 4540 depicts identifying at least one modulator of one or more of the at least one CYP450-family enzyme. Method block 4550 shows invoking circuitry for communicating one or more treatment to a system user, wherein the treatment includes one or more of the identified at least one modulator. The end of the method is depicted as block 4555.

Figure 46:
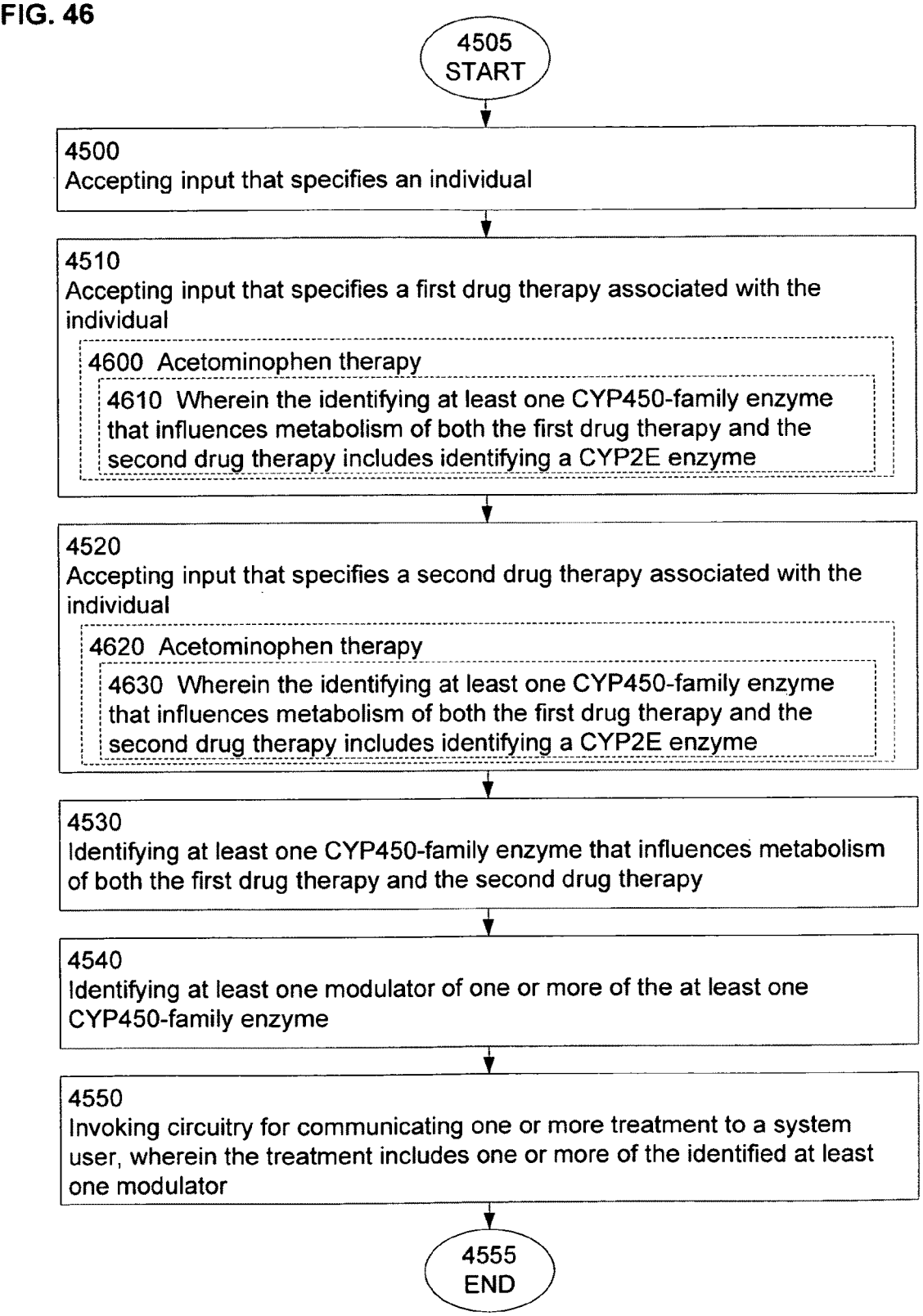
FIG. 46 is a flowchart showing aspects of a method such as the one depicted in FIG. 45.

FIG. 46 illustrates aspects of a method diagram as shown in FIG. 45. Block 4510, depicting accepting input that specifies a first drug therapy associated with the individual, may include block 4600, showing wherein the first drug therapy associated with the individual identifies an acetominophen therapy. Block 4600 may include block 4610, depicting wherein the identifying at least one CYP450-family enzyme that influences metabolism of both the first drug therapy and the second drug therapy includes identifying a CYP2E enzyme. Block 4520, showing accepting input that specifies a second drug therapy associated with the individual, may include block 4620, showing wherein the second drug therapy associated with the individual identifies an acetominophen therapy. Block 4620 may include block 4630, depicting wherein the identifying at least one CYP450-family enzyme that influences metabolism of both the first drug therapy and the second drug therapy includes identifying a CYP2E enzyme.

Figure 47:
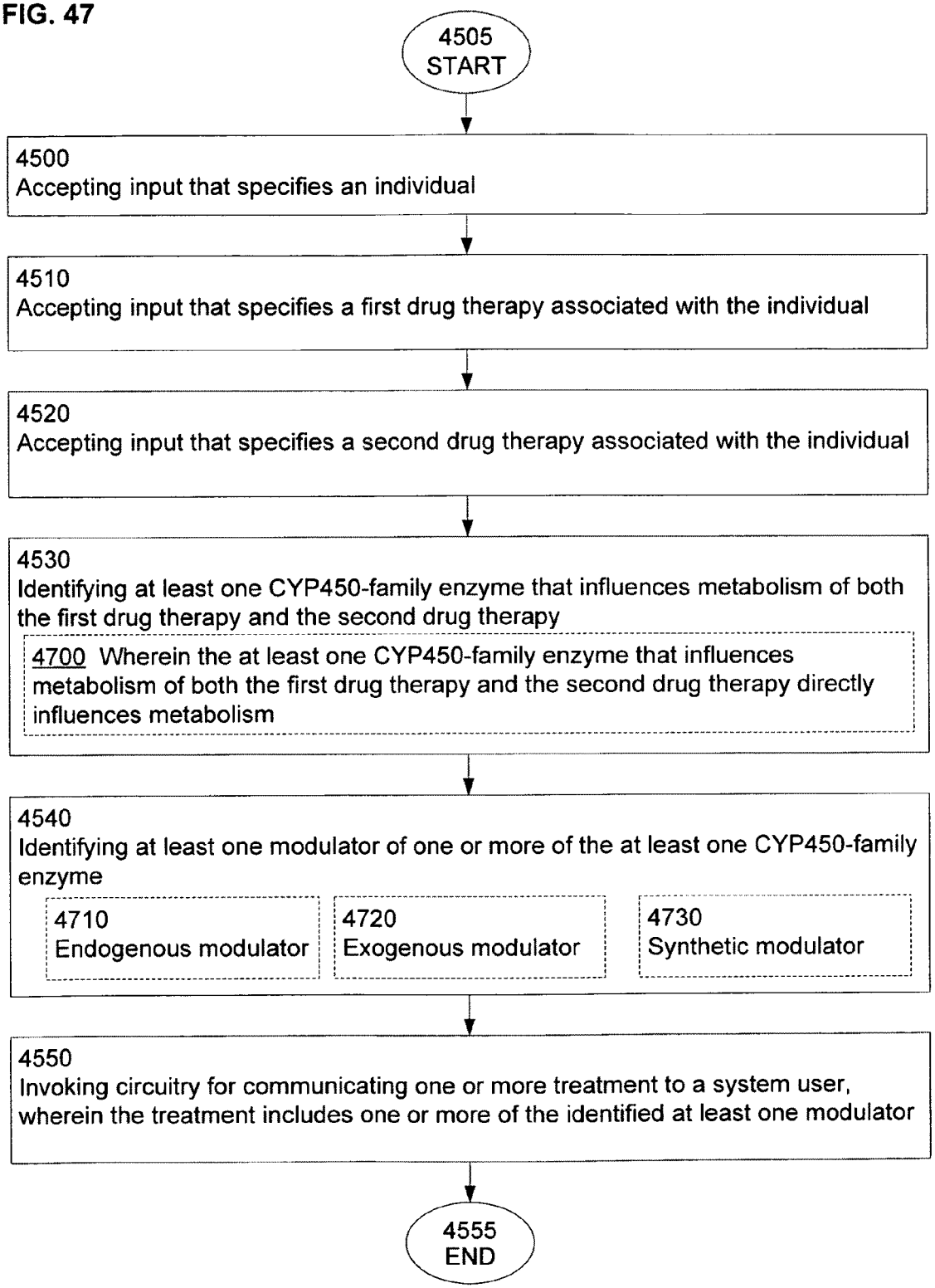
FIG. 47 is a flowchart depicting aspects of a method such as the one illustrated in FIG. 45.

FIG. 47 illustrates aspects of a method diagram as shown in FIG. 45. Block 4530, showing identifying at least one CYP450-family enzyme that influences metabolism of both the first drug therapy and the second drug therapy, may include block 4700, wherein the at least one CYP450-enzyme that influences metabolism of both the first drug therapy and the second drug therapy directly influences metabolism. In some aspects, a method includes wherein the at least one CYP450-enzyme that influences metabolism of both the first drug therapy and the second drug therapy indirectly influences metabolism. Method block 4540, depicting identifying at least one modulator of one or more of the at least one CYP450-family enzyme, may include at least one of blocks 4710, 4720 and 4730. Method block 4710 shows wherein the at least one modulator of one or more of the at least one CYP450-family enzyme is an endogenous modulator. Method block 4720 depicts wherein the at least one modulator of one or more of the at least one CYP450-family enzyme is an exogenous modulator. Method block 4730 illustrates wherein the at least one modulator of one or more of the at least one CYP450-family enzyme is a synthetic modulator.

Figure 48:
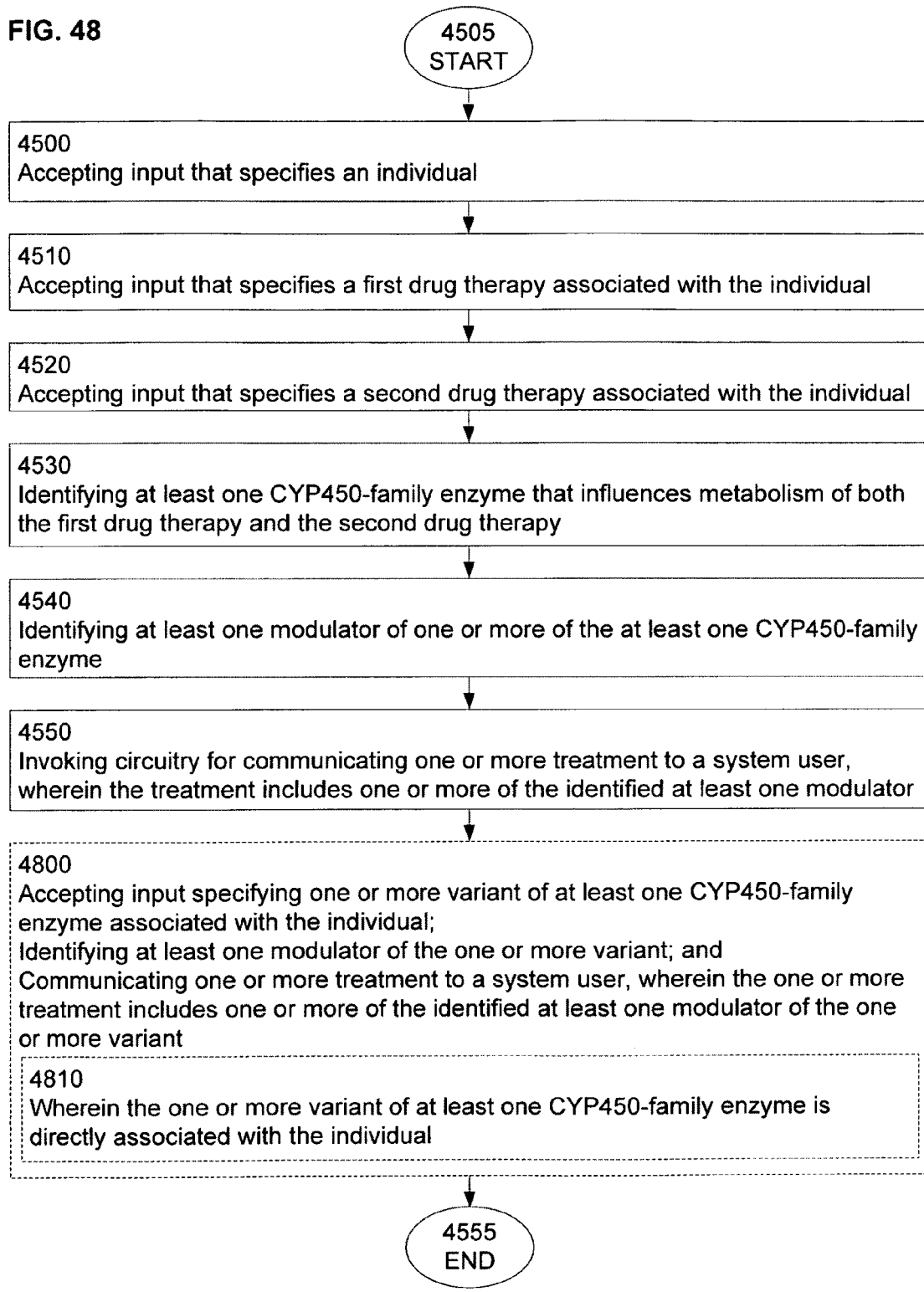
FIG. 48 is a flowchart showing aspects of a method such as the one depicted in FIG. 45.

FIG. 48 illustrates aspects of a method diagram as depicted in FIG. 45. Some diagrams may include block 4800, illustrating: accepting input specifying one or more variant of at least one CYP450-family enzyme associated with the individual; identifying at least one modulator of the one or more variant; and communicating one or more treatment to a system user, wherein the one or more treatment includes one or more of the identified at least one modulator of the one or more variant. Block 4800 may include block 4810, depicting wherein the one or more variant of at least one CYP450-family enzyme is directly associated with the individual. A method diagram may include a block depicting wherein the one or more variant of at least one CYP450-family enzyme is indirectly associated with the individual.

Figure 49:
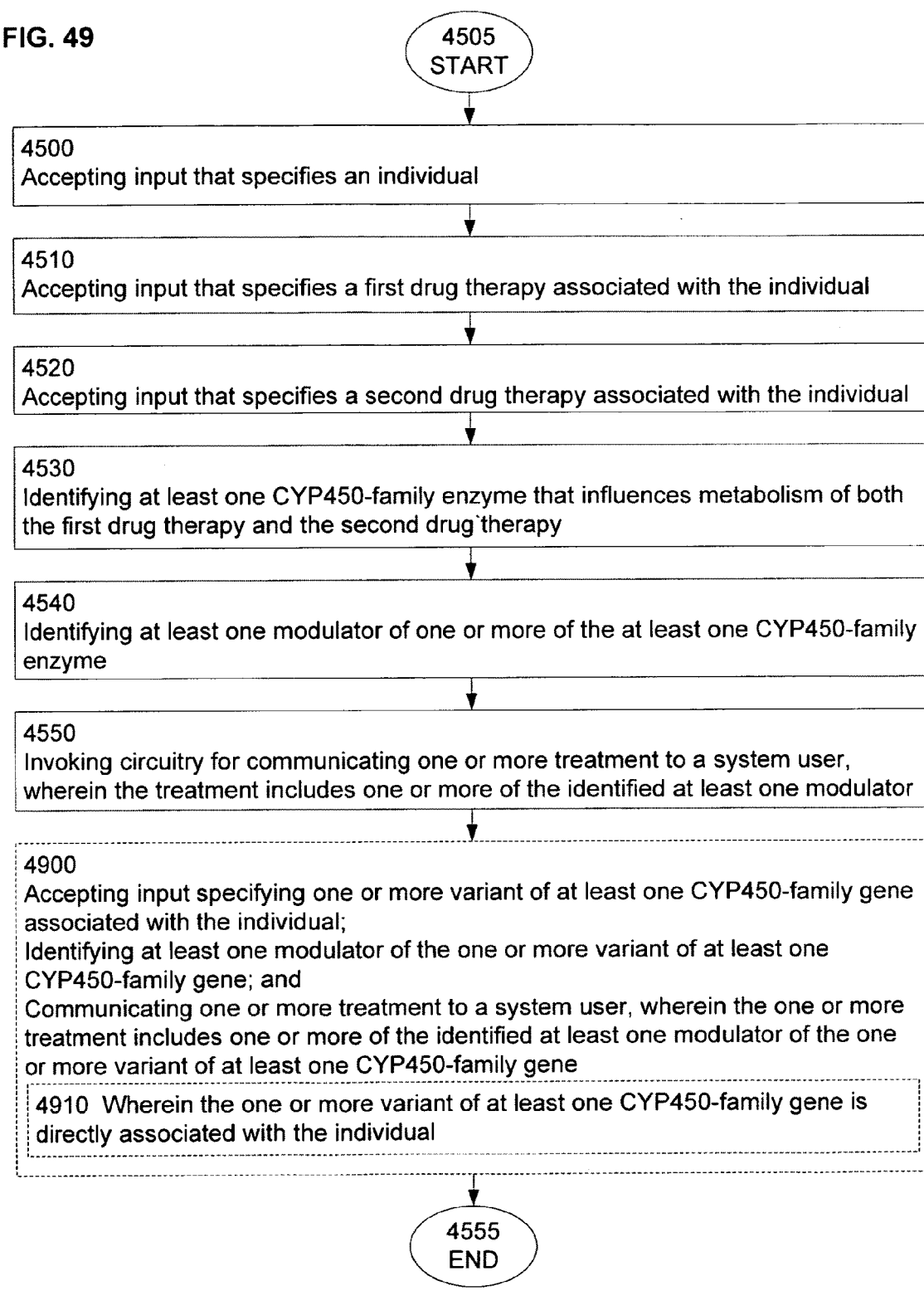
FIG. 49 is a flowchart depicting aspects of a method such as the one illustrated in FIG. 45.

FIG. 49 depicts aspects of a method diagram as shown in FIG. 45. A diagram may include block 4900, showing: accepting input specifying one or more variant of at least one CYP450-family gene associated with the individual; identifying at least one modulator of the one or more variant of at least one CYP450-family gene; and communicating one or more treatment to a system user, wherein the one or more treatment includes one or more of the identified at least one modulator of the one or more variant of at least one CYP450-family gene. Block 4900 may include block 4910, illustrating wherein the one or more variant of at least one CYP450-family gene is directly associated with the individual. A method diagram may include a block wherein the one or more variant of at least one CYP450-family gene is indirectly associated with the individual.

Figure 50:
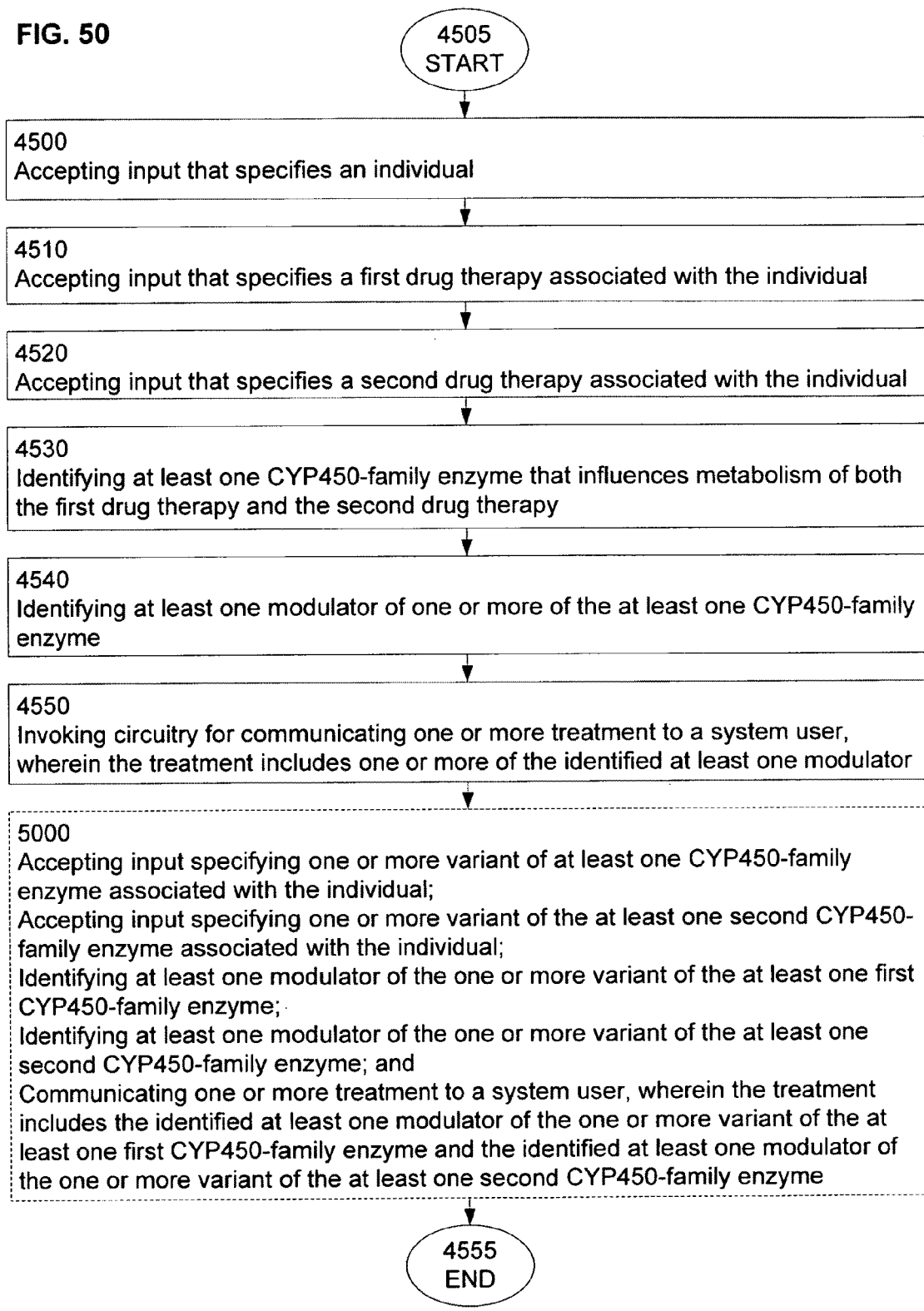
FIG. 50 is a flowchart showing aspects of a method such as the one depicted in FIG. 45.

FIG. 50 illustrates aspects of a method diagram such as shown in FIG. 45. A method diagram may include block 5000, illustrating: accepting input specifying one or more variant of at least one CYP450-family enzyme associated with the individual; accepting input specifying one or more variant of the at least one second CYP450-family enzyme associated with the individual; identifying at least one modulator of the one or more variant of the at least one first CYP450-family enzyme; identifying at least one modulator of the one or more variant of the at least one second CYP450-family enzyme; and communicating one or more treatment to a system user, wherein the treatment includes the identified at least one modulator of the one or more variant of the at least one first CYP450-family enzyme and the identified at least one modulator of the one or more variant of the at least one second CYP450-family enzyme.

Figure 51:
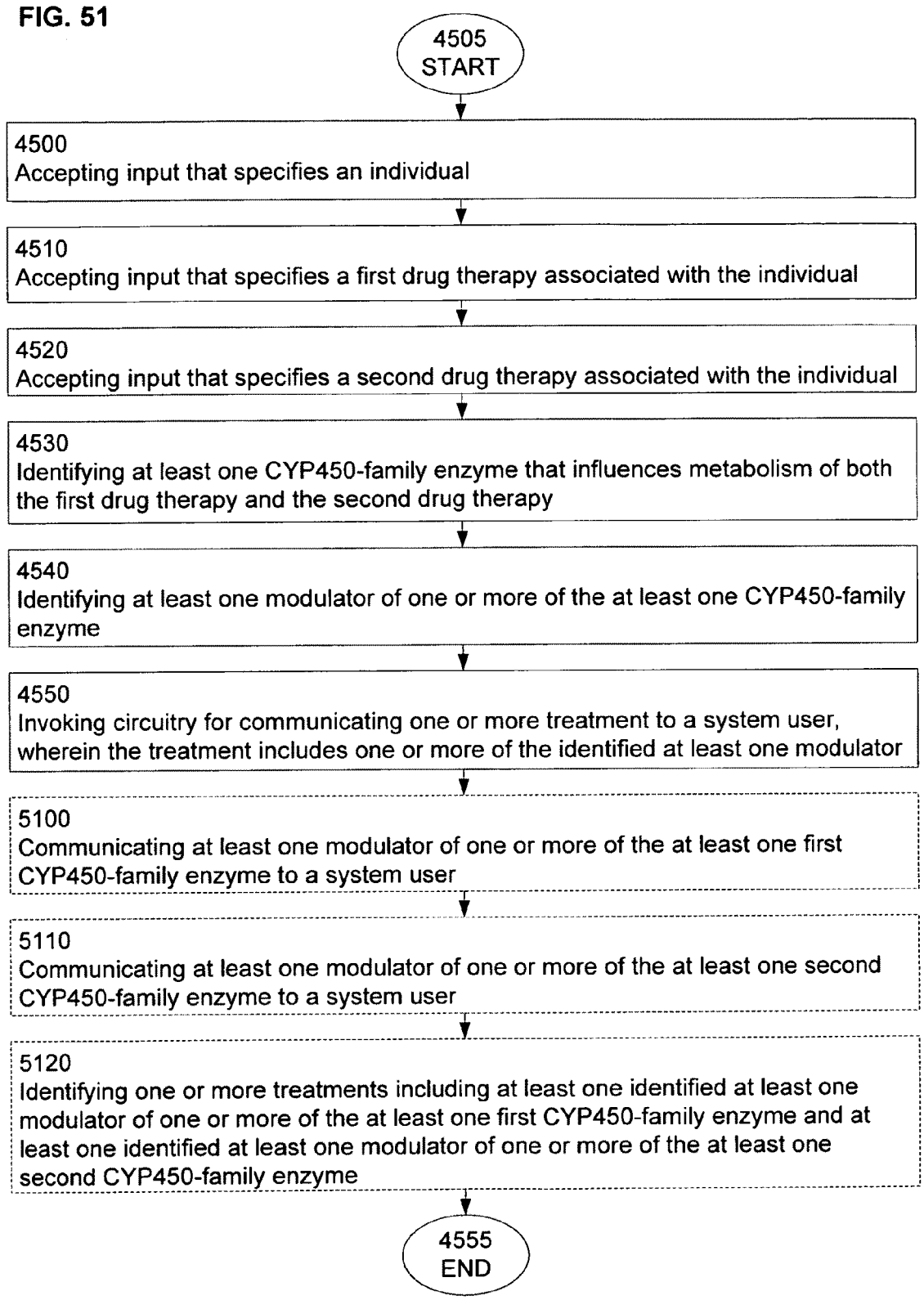
FIG. 51 is a flowchart depicting aspects of a method such as the one illustrated in FIG. 45.

FIG. 51 depicts aspects of a method diagram such as illustrated in FIG. 45. A method diagram may include one or more of blocks 5100, 5110 and 5120. Block 5100 depicts communicating at least one modulator of one or more of the at least one first CYP450-family enzyme to a system user. Block 5110 shows communicating at least one modulator of one or more of the at least one second CYP450-family enzyme to a system user. Block 5120 illustrates identifying one or more treatments including at least one identified at least one modulator of one or more of the at least one first CYP450-family enzyme and at least one identified at least one modulator of one or more of the at least one second CYP450-family enzyme.

Figure 52:
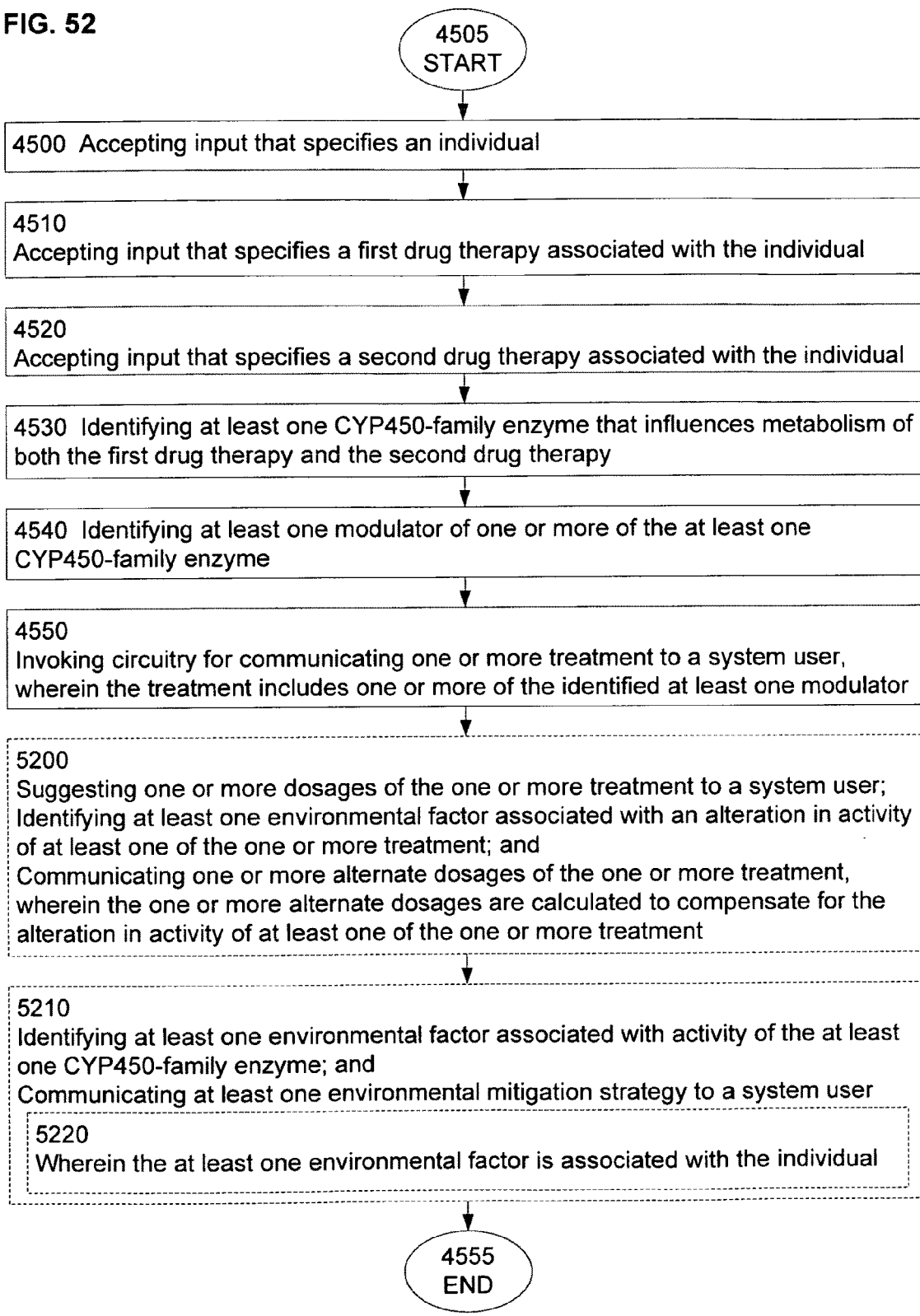
FIG. 52 is a flowchart showing aspects of a method such as the one depicted in FIG. 45.

FIG. 52 illustrates aspects of a method diagram as depicted in FIG. 45. A diagram may include block 5200, illustrating: suggesting one or more dosages of the one or more treatment to a system user; identifying at least one environmental factor associated with an alteration in activity of at least one of the one or more treatment; and communicating one or more alternate dosages of the one or more treatment, wherein the one or more alternate dosages are calculated to compensate for the alteration in activity of at least one of the one or more treatment. A diagram may include block 5210, depicting: identifying at least one environmental factor associated with activity of the at least one CYP450-family enzyme; and communicating at least one environmental mitigation strategy to a system user. Block 5210 may include block 5220, illustrating wherein the at least one environmental factor is associated with the individual.

Figure 53:
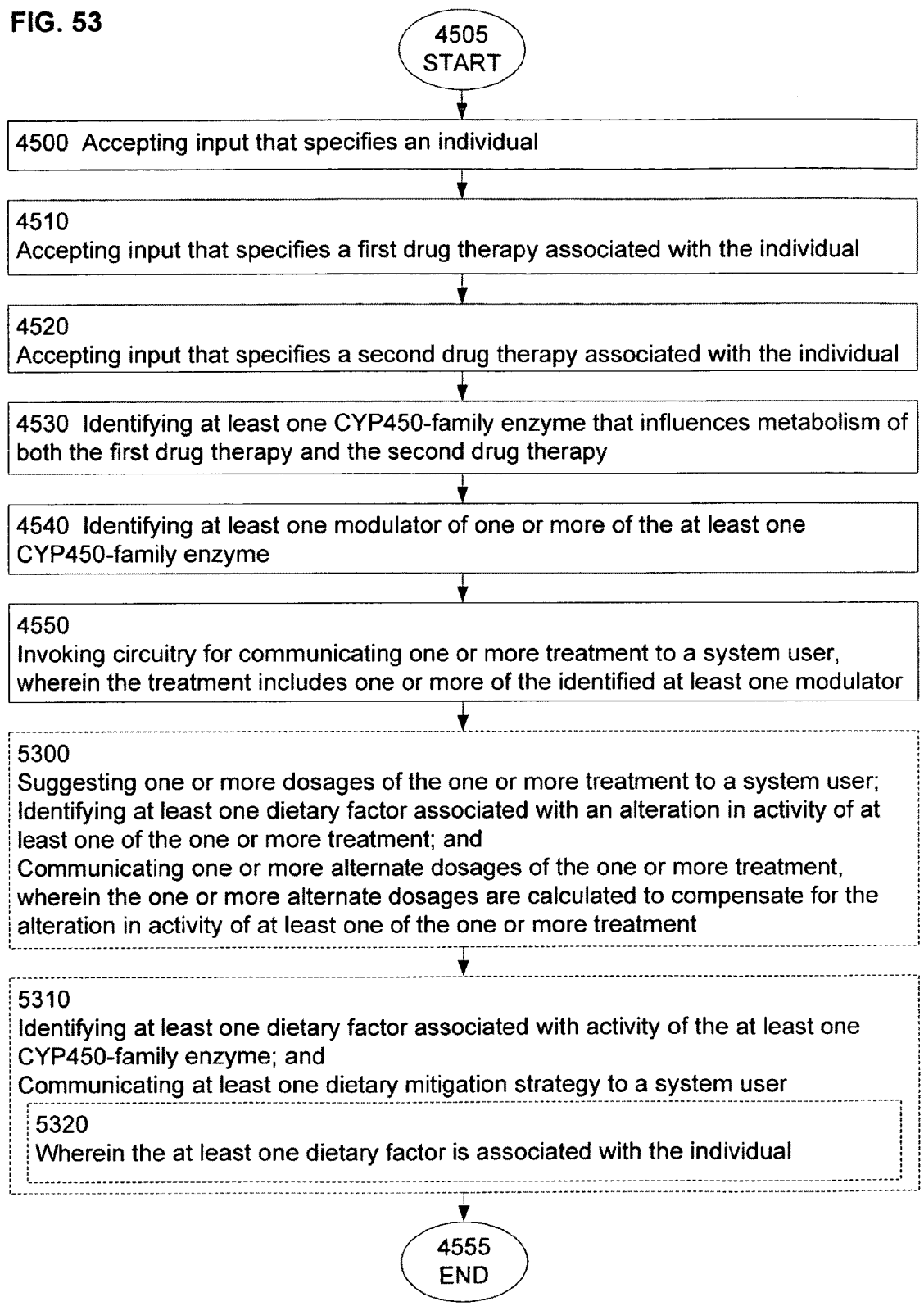
FIG. 53 is a flowchart depicting aspects of a method such as the one illustrated in FIG. 45.

FIG. 53 shows aspects of a method diagram such as depicted in FIG. 45. A diagram may include block 5300, showing: suggesting one or more dosages of the one or more treatment to a system user; identifying at least one dietary factor associated with an alteration in activity of at least one of the one or more treatment; and communicating one or more alternate dosages of the one or more treatment, wherein the one or more alternate dosages are calculated to compensate for the alteration in activity of at least one of the one or more treatment. A diagram may include block 5310, depicting: identifying at least one dietary factor associated with activity of the at least one CYP450-family enzyme; and communicating at least one dietary mitigation strategy to a system user. Block 5310 may include block 5320, showing wherein the at least one dietary factor is associated with the individual.

Figure 54:
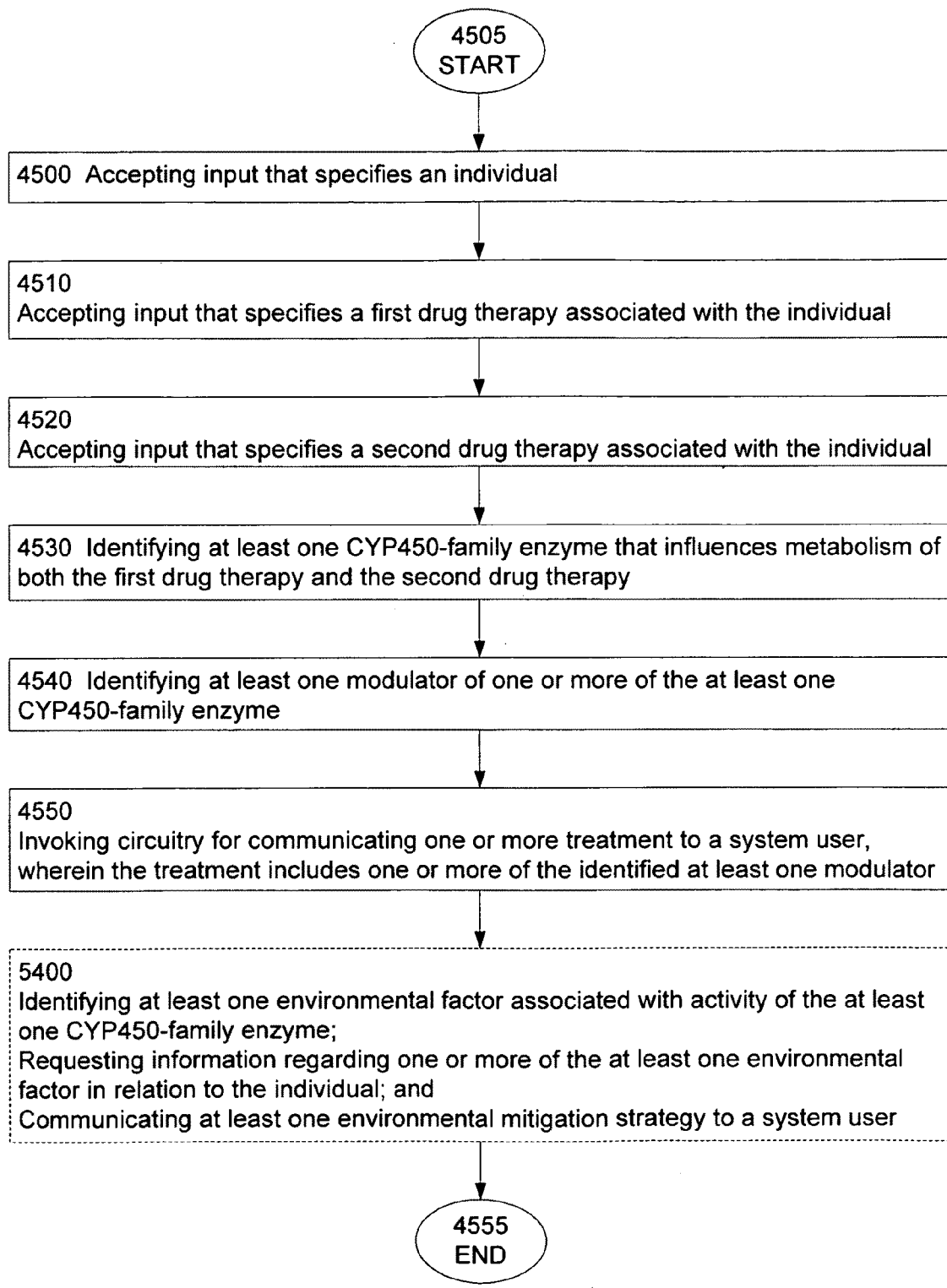
FIG. 54 is a flowchart showing aspects of a method such as the one depicted in FIG. 45.

FIG. 54 depicts aspects of a method diagram as shown in FIG. 45. A diagram may include block 5400, showing: identifying at least one environmental factor associated with activity of the at least one CYP450-family enzyme; requesting information regarding one or more of the at least one environmental factor in relation to the individual; and communicating at least one environmental mitigation strategy to a system user.

Figure 55:
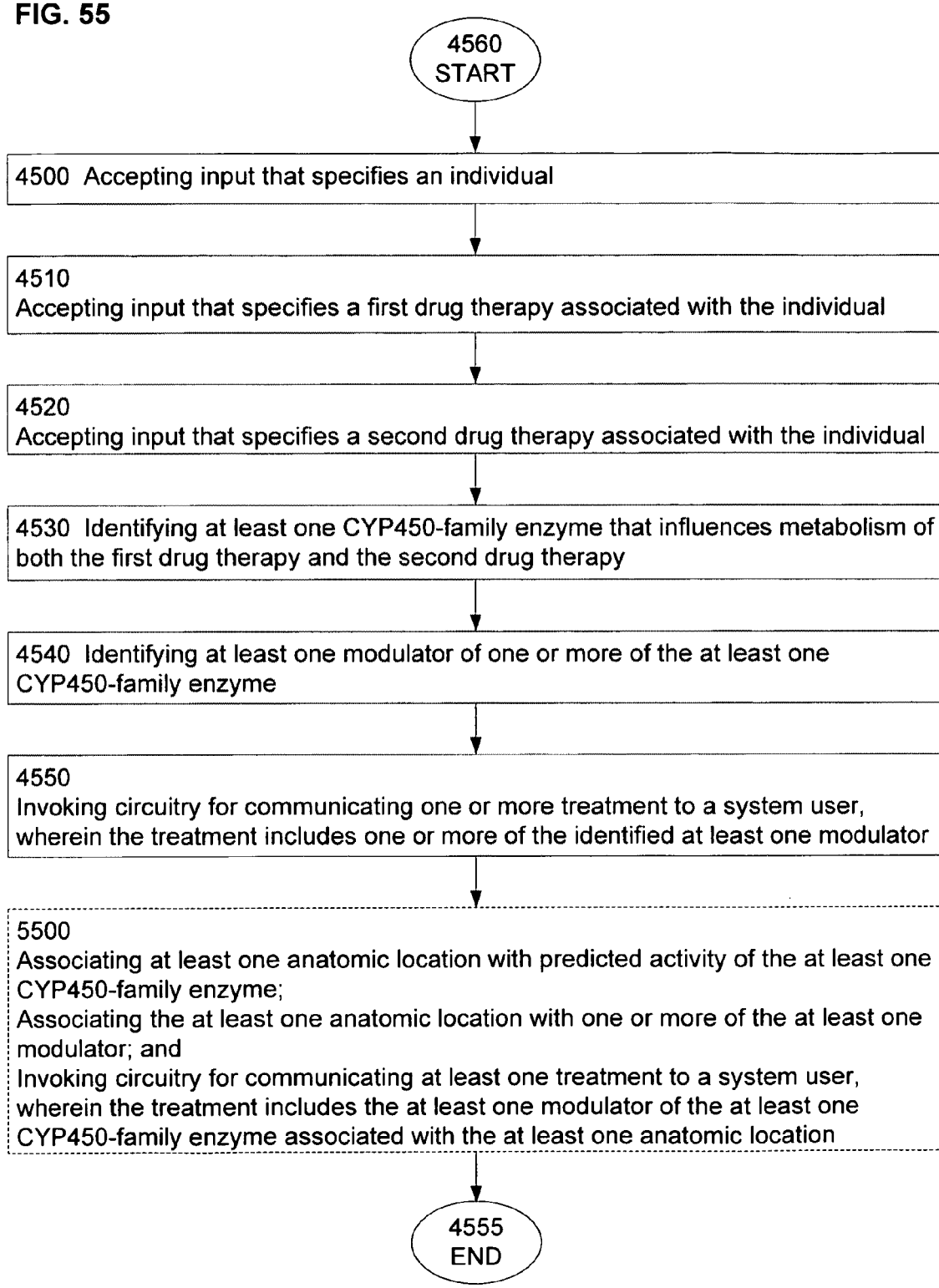
FIG. 55 is a flowchart showing aspects of a method such as the one depicted in FIG. 45.

FIG. 55 shows aspects of a method diagram as depicted in FIG. 45. A diagram may include block 5500, showing: associating at least one anatomic location with predicted activity of the at least one CYP450-family enzyme; associating the at least one anatomic location with one or more of the at least one modulator; and invoking circuitry for communicating at least one treatment to a system user, wherein the treatment includes the at least one modulator of the at least one CYP450-family enzyme associated with the at least one anatomic location.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware. vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit a device detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, C++ or other code sequences can be compiled or implemented in high-level descriptor languages (e.g., a logic-synthesizable language, a hardware description language, a hardware design simulation, and/or other such similar mode(s) of expression). For example, some or all of the logical expression may be manifested as a Verilog-type hardware description or other circuitry model before physical implementation in hardware. Those skilled in the art will recognize how to obtain, configure, and optimize suitable transmission or computational elements, material supplies, actuators, or other structures in light of the teachings herein.

The foregoing detailed description has set forth various embodiments of the devices and/or processes via the use of block diagrams, flowcharts, and/or examples. Insofar as such block diagrams, flowcharts, and/or examples contain one or more functions and/or operations, and each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various aspects described herein which can be implemented, individually and/or collectively, by a wide range of hardware, software, firmware, and/or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). As used herein, "circuitry" includes, but is not limited to, optical, chemical, biological-based, or wireless circuitry. As used herein "circuitry" includes, but is not limited to, solid-state or integrated circuitry. As used herein, "circuitry" includes, but is not limited to, analog, digital, or mixed-signal circuitry. Further, the subject matter described herein may be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

It is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory). Further, implementation of at least part of a system for performing a method in one territory does not preclude use of the system in another territory. A sale of a system or method may likewise occur in a territory even if components of the system or method are located and/or used outside the territory.

Aspects of the systems and methods described herein may be illustrated by the following non-limiting examples.

EXAMPLES

Example 1

Methods and systems such as those described herein may be used to aid medical providers in making decisions regarding treatments and giving relevant advice to patients. For example, prescription of histamine H1 receptor antagonists (antihistamines) for the treatment of allergic disease may be complicated by common side effects, including cognitive impairment and sedation. The sedative effect of the antihistamine diphenhydramine has been correlated with its plasma concentration (e.g. plasma levels greater than 50 ng/ml correlate with a sedative effect; see Carruthers et al, Correlation between plasma diphenhydramine level and sedative and antihistamine effects, Clin. Pharmacol. Ther. 23: 375-382, 1978; which is herein incorporated by reference). A system may accept input from a system user, such as a physician or other medical provider, that specifies an individual undergoing medical consultation and further accepts input identifying diphenhydramine as associated with that individual. For example, a system user may provide input specifying that an individual takes diphenhydramine regularly, is currently taking diphenhydramine, or that diphenhydramine may be suggested by the medical provider. A system may include or be connected to a database containing information regarding diphenhydramine, for example, the CYP450-family enzymes that influence metabolism of diphenhydramine, modulators of the CYP450-family enzymes, and treatments including these modulators. A system may identify that diphenhydramine undergoes metabolism (N-demethylation) catalyzed by multiple CYP450-family enzymes including: CYP2D6, CYP1A2, CYP2C9 and CYP2C19 (Akutsu et al, Identification of human cytochrome P450 isozymes involved in diphenhydramine N-demethylation, Drug Metabolism Disposition 35:72-78, 2007; herein incorporated by reference). Furthermore a system may identify that although CYP2D6 is the most active enzyme of the CYP450-family in N-demethylation of diphenhydramine (e.g. recombinant CYP2D6 specific activity=0.69 pmol/min/pmol P450 versus CYP2C19 specific activity=0.071 pmol/min/pmol P450) the relative contributions of CYP2D6 and other CYP450-family enzymes to total N-demethylation activity vary considerably between individuals. For example in human liver microsomes, the specific CYP contributions to total N-demethylation activity vary between individuals. See Table 1 (information taken from Akutsu et al, Ibid.).

TABLE 1

Contribution of CYP isozymes to total diphenhydramine N-demethylation activity in liver microsomes from different individuals.

| Subject | % Total Diphenhydramine N-demethylation Activity | | | |
| --- | --- | --- | --- | --- |
| | CYP2D6 | CYP1A2 | CYP2C9 | CYP2C19 |
| HG30 | 0 | 31.6 | 45.9 | 22.5 |
| HG66 | 81.3 | 4.1 | 13.4 | 1.2 |
| HG89 | 4.6 | 36.0 | 32.1 | 27.4 |
| HG112 | 12.1 | 4.2 | 35.8 | 47.9 |
| pooled | 48.4 | 14.2 | 27.5 | 9.9 |

In addition, the system may identify that CYP2D6 exhibits extensive variability between individuals derived mainly from genetic variants that influence enzyme expression and function. To illustrate, over 60 different variant alleles of CYP2D6 have been described (Oscarson et al, Pharmacogenetics of drug metabolizing enzymes: importance for personalized medicine, Clin. Chem. Lab. Med. 41: 573-580, 2003; herein incorporated by reference). The system also may identify CYP450-family enzyme variants that are associated with little or no metabolism of diphenylhydramine, such as those variants (often called "null alleles") that do not encode functional CYP2D6 proteins. Information regarding CYP450-family enzyme variants may be obtained, for example, from genotyping assays for the seven most common inactive alleles (CYP2D6*3, *4, *5,*6, *7, *8, *16) which predict a poor metabolizer phenotype in Caucasians with >99% sensitivity (Oscarson, Ibid.). Methods to determine a genotype for CYP2D6 may include the AmpliChip (AmpliChip CYP Test Package Insert (October 2007), Roche Molecular Systems, Inc., Pleasanton, Calif., which is herein incorporated by reference). An individual's DNA (obtained from, for example, white blood cells from a peripheral blood sample or epithelial cells from a cheek swab) may be tested for the presence of at least 29 variants of the CYP2D6 gene. (See Kalra, Cytochrome P450 enzyme isoforms and their therapeutic implications: an update, Indian J. Med. Sci. 61: 102-116, 2007; incorporated by reference herein). Individuals associated with poor metabolizer CYP450-family enzyme variants are at risk of adverse drug interactions due to prolonged, elevated plasma levels of drugs that are poorly metabolized. Alternatively an individual associated with an ultra-rapid metabolizer CYP450-family enzyme variant, characterized by duplication of CYP2D6 genes and elevated levels of CYP2D6 enzyme, may experience rapid metabolism of drugs such as diphenhydramine and loss of therapeutic benefit or a need for higher dosage (Zanger et al, Cytochrome P450 2D6: overview and update on pharmacology, genetics, biochemistry, Naunyn Schmiedebergs Arch. Pharmacol. 369: 23-37, 2004; incorporated by reference herein). Methods and systems described herein may identify information regarding substrate specificity, genotype and metabolizer CYP450-family enzyme variants and recommend a drug or combination of drugs, recommend dosage, and avoid adverse drug interactions.

Example 2

Methods and systems may identify multiple substrates and modulators for many CYP450-family enzymes. Examples of substrates and modulators with specificity for individual CYP450-family enzymes (e.g. CYP2D6, CYP1A2, CYP2C9, and CYP2C19) are shown in Table 2 (information taken from Akutsu et al, Ibid.). More complete lists of substrates and modulators, including inhibitors and inducers, that are common to multiple CYP450-family enzymes or unique to individual CYP450-family enzymes can be found in Kalra, Ibid. For example, CYP1A2 and CYP2D6 both metabolize tricyclic amines (e.g. amitriptyline) and modulators are known that induce or inhibit the specific CYP450-family enzymes: quinidine inhibits CYP2D6 and dexamethasone induces CYP2D6; furafylline inhibits CYP1A2 and cyclobenzaprine induces CYP1A2 (Kalra, Ibid.). Methods and systems may identify CYP450-family enzyme substrate and modulator specificities for communication to a system user, including recommending treatments and approaches to avoid adverse drug interactions. For example, methods and systems might communicate treatments wherein amitryptiline is not given in combination with fluoxetine.

TABLE 2

Specific substrates and inhibitors of CYP isozymes

| CYP450-Family Enzyme | Substrate | Inhibitor |
| --- | --- | --- |
| CYP2D6 | Bufuralol 1'-hydroxylation | Quinidine |
| CYP1A2 | Phenacetin O-deethylation | Furafylline |
| CYP2C9 | Diclofenac 4'-hydroxylation | Sulfaphenazole |
| CYP2C19 | (S)-Mephenytoin 4'-hydroxylation | Omeprazole |

Fluoxetine inhibits CYP2D6 and therefore it inhibits amitryptiline metabolism, and promotes increased plasma concentrations of amitryptiline and potential toxicity. In some situations, an alternative to fluoxetine may be recommended as part of a treatment. One example of an alternative to fluoxetine is fluvoxamine, which is a weak inhibitor of CYP2D6 (Kalra, Ibid.). The methods and systems described herein may identify CYP450-family enzyme substrate specificity, CYP450-family enzymes, genes and variants, metabolizer phenotypes, and modulators to aid medical caregivers in prescribing treatments and giving advice.

Example 3

Methods and systems described herein may identify CYP450-family enzymes that influence metabolism of specific statins. For example, atorvastatin, cerivastatin, lovastatin and simvastatin are metabolized primarily by CYP3A4; fluvastatin is metabolized mainly by CYP2C9; cerivastatin is metabolized by CYP3A4 and CYP2C8 and pravastatin is not extensively metabolized (Beaird, J. HMG-CoA reductase inhibitors: assessing differences in drug interactions and safety profiles, Am. Pharm. Assoc. 40: 637-644, 2000; incorporated by reference herein). Systems and methods may also identify CYP450-family enzyme modulators, for example inhibitors (e.g. itraconazole, erythromycin, cimetidine) and inducers, that influence the metabolism of statins. Systems and methods may identify treatments that include modulators that inhibit CYP450-family enzymes, and therefore result in reduced statin metabolism, leading to elevated blood concentrations of statins and adverse effects such as rhabdomyolysis and myopathy. In some embodiments, methods and systems such as those described herein may be implemented to avoid suggesting treatments associated with adverse effects to some individuals. The methods and systems described herein may aid a health caregiver in the prescription of statins, at least one second drug and CYP450-family modulators (e.g. rifampin) to avoid drug interactions and maximize therapeutic benefit to an individual.

For example, methods and systems may accept input that identifies simvastatin as associated with an individual, and identify the CYP450-family enzyme CYP3A4 as significantly involved in the metabolism of simvastatin. Methods and systems may further identify itraconazole (an anti-fungal agent) as a modulator with an inhibitory effect on CYP3A4. In some situations, methods and systems may accept input that identifies itraconazole as a drug therapy associated with an individual. The system may communicate a warning against coadministration of itraconazole with simvastatin to avoid an adverse drug interaction and toxic effects such as rhabdomyolysis (Beaird, Ibid.). A system may include a database or access a database including information from clinical studies that show itraconazole coadministered with simvastatin significantly increases the serum concentration of simvastatin and its active metabolite, simvastatin acid (Neuvonen et al, Simvastatin but not pravastatin is very susceptible to interaction with the CYP3A4 inhibitor itraconazole, Clin. Pharmacol. Ther. 63: 332-341, 1998; incorporated by reference herein). Itraconazole (relative to placebo) increases the peak serum concentrations (Cmax) and the areas under the serum concentration-time curve [AUC (0-infinity)] of simvastatin and simvastatin acid at least tenfold (p<0.001). Methods and systems may also accept input associating another statin, pravastatin, as associated with an individual, and identify that pravastatin is not metabolized by CYP3A4 and is not appreciably affected by coadministratin of itraconazole. Itraconazole slightly increased the AUC (0-infinity) and Cmax of pravastatin relative to placebo, but the changes were statistically nonsignificant (P=0.052 and 0.172, respectively), and the plasma half-life was not altered (Neuvonen et al, Ibid.). The methods and systems described herein may identify CYP3A4 substrate specificities (e.g. CYP3A4 metabolizes simvastatin but not pravastatin) and identify CYP modulators (e.g. itraconazole inhibits CYP3A4) and communicate selection of treatments including pravastatin or another statin (for example fluvastatin) not metabolized by CYP3A4 for combination with itraconazole.

Alternatively, given the association of a specific statin with an individual, systems and methods may communicate treatments containing alternate dosages to compensate for alteration in activity of the treatment at standard dosages. Systems and methods may communicate treatments allowing coadministration of interacting drugs at optimal dosages and schedules to avoid toxicity. For example, individual patients may require treatment with both simvastatin and itraconazole (antifungal) because of allergic reactions or toxicity derived from alternative statins (e.g. fluvastatin or pravastatin), and a lack of suitable alternative antifungal drugs (e.g. fluconazole and ketoconazole both inhibit CYP3A4). Methods and systems may identify an increase in simvastatin Cmax, AUC, half-life and accumulation when coadminstered with itraconazole and therefore communicate a reduced dosage and altered schedule of simvastatin administration to a system user. In some instances, dosage and schedule recommendations based on pharmacokinetic data have been established for interacting drugs (e.g. amiodarone and S-warfarin; Kalra, Ibid.) and may be included in databases accessed by a system.

Methods and systems such as those described herein may communicate treatments including many drugs that modulate CYP3A4 by inhibition, which could lead to elevated blood simvastatin concentrations and simvastatin-associated adverse effects when coadministered with simvastatin. For example, patients taking simvastatin with clarithromycin, diltiazem, nefazodone, mibefradil or cyclosporine experience rhabdomyolysis and myopathy (Beaird, Ibid.), and each of these drugs inhibits the enzyme activity of CYP3A4. Methods and systems may identify CYP3A4 substrate specificities and modulator identities to allow selection of statins, second drugs and modulators that will not interact adversely. The identity of multiple CYP450-family enzyme substrates, inhibitors, and inducers are well known in the art, see for example, a Wikipedia entry for "Cytochrome P450" which was downloaded on Nov. 7, 2008, and is incorporated by reference herein.

Example 4

Methods and systems such as those described herein may be relevant to the oral bioavailability of ingested drug treatments. For example, the CYP450-family enzyme CYP3A, particularly CYP3A4, has been shown to be part of an interaction in the intestine that regulates oral bioavailability of some drugs (see Benet and Cummins, The drug efflux-metabolism alliance: biochemical aspects, Advanced Drug Delivery reviews 50:S3-11, 2001, and Hunter and Hirst, Intestinal secretion of drugs, the role of P-glycoprotein and related drug efflux systems in limiting oral drug absorption, Advanced Drug Delivery Reviews 25:129-157, 1997, which are herein incorporated by reference). Methods and systems such as those disclosed herein may access information, such as may be contained within a database or a look-up table, of dietary factors, for example grapefruit juice and starfruit, and their effects on CYP3A4 activity, to aid in prescribing drugs and advising patients to avoid inhibition of CYP3A4 metabolic activity and elevated systemic levels of coadministered drugs that are primarily metabolized by CYP3A4. For example, CYP3A4 present in the small intestine metabolizes dihydropyrimidines (calcium channel antagonists including: felodipine, nimodipine, nifedipine, amlodipine and others) after ingestion. Inhibition or reduction of CYP3A4 activity in the small intestine by components in grapefruit juice may result in increased bioavailability of felodipine, and lead to increased Cmax and AUC values. In turn, elevated systemic (plasma) felodipine levels result in lowered blood pressure, rapid heart beat and vasodilation-related adverse events. Furthermore, the effects of grapefruit juice on felodipine metabolism vary considerably between individuals. The change in AUC and Cmax values for felodipine range between 0 and six-fold for individuals coadministered grapefruit juice versus water. However the effects are reproducible for single individuals, and individual differences are in part explained by variants in the innate level of CYP3A4 activity in the small intestine (Bailey et al, Grapefruit juice-drug interactions, Br. J. Clin. Pharmacol. 46: 101-110, 1998; which is herein incorporated by reference). Methods and systems such as those described herein may associate CYP3A4 innate activity levels with individuals and identify information regarding grapefruit juice inhibition of CYP3A4 so as to communicate an optimal felopidine dosage and dosage schedule as well as to warn against grapefruit juice consumption.

Methods and systems may also identify the inhibition of CYP3A4 activity by grapefruit juice and recommend a dosage schedule for consumption of grapefruit juice and felopidine to avoid adverse interactions. For example, clinical studies have shown that the half-life for a "grapefruit juice effect" on the AUC of felopidine to be 12 hours. Grapefruit juice consumed 24 hours prior to taking felopidine has been shown to have a reduced but measurable effect on felopidine pharmacokinetics (Bailey et al, Ibid.). Moreover, methods and systems may access information regarding dihydropyrmidines with low oral bioavailability, such as those that are extensively metabolized in the small intestine, that are affected most by grapefruit juice consumption. For example, nisoldipine and amlodipine are dihydropyridines with very low and very high innate oral bioavailability respectively. The percentage change in Cmax values for nisoldipine and amlodipine when given with grapefruit juice are 409% and 115% respectively as compared to water (Bailey et al, Ibid.). Methods and systems may identify, for example, CYP3A4 substrate specificities, an individual's innate level of CYP3A4 metabolic activity (e.g. CYP450-family enzyme variants and genes), the inherent bioavailability of dihydropyrimidines, and the identity of dietary factors (e.g. grapefruit juice) with modulating CYP3A4 metabolic activity. Methods and systems can recommend avoiding those dietary factors that interact with a dihydropyrimidine or, if necessary, choosing alternate drugs with limited potential for drug interaction. Methods and systems may also identify other dietary factors that modulate CYP450-family enzymes and variants, including CYP3A enzymes, such as pomegranates, star fruit, and St John's wort. System knowledge of: CYP3A substrate specificities, CYP3A genotype, metabolic phenotype (e.g. poor metabolizer), and dietary factors that modulate CYP3A activity will aid a caregiver (e.g. physician, nutritionist) in advising patients to avoid these dietary factors in combination with drugs metabolized by CYP3A (e.g. statins, erythromycin, and benzodiazepines). For more information regarding CYP3A4 activity, including substrates and modulators such as inhibitors and inducers of CYP3A4, see the Wikipedia entry titled "CYP3A4," downloaded on Nov. 7, 2008, and incorporated by reference herein.

Example 5

Methods and systems such as those described herein may be used to advise caregivers on the prescription of chemotherapy drugs. Methods and systems such as those described herein may be useful since the pharmacokinetics of cancer chemotherapy drugs is highly variable between individuals and the therapeutic window for many cancer drugs is very narrow. Methods and systems may identify or accept input regarding: CYP450-family enzymes that influence metabolism of cancer chemotherapy drugs; CYP450-family enzymes, enzyme variants and genes from an individual; and modulators of CYP450-family enzymes that influence metabolism of the cancer chemotherapy drugs. Methods and systems such as those described herein may aid prescription of preferred anticancer drugs at an optimal dosage and help avoid prescription of drugs that interact, for example in a way that leads to toxicity and adverse events. Methods and systems may identify specific CYP450-family enzymes associated with metabolizing anticancer drugs, such as cyclophosphamide, ifosfamide, etoposide, teniposide, tamoxifen, taxol (paclitaxel) and vinca alkaloids, based on data obtained in vitro with human liver microsomes (see Kivisto et al, The role of human cytochrome p450 enzymes in the metabolism of anticancer agents: implications for drug interactions, Br. J. Clin. Pharmacol. vol. 40, pp. 523-530, (1995); incorporated by reference herein).

In some embodiments, methods and systems such as those described herein may be used to identify modulators targeted toward a specific group of cells, such as a group of cancer cells with increased activity of at least one CYP450-family enzyme. For example, see McFadyen et al., Cytochrome P450 CYP1B1 activity in renal cell carcinoma, British Journal of Cancer, 91, 966-971, 2004, which is incorporated by reference herein.

Systems and methods such as those described herein may identify competitive inhibitors of the CYP450-family enzymes that metabolize anticancer drugs, and the $K_i$ (inhibition constant) values for the CYP450 family enzyme modulators which assist in predicting the likelihood of a significant in vivo interaction. For example, inhibition is likely to occur in vivo if the steady-state concentration of a modulator with inhibitory properties is similar to the $K_i$ value, or greater (Kivisto et al, Ibid.). In some situations, methods and systems may accept input regarding CYP2D6 genotype (e.g. "null alleles") and phenotype (e.g. poor metabolizer) associated with an individual to aid in communicating an optimal dosage of tamoxifen for treatment of estrogen receptor positive breast cancer.

In addition, methods and systems may accept input regarding an individual's CYP2D6 phenotype to aid in the prescription and dosage of antiemetic drugs such as tropisetron and odansetron, which are also metabolized by CYP2D6 (Omari et al, Pharmacogenetics of the cytochrome P450 enzyme system: review of current knowledge and clinical significance, J. Pharm Pract. vol. 20, pp. 206-218 (2007), which is incorporated by reference herein).

Methods and systems such as those described herein may identify CYP2D6 substrates such as tamoxifen and active metabolites such as endoxifen that have greatly enhanced anticancer activity to aid in the prescription of modulators to inhibit or induce CYP2D6 activity. For example, breast cancer patients with a poor metabolizer phenotype or intermediate metabolizer phenotype may require a CYP2D6 inducer, for example, a piperidine or carbamazepine, to increase metabolism of tamoxifen to its active metabolite, endoxifen.

Methods and systems such as those described herein may also identify that the induction of CYP2D6 activity may increase the metabolism of some antiemetics (e.g. tropisetron and odansetron) thereby reducing benefit from the antiemetics. Moreover methods and systems can communicate adjusted dosages and/or schedules of tropisetron or help prescribe alternate antiemetics that are not substrates for CYP2D6. The methods and systems described herein can communicate one or more treatments of cancer chemotherapy to a health caregiver (e.g. physician) that can include CYP450-family enzyme modulators and CYP450-family enzyme substrates.

Example 6

Methods and systems such as those described herein may assist medical personnel in the treatment of lupus nephritis patients. For example, methods and systems may be useful for caregivers prescribing cyclophosphamide pulse therapy to mitigate the low response rates and gonadal toxicity, which are common problems associated with this treatment. Methods and systems such as those described herein may identify cyclophosphamide as a prodrug that requires activation by CYP450-family enzymes to be active, and may identify multiple CYP450-family enzymes that metabolize cyclophosphamide including: CYP2A6, CYP2B6, CYP2C19, CYP2C9, CYP3A4, and CYP3A5. Moreover, a subset, including CYP2B6, CYP2C19, CYP2C9 and CYP3A5, may be identified that are genetically polymorphic with variant alleles that have little or no metabolic activity (e.g. CYP2C19*2 and CYP2C19*3 have little or no enzymatic activity). Information about CYP450-family enzyme substrate specificity and enzymatic activity may be obtained from in vitro studies with liver microsomes or recombinant cell lines (see, for example, Roy et al, Development of a substrate-activity based approach to identify the major human liver P-450 catalysts of cyclophosphamide and ifosfamide activation based on cDNA-expressed activities and liver microsomal P-450 profiles, Drug Metab. Disp. vol. 27, pp 655-666 (1999), which is incorporated by reference herein). A system may accept input regarding CYP450-family enzyme genotypes for individuals that is based on results from assays using the polymerase chain reaction and genomic DNA (Takada et al, Cytochrome P450 pharmacogenetics as a predictor of toxicity and clinical response to pulse cyclophosphamide in lupus nephritis, Arthr. Rheum. vol. 50, pp. 2202-2210 (2004), which is incorporated by reference herein).

The methods and systems described herein may help health caregivers to prescribe drugs, drug combinations and drug dosages that increase the probability for clinical response and reduce the likelihood of toxicity for individuals. Methods and systems such as those described herein may include information obtained from clinical studies associating and correlating clinical response and toxicity with CYP450-family enzyme genotype. For example, individual lupus nephritis patients homozygous or heterozygous for CYP2C19*2 (a "null allele") have a reduced risk (relative risk 0.10) for ovarian failure following pulse cyclophosphamide therapy. However, patients homozygous for CYP2B6*5 or CYP2C19*2 have a higher probability (P=0.0005) of progressing to end stage renal disease and a lower probability (P=0.051) of achieving a complete renal response (Takada et al, Ibid.), results which are assumed to result from a failure to metabolize and activate cyclophosphamide. Methods and systems such as those described herein may accept input relating to CYP450-family enzyme genotype (e.g. CYP2C 19*2 heterozygosity) and identify CYP450-family enzyme substrate specificity (e.g. CYP2C19 and CYP2B6 metabolize cyclophosphamide) as well as identifying modulators of CYP450-family enzyme activity (e.g. ritonavir inhibits CYP2C19). Methods and systems may further communicate to a caregiver recommendations for prescription of drugs, drug dosages, and CYP450-family enzyme modulators that have a higher probability of achieving a clinical response (e.g. renal response) and a lower probability of being toxic (e.g. ovarian failure).

Example 7

Methods and systems such as those described herein may be useful to aid in prescription of drugs and giving advice to patients based in part on the information that the CYP450-family enzyme CYP2E1 is an important enzyme for liver toxicity, and that modulation of CYP2E1 activity can reduce liver toxicity (see Cederbaum, CYP2E1—Biochemical and toxicological aspects and role in alcohol-induced liver injury, Mount Sinai Journal of Medicine, 73(4) 657-672, 2006, which is herein incorporated by reference). Methods and systems may incorporate information regarding many substrates that CYP2E1 metabolizes and activates, including ethanol, acetaminophen, carbon tetrachloride and N-nitrosodimethylamine. In some situations, the metabolism of substrates by CYP2E1 may yield more toxic products than the substrate itself. Methods and systems may identify modulators of CYP2E1 activity, for example ethanol (an inducer) and other modulators (e.g. isoniazid, phenobarbital and rifampin). Methods and systems may also incorporate information regarding chronic alcohol consumption, which increases the risk of acetaminophen toxicity as alcohol-induced CYP2E1 activity increases risk for the production of toxic metabolites derived from acetaminophen. Methods and systems may incorporate data from methods and assays measuring the relative level of CYP2E1 activity in human hepatocytes using a CYP2E1-specific substrate, chlorzoxazone, as described (e.g. Madan et al, Effects of protypical microsomal enzyme inducers on Cytochrome P450 expression in cultured human hepatocytes, DMD 31: 21-31, 2003; incorporated by reference herein). For example, human liver microsomes stored frozen at −80° C. with 0.25 M sucrose may be assayed for protein content with a BCA Protein Assay Kit (Pierce Chem. Co., Rockford, Ill.; the manual for which is hereby incorporated by reference). Fifty microgram aliquots of human liver microsome protein may be assayed in a total volume of 1 ml at 37° C. and chlorzoxazone-6 hydroxalase activity may be measured with 15, 30 and 120 micromolar chlorzoxazone (see e.g. Robertson et al, In Vitro inhibition and induction of human hepatic Cytochrome P450 enzymes by modafinil, DMD 28: 664-671, 2000; incorporated by reference herein). Alternatively, methods and systems may incorporate information resulting from assays of the level of CYP2E1 activity in individuals determined by orally administering 500 mg of chlorzoxazone and taking venous blood samples over a 10 hr period, followed by calculations of areas under the curve of plasma concentration versus time (AUC) of chlorzoxazone and 6-OHchlorzoxazone. The 6-OHchlorzoxazone/chlorzoxazone concentration ratio at t=2 hr is a simple and non-traumatic marker of CYP2E1 induction (Girre et al, Assessment of Cytochrome P4502E1 induction in alcoholic patients by chlorzoxazone pharmacokinetics, Biochem. Pharmacol. 47: 1503-08, 1994; incorporated by reference herein). Methods and systems may incorporate information regarding CYP2E1 enzymatic activity and identify modulators of CYP2E1 activity that, for example, would inhibit CYP2E1 activity and avoid generation of toxic metabolites from acetaminophen or ethanol in patients with hepatic toxicity.

Methods and systems disclosed herein may associate substrates and modulators recognized by CYP2E1 based in part on data obtained from in vitro assays using human hepatocytes (Madan et al, Ibid.; Robertson et al, Ibid.; Kalra, Ibid.). For example, Table 3 lists some known substrates, inhibitors, and inducers of CYP2E1. To avoid toxicity or to treat toxicity due to CYP2E1 metabolic activity, methods and systems may identify CYP2E1 substrates and modulators as well as communicate treatments to lower the level of toxic metabolites. For example, if an individual chronically consumes alcohol and also takes acetaminophen, then at least two substrates for CYP2E1 are present in that individual's body. In some situations, ethanol may be identified as a modulator as it may act to induce CYP2E1 activity (see Dai and Cederbaum, Inactivation and degradation of human Cytochrome P4502E1 by $CCl_4$ in a transfected Hep62 cell line, The Journal of Pharmacology and Experimental Therapeutics, 275, 1614-1622 (1995), which is incorporated by reference herein). The methods and systems described herein can identify interaction of ethanol and acetaminophen and recommend a reduction in ethanol consumption and an alternative to acetaminophen to reduce substrate levels. Methods and systems may communicate treatment including modulation of CYP2E1 activity with a specific modulator that inhibits activity, for example, disulfram, as well as reduction of the CYP2E1 inducer, ethanol.

TABLE 3

Substrates and Modulators of CYP2E1*

| Substrate | Inhibitor | Inducer |
|---|---|---|
| Acetaminophen | Disulfuram | Ethanol |
| Chlorzoxazone | 4-Methylpyrazole | Isoniazid |
| Ethanol | Diethyldithiocarbamate | Phenobarbital |
| Enflurane | Diallylsulfide | Rifampin |
| Halothane | Phenethylisothiocyanate | Acetone |
| Isoflurane | | |
| N-Nitrosodimethylamine | | |
| Carbon tetrachloride | | |
| Tamoxifen | | |

*Data taken from: Kalra et al, Ibid.; Madan et al, Ibid.; Jaeschke et al, FORUM mechanisms of hepatotoxicity, Toxicological Sciences, 65, 166-176 (2001), which are incorporated by reference herein.

Example 8

Methods and systems described herein may aid healthcare providers in prescribing treatments and advising patients. For example, methods and systems may incorporate information regarding CYP450-family enzymes present in hepatic and non-hepatic tissues including normal and cancerous tissues derived from kidney, prostate, breast, and small intestine. The suggestion of treatments for cancer and other diseases may be improved in situations where systems and methods may incorporate information, for example regarding hepatic and extra-hepatic CYP450-family enzymes, the substrates they recognize (including endogenous and exogenous substrates), the modulators (inhibitors and inducers) that affect their activity, and individual variation of CYP450-family enzymes (i.e. genotype and phenotype).

For example, methods and systems may identify CYP1B1, an extra-hepatic CYP450-family enzyme frequently overexpressed in tumor tissues (e.g. renal cell cancer, prostate cancer, and breast cancer), and associate CYP1B1 with anticancer drugs that are metabolized by CYP1B1 (e.g. docetaxel, tamoxifen, mitoxantrone). Overexpression of CYP1B1 in tumors is associated with resistance to docetaxel cytotoxicity (Rodriquez-Antona et al, Cytochrome P450 pharmacogenetics and cancer, Oncogene vol. 25, pp. 1679-1691 (2006), which is incorporated by reference herein). Methods and systems may communicate treatments (either localized to the tumor or systemic) including CYP1B1 modulators (e.g. inhibitors such as alpha-naphthoflavone) in combination with an anticancer drug such as docetaxel. Methods and systems may also accept input regarding CYP1B1 variants (for example, at least seven mutant CYP1B1 genes have been identified) and associate these variants with their respective metabolic phenotypes (e.g. capacity to metabolize substrates such as estradiol and tamoxifen; Rodriquez-Antona et al, Ibid.). Methods and systems may accept input regarding patient-specific data (e.g. CYP1B1 genotype, current medications, tumor-associated CYP1B1 enzyme activity) and identify CYP450-family enzyme substrates, CYP450-family enzyme modulators and CYP450-family enzyme tissue localization to communicate a preferred combination of anticancer drug and CYP450-family enzyme modulators at an optimal dosage and schedule.

For example, methods and systems may identify CYP450-family enzymes, their substrates and their modulators that are associated with producing cancer-promoting metabolites. The substrates and modulators may derive from environmental, pharmaceutical or endogenous sources. For example, CYP1B1 is present in mammary cells and hydroxylates estradiol to 4-hydroxy-estradiol which, in turn, can be oxidized to a quinone form (3,4-catechol estradiol quinone) that is genotoxic and a putative tumor promoter (Coumol et al, Differential regulation of Cytochrome P450 1A1 and 1B1 by a combination of dioxin and pesticides in the breast tumor cell line MCF-7, Cancer Research, 61, 3942-3948 (2001), which is incorporated by reference herein). CYP1B1 and some of its polymorphic variants are associated with breast cancer (Hanna et al, Cytochrome P450 1B1 (CYP1B1) pharmacogenetics: association of polymorphisms with functional differences in estrogen hydroxylation activity, Cancer Research 60, 3440-3444 (2000) which is incorporated by reference herein; Omari et al, Ibid.) By contrast, CYP1A1 acts on estradiol to yield 2-hydroxy estradiol, which as a quinone form is not genotoxic and not considered to be a tumor promoter. Moreover, the ratio of CYP1B1 to CYP1A1 activity is a determinant of the metabolism and toxicity of estradiol in mammary cells (Coumol et al, Ibid.).

Methods and systems identifying environmental modulators of CYP1B1 and CYP1A1 can help a healthcare provider prescribe medication and give advice, especially in conjunction with therapies involving estrogens (e.g. hormone replacement therapy) and exposure to pesticides and herbicides that may have xenoestrogenic activity in vivo (such as a-endosulfan, furans). For example, exposure of mammary epithelial cells to dioxin stimulates expression of both CYP1A1 and CYP1B1, but both estrogens (e.g. estradiol used for HRT) and xenoestrogens (e.g. pesticides such as endosulfan) differentially reduce gene expression of CYP1A1 (Coumol et al, Ibid.), thereby increasing CYP1B1 metabolism of estradiol to 4-hydroxy estradiol and oxidation to the quinone form that is genotoxic and tumorigenic. Therefore individuals exposed to herbicides such as dioxin and individuals receiving hormone replacement therapy (e.g. estrogen) may be at increased risk for breast cancer (Coumol et al, Ibid.) and benefit from receiving CYP modulators. For example the system may communicate a recommendation for an inhibitor of CYP1B1 (e.g. alpha-napthoflavone) and advice against administration of hormone replacement therapy with estrogens during or following exposure to xenoestrogenic pesticides and herbicides.

With respect to the use of substantially any plural and/or singular terms herein, the reader can translate from the plural to the singular and/or from the singular to the plural as is appropriate to the context and/or application. The various singular/plural permutations are not expressly set forth herein for sake of clarity.

All of the herein-referenced U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

The herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

While particular aspects of the present subject matter described herein have been shown and described, changes and modifications may be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

The various aspects and embodiments disclosed herein are for purposes of illustration and are not intended to be limiting, with the true scope and spirit being indicated by the following claims.

What is claimed is:

1. A method comprising:
accepting input that specifies an individual;
accepting input that identifies a drug therapy associated with the individual;
identifying at least one first CYP450-family enzyme that influences metabolism of the drug therapy associated with the individual;
identifying at least one second CYP450-family enzyme that influences metabolism of the drug therapy associated with the individual;
identifying at least one modulator of one or more of the at least one first CYP450-family enzyme;
identifying at least one modulator of one or more of the at least one second CYP450-family enzyme; and
invoking circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme.

2. The method of claim 1, comprising:
suggesting one or more dosages of the one or more treatment to a system user;
identifying at least one environmental factor associated with an alteration in activity of at least one of the one or more treatment; and
communicating one or more alternate dosages of the one or more treatment to a system user, wherein the one or more alternate dosages are calculated to compensate for the alteration in activity of at least one of the one or more treatment.

3. The method of claim 1, comprising:
suggesting one or more dosages of the one or more treatment to a system user;
identifying at least one dietary factor associated with an alteration in activity of at least one of the one or more treatment; and
communicating one or more alternate dosages of the one or more treatment to a system user, wherein the one or more alternate dosages are calculated to compensate for the alteration in activity of at least one of the one or more treatment.

4. The method of claim 1, comprising:
suggesting one or more dosage schedules of the one or more treatment to a system user;
identifying at least one environmental factor associated with an alteration in activity of at least one of the one or more treatment; and
communicating one or more alternate dosage schedules of the one or more treatment to a system user, wherein the one or more alternate dosage schedules are calculated to compensate for the alteration in activity of at least one of the one or more treatment.

5. The method of claim 1, comprising:
suggesting one or more dosage schedules of the one or more treatment to a system user;
identifying at least one dietary factor associated with an alteration in activity of at least one of the one or more treatment; and communicating one or more alternate dosage schedules of the one or more treatment to a system user, wherein the one or more alternate dosage schedules are calculated to compensate for the alteration in activity of at least one of the one or more treatment.

6. The method of claim 1, comprising:
accepting input specifying one or more variant of at least one CYP450-family enzyme that influences metabolism of the drug therapy associated with the individual;
identifying at least one modulator of at least one of the one or more variant of at least one CYP450-family enzyme; and
communicating one or more treatment to a system user, wherein the treatment includes the identified at least one modulator of at least one of the one or more variant of at least one CYP450-family enzyme.

7. The method of claim 1, comprising:
accepting input specifying one or more variant of at least one CYP450-family gene that influences metabolism of the drug therapy associated with the individual;
identifying at least one modulator of at least one of the one or more variant of at least one CYP450-family gene; and
communicating one or more treatment to a system user, wherein the treatment includes the identified at least one modulator of at least one of the one or more variant of at least one CYP450-family gene.

8. The method of claim 1, comprising:
accepting input specifying one or more variant of the at least one first CYP450-family enzyme that influences metabolism of the drug therapy associated with the individual;
accepting input specifying one or more variant of the at least one second CYP450-family enzyme that influences metabolism of the drug therapy associated with the individual;
identifying at least one modulator of the one or more variant of the at least one first CYP450-family enzyme;
identifying at least one modulator of the one or more variant of the at least one second CYP450-family enzyme; and
communicating one or more treatment to a system user, wherein the treatment includes the identified at least one modulator of the one or more variant of the at least one first CYP450-family enzyme and the identified at least one modulator of the one or more variant of the at least one second CYP450-family enzyme.

9. The method of claim 1, comprising:
identifying at least one environmental factor associated with activity of at least one CYP450-family enzyme that influences metabolism of the drug therapy associated with the individual; and
communicating at least one environmental mitigation strategy to a system user.

10. The method of claim 1, comprising:
identifying at least one dietary factor associated with activity of at least one CYP450-family enzyme that influences metabolism of the drug therapy associated with the individual; and
communicating at least one dietary mitigation strategy to a system user.

11. The method of claim 1, comprising:
associating at least one anatomic location with predicted activity of the at least one first CYP450-family enzyme;
associating the at least one anatomic location with one or more of the at least one modulator of the at least one first CYP450-family enzyme; and
communicating one or more treatment to a system user, wherein the treatment includes one or more of the at least one modulator of the at least one first CYP450-family enzyme associated with the at least one anatomic location.

12. A system, comprising:
circuitry for accepting input that specifies an individual;
circuitry for accepting input that identifies a drug therapy associated with the individual;
circuitry for identifying at least one first CYP450-family enzyme that influences metabolism of the drug therapy associated with the individual;
circuitry for identifying at least one second CYP450-family enzyme that influences metabolism of the drug therapy associated with the individual;
circuitry for identifying at least one modulator of one or more of the at least one first CYP450-family enzyme;
circuitry for identifying at least one modulator of one or more of the at least one second CYP450-family enzyme; and
circuitry for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme.

13. The system of claim 12, comprising:
circuitry for suggesting one or more dosages of the one or more treatment to a system user;
circuitry for identifying at least one environmental factor associated with an alteration in activity of at least one of the one or more treatment; and
circuitry for communicating one or more alternate dosages of the one or more treatment to a system user, wherein the one or more alternate dosages are calculated to compensate for the alteration in activity of at least one of the one or more treatment.

14. The system of claim 12, comprising:
circuitry for suggesting one or more dosages of the one or more treatment to a system user;
circuitry for identifying at least one dietary factor associated with an alteration in activity of at least one of the one or more treatment; and
circuitry for communicating one or more alternate dosages of the one or more treatment to a system user, wherein the one or more alternate dosages are calculated to compensate for the alteration in activity of at least one of the one or more treatment.

15. The system of claim 12, comprising:
circuitry for suggesting one or more dosage schedules of the one or more treatment to a system user;
circuitry for identifying at least one environmental factor associated with an alteration in activity of at least one of the one or more treatment; and
circuitry for communicating one or more alternate dosage schedules of the one or more treatment to a system user, wherein the one or more alternate dosage schedules are calculated to compensate for the alteration in activity of at least one of the one or more treatment.

16. The system of claim 12, comprising:
circuitry for suggesting one or more dosage schedules of the one or more treatment to a system user;
circuitry for identifying at least one dietary factor associated with an alteration in activity of at least one of the one or more treatment; and
circuitry for communicating one or more alternate dosage schedules of the one or more treatment to a system user, wherein the one or more alternate dosage schedules are calculated to compensate for the alteration in activity of at least one of the one or more treatment.

17. The system of claim 12, comprising:
circuitry for accepting input specifying one or more variant of at least one CYP450-family enzyme that influences metabolism of the drug therapy associated with the individual;
circuitry for identifying at least one modulator of at least one of the one or more variant; and
circuitry for communicating one or more treatment to a system user, wherein the treatment includes the identified at least one modulator of at least one of the one or more variant.

18. The system of claim 12, comprising:
circuitry for accepting input specifying one or more variant of at least one CYP450-family gene that influences metabolism of the drug therapy associated with the individual;
circuitry for identifying at least one modulator of at least one of the one or more variant of at least one CYP450-family gene; and
circuitry for communicating one or more treatment to a system user, wherein the treatment includes the identified at least one modulator of at least one of the one or more variant of at least one CYP450-family gene.

19. The system of claim 12, comprising:
circuitry for accepting input specifying one or more variant of the at least one first CYP450-family enzyme that influences metabolism of the drug therapy associated with the individual;
circuitry for accepting input specifying one or more variant of the at least one second CYP450-family enzyme that influences metabolism of the drug therapy associated with the individual;
circuitry for identifying at least one modulator of the one or more variant of the at least one first CYP450-family enzyme;
circuitry for identifying at least one modulator of the one or more variant of the at least one second CYP450-family enzyme; and
circuitry for communicating one or more treatment to a system user, wherein the treatment includes the identified at least one modulator of the one or more variant of the at least one first CYP450-family enzyme and the identified at least one modulator of the one or more variant of the at least one second CYP450-family enzyme.

20. The system of claim 12, comprising:
circuitry for identifying at least one environmental factor associated with activity of at least one CYP450-family enzyme that influences metabolism of the drug therapy associated with the individual; and
circuitry for communicating at least one environmental mitigation strategy to a system user.

21. The system of claim 12, comprising:
circuitry for identifying at least one dietary factor associated with activity of at least one CYP450-family enzyme that influences metabolism of the drug therapy associated with the individual; and
circuitry for communicating at least one environmental mitigation strategy to a system user.

22. The system of claim 12, comprising:
circuitry for associating at least one anatomic location with predicted activity of the at least one first CYP450-family enzyme;
circuitry for associating the at least one anatomic location with one or more of the at least one modulator of the at least one first CYP450-family enzyme; and
circuitry for communicating one or more treatment to a system user, wherein the treatment includes the at least one modulator of the at least one first CYP450-family enzyme associated with the at least one anatomic location.

23. A method comprising:
accepting input that specifies an individual;
accepting input that identifies a first drug therapy associated with the individual;
accepting input that identifies a second drug therapy associated with the individual;
identifying at least one CYP450-family enzyme that influences metabolism of both the first drug therapy and the second drug therapy;
identifying at least one modulator of one or more of the at least one CYP450-family enzyme; and
invoking circuitry for communicating one or more treatment to a system user, wherein the one or more treatment includes one or more of the identified at least one modulator.

24. The method of claim 23, comprising:
accepting input specifying one or more variant of at least one CYP450-family enzyme associated with the individual;
identifying at least one modulator of the one or more variant; and
communicating one or more treatment to a system user, wherein the one or more treatment includes one or more of the identified at least one modulator of the one or more variant.

25. The method of claim 23, comprising:
accepting input specifying one or more variant of at least one CYP450-family gene associated with the individual;
identifying at least one modulator of the one or more variant of at least one CYP450-family gene; and
communicating one or more treatment to a system user, wherein the one or more treatment includes one or more of the identified at least one modulator of the one or more variant of at least one CYP450-family gene.

26. The method of claim 23, comprising:
accepting input specifying one or more variant of the at least one first CYP450-family enzyme associated with the individual;
accepting input specifying one or more variant of the at least one second CYP450-family enzyme associated with the individual;
identifying at least one modulator of the one or more variant of the at least one first CYP450-family enzyme;
identifying at least one modulator of the one or more variant of the at least one second CYP450-family enzyme; and
communicating one or more treatment to a system user, wherein the treatment includes the identified at least one modulator of the one or more variant of the at least one first CYP450-family enzyme and the identified at least one modulator of the one or more variant of the at least one second CYP450-family enzyme.

27. The method of claim 23, comprising:
suggesting one or more dosages of the one or more treatment to a system user;
identifying at least one environmental factor associated with an alteration in activity of at least one of the one or more treatment; and communicating one or more alternate dosages of the one or more treatment, wherein the one or more alternate dosages are calculated to compensate for the alteration in activity of at least one of the one or more treatment.

28. The method of claim 23, comprising:
suggesting one or more dosages of the one or more treatment to a system user;
identifying at least one dietary factor associated with an alteration in activity of at least one of the one or more treatment; and
communicating one or more alternate dosages of the one or more treatment, wherein the one or more alternate dosages are calculated to compensate for the alteration in activity of at least one of the one or more treatment.

29. The method of claim 23, comprising:
identifying at least one dietary factor associated with activity of the at least one CYP450-family enzyme; and
communicating at least one dietary mitigation strategy to a system user.

30. The method of claim 23, comprising:
identifying at least one environmental factor associated with activity of the at least one CYP450-family enzyme;
requesting information regarding one or more of the at least one environmental factor in relation to the individual; and
communicating at least one environmental mitigation strategy to a system user.

31. The method of claim 23, comprising:
associating at least one anatomic location with predicted activity of the at least one CYP450-family enzyme;
associating the at least one anatomic location with one or more of the at least one modulator; and
invoking circuitry for communicating at least one treatment to a system user, wherein the treatment includes the at least one modulator of the at least one CYP450-family enzyme associated with the at least one anatomic location.

32. A system comprising:
circuitry for accepting input that specifies an individual;
circuitry for accepting input that identifies a first drug therapy associated with the individual;
circuitry for accepting input that identifies a second drug therapy associated with the individual;
circuitry for identifying at least one CYP450-family enzyme that influences metabolism of both the first drug therapy and the second drug therapy;
circuitry for identifying at least one modulator of one or more of the at least one CYP450-family enzyme; and
circuitry for communicating one or more treatment to a system user, wherein the one or more treatment includes one or more of the at least one modulator.

33. The system of claim 32, comprising:
circuitry for accepting input specifying one or more variant of at least one CYP450-family enzyme associated with the individual;
circuitry for identifying at least one modulator of the one or more variant; and
circuitry for communicating one or more treatment to a system user, wherein the one or more treatment includes one or more of the identified at least one modulator of the one or more variant.

34. The system of claim 32, comprising:
circuitry for accepting input specifying one or more variant of at least one CYP450-family gene associated with the individual;
circuitry for identifying at least one modulator of the one or more variant of at least one CYP450-family gene; and
circuitry for communicating one or more treatment to a system user, wherein the one or more treatment includes one or more of the identified at least one modulator of the one or more variant of at least one CYP450-family gene.

35. The system of claim 32, comprising:
circuitry for accepting input specifying one or more variant of the at least one first CYP450-family enzyme associated with the individual;
circuitry for accepting input specifying one or more variant of the at least one second CYP450-family enzyme associated with the individual;
circuitry for identifying at least one modulator of the one or more variant of the at least one first CYP450-family enzyme;
circuitry for identifying at least one modulator of the one or more variant of the at least one second CYP450-family enzyme; and
circuitry for communicating one or more treatment to a system user, wherein the treatment includes the identified at least one modulator of the one or more variant of the at least one first CYP450-family enzyme and the identified at least one modulator of the one or more variant of the at least one second CYP450-family enzyme.

36. The system of claim 32, comprising:
circuitry for suggesting one or more dosages of the one or more treatment to a system user;
circuitry for identifying at least one environmental factor associated with an alteration in activity of at least one of the one or more treatment; and
circuitry for communicating one or more alternate dosages of the one or more treatment, wherein the one or more alternate dosages are calculated to compensate for the alteration in activity of at least one of the one or more treatment.

37. The system of claim 32, comprising:
circuitry for suggesting one or more dosages of the one or more treatment to a system user;
circuitry for identifying at least one dietary factor associated with an alteration in activity of at least one of the one or more treatment; and
circuitry for communicating one or more alternate dosages of the one or more treatment, wherein the one or more alternate dosages are calculated to compensate for the alteration in activity of at least one of the one or more treatment.

38. The system of claim 32, comprising:
circuitry for identifying at least one dietary factor associated with activity of the at least one CYP450-family enzyme; and
circuitry for communicating at least one dietary mitigation strategy to a system user.

39. The system of claim 32, comprising:
circuitry for identifying at least one environmental factor associated with activity of the at least one CYP450-family enzyme;
circuitry for requesting information regarding one or more of the at least one environmental factor in relation to the individual; and
circuitry for communicating at least one environmental mitigation strategy to a system user.

40. The system of claim 32, comprising:
circuitry for associating at least one anatomic location with predicted activity of the at least one CYP450-family enzyme;
circuitry for associating the at least one anatomic location with one or more of the at least one modulator; and circuitry for communicating at least one treatment to a system user, wherein the treatment includes the at least one modulator of the at least one CYP450-family enzyme associated with the at least one anatomic location.

41. A system, comprising:

at least one computer program for use with at least one computer system and wherein the computer program includes a plurality of instructions including but not limited to:

one or more instructions for accepting input that specifies an individual;

one or more instructions for accepting input that identifies a drug therapy associated with the individual;

one or more instructions for identifying at least one first CYP450-family enzyme that influences metabolism of the drug therapy associated with the individual;

one or more instructions for identifying at least one second CYP450-family enzyme that influences metabolism of the drug therapy associated with the individual;

one or more instructions for identifying at least one modulator of one or more of the at least one first CYP450-family enzyme;

one or more instructions for identifying at least one modulator of one or more of the at least one second CYP450-family enzyme; and one or more instructions for communicating one or more treatment to a system user, wherein the treatment includes one or more of the identified at least one modulator of one or more of the at least one first CYP450-family enzyme and one or more of the identified at least one modulator of one or more of the at least one second CYP450-family enzyme.

42. A system comprising:

at least one computer program for use with at least one computer system and wherein the computer program includes a plurality of instructions including but not limited to:

one or more instructions for accepting input that specifies an individual;

one or more instructions for accepting input that identifies a first drug therapy associated with the individual;

one or more instructions for accepting input that identifies a second drug therapy associated with the individual;

one or more instructions for identifying at least one CYP450-family enzyme that influences metabolism of both the first drug therapy and the second drug therapy;

one or more instructions for identifying at least one modulator of one or more of the at least one CYP450-family enzyme; and one or more instructions for communicating one or more treatment to a system user, wherein the one or more treatment includes one or more of the at least one modulator.

* * * * *